US008338387B2

(12) United States Patent
Hsieh-Wilson et al.

(10) Patent No.: US 8,338,387 B2
(45) Date of Patent: Dec. 25, 2012

(54) SMALL MOLECULE STIMULATORS OF NEURONAL GROWTH

(75) Inventors: Linda C. Hsieh-Wilson, San Marino, CA (US); Sarah E. Tully, Pasadena, CA (US); Ross Mabon, Princeton, NJ (US); Cristal I. Gama, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 505 days.

(21) Appl. No.: 12/511,944

(22) Filed: Jul. 29, 2009

(65) Prior Publication Data

US 2010/0075920 A1 Mar. 25, 2010

Related U.S. Application Data

(63) Continuation of application No. 11/140,618, filed on May 26, 2005, now Pat. No. 7,638,503.

(60) Provisional application No. 60/574,433, filed on May 26, 2004.

(51) Int. Cl.
*A61K 31/726* (2006.01)
*A61K 31/7016* (2006.01)
*A61K 31/702* (2006.01)
*C07H 5/06* (2006.01)
*C08B 37/00* (2006.01)

(52) U.S. Cl. ............................. 514/54; 514/61; 536/55.1

(58) Field of Classification Search ......................... None
See application file for complete search history.

(56) References Cited

U.S. PATENT DOCUMENTS

| | | | |
|---|---|---|---|
| 6,680,304 B2 | 1/2004 | Pahi et al. | |
| 7,638,503 B2 | 12/2009 | Hsieh-Wilson et al. | |
| 2004/0186142 A1* | 9/2004 | Taveras et al. | 514/341 |
| 2006/0025379 A1 | 2/2006 | Hsieh-Wilson et al. | |
| 2006/0211651 A1* | 9/2006 | Miyasaka et al. | 514/54 |
| 2010/0071080 A1* | 3/2010 | Tully et al. | 800/4 |

FOREIGN PATENT DOCUMENTS

| | | | |
|---|---|---|---|
| WO | WO 03/002125 A2 | | 9/2003 |
| WO | WO 03/002125 A3 | | 11/2003 |
| WO | WO2004/011662 | * | 2/2004 |

OTHER PUBLICATIONS

The Merck Manual of Diagnosis and Therapy, Seventeenth Edition, published 1999 by Merck Research Laboratories, pp. 1341-1359.*
International preliminary report on patentability dated Nov. 29, 2006 for PCT Application No. US2005/018906.
Kinoshita, et al. Isolation and structural determination of novel sulfated hexasaccharides from squid cartilage chondroitin sulfate E that exhibits neuroregulatory activities. Biochemistry. Oct. 23, 2001;40(42):12654-65.
Office action date Jun. 2, 2011 for JP Application No. 2007-515442 (in Japanese with English translation).
Belot, et al. Unexpected stereochemical outcome of activated 4,6-O-benzylidene derivatives of the 2-deoxy-2-trichloroacetamido-D-galacto series in glycosylation reactions during the synthesis of a chondroitin 6-sulfate trisaccharide methyl glycoside. Carb. Res. (2000) 325:93-106.
Blatter, et al. The use of 2-deoxy-2-trichloroacetamido-D-glucopyranose derivatives in synthesis of oligosaccharides. Carb. Res. (1994) 260:189-202.
Bradbury, et al. Chondroitinase ABC promotes function recovery after spinal cord injury. Nature. 2002; 416:636-640.
Brittis, et al. Chondroitin sulfate as a regulator of neuronal patterning in the retina. Science. 1992; 255:733-736.
Dou, et al. Differential effects of glycosaminoglycans on neurite growth on laminin and L1 substrates. J. Neurosci. 1995; 15:8053-8066.
Emerling, et al. nhibitors and promoters of thalamic neuron adhesion and outgrowth in embryonic neocortex: functional association with chondroitin sulfate. Neuron. 1996; 17:1089-1100.
Falshaw, et al. Comparison of the glycosaminoglycans isolated from the skin and head cartilage of Gould's arrow squid (Nototodarus gouldi). Carbohydrate Polymers. 2000; 41:357-364.
Garrett and Grisham. "Biochemistry" Published 1999 by Saunders College Publishers, p. 236.
Greene, et al. Protective Groups in Organic Synthesis. Published by John Wiley and Sons. 1999; pp. 67-74.
International searh report dated Mar. 10, 2006 for PCT Application No. US2005/018906.
Iyer, et al. Design and synthesis of hyaluronan-mimetic Gemini disaccharides. Tetrahedron (2003) 59:631-638.
Jacquinet, J. Synthesis of the methyl glycosides of the repeating units of chondroitin 4- nad 6-sulfate. Carb. Res. (1990) 199:153-181.
Kalovidouris, et al. A role for fucose a (1-2) galactose carbohydrates in neuronal growth. J. Am. Chem. Soc. 2005; 127:1340-1341.
Karst, et al. Chemical synthesis β-D-GlcpA(2SO4)-(1->3)-D-GalpNAc(6SO4), the disaccharide repeating unit of shark cartilage chondroitin sulfate D, and of its methyl β-glycoside derivative. J. Chem. Soc. Perkin Trans. 2000; 1:2709-2717.
Karst, et al. Stereocontrolled total syntheses of shark cartilage chondroitin sulfate D-related tetra- and hexasaccharide methy glycosides. Eur. J. Org. Chem. 2002; 815-825.
Koshiishi, et al. Analysis of chondroitin sulfate/dermatan sulfate chains in rat peritoneal resident macrophages. J. Biol. Pharm. Bull. 1993; 16:307-308.
Lucas, et al. Synthesis of heparin-like pentamers containing "opened" uronic acid moieties. Tetrahedron. 1990; 46:8207-8228.
Marra, et al. Synthesis of disaccharide fragments of dermatan sulfate. Carb. Res. 1989; 195:39-50.
Mizuguchi, et al. Chondroitin proteoglycans are involved in cell division of Caenohabditis elegans. Nature. 2003; 423:443-448.
Nadanaka, et al. Characteristic hexasaccharide sequences in octasaccharides derived from shark cartilage chondroitin sulfate D with a neurite outgrowth promoting activity. J. Biol. Chem. 1998; 273:3296-3307.

(Continued)

*Primary Examiner* — Eric S Olson
(74) *Attorney, Agent, or Firm* — Wilson Sonsini Goodrich & Rosati

(57) ABSTRACT

Provided herein are small molecule stimulators of neuronal growth, their preparation, and their use for treatment of neurological disorders. In one embodiment, provided herein are methods of treatment, prevention, or amelioration of a variety of medical conditions associated with neurological disorders using the compounds and compositions provided herein.

14 Claims, 7 Drawing Sheets

OTHER PUBLICATIONS

Sandson, et al. The potential application of cyclo-oxygenase type 2 inhibitors to Alzheimer's disease. Expert Opin Investig Drugs. Apr. 1998;7(4):519-26.

Sugahara, et al. Recent advances in the structural biology of chondroitin sulfate and dermatan sulfate. Curr. Opin. Chem. Biol. 2003; 13:612-620.

Sugahara, et al. Structural studies on the chondroitinase ABC-resistant sulfated tetrasaccharides isolated from various chondroitin sulfate isomers. Carbohydr Res., (1994).

Takagaki, et al. Domain structure of chondroitin sulfate E octasaccharides binding to type V collagen. J Biol Chem. Mar. 15, 2002;277(11):8882-9.

Tamura, et al. A regio- and stereoselective synthesis of 4-O-sulfated chondroitin di- and tetrasaccharides based on the strategy designed for the elongation of the repeating unit. Bioorg. Medic. Chem. Lett. 1995; 5:1351-1354.

Tamura, et al. Synthetic approach towards sulfated chondroitin di-, tri- and tetrasaccharides corresponding to the repeating unit. Carb. Res. 1998; 305:43-63.

Tsuchida, et al. Appican, the proteoglycan form of the amyloid precursor protein, contains chondroitin sulfate E in the repeating disaccharide region and 4-O-sulfated galactose in the linkage region. J. Biol. Chem. 2001; 276:37155-37160.

Tully, et al. A chondroitin sulfate small molecule that stimulates neuronal growth. J. Am. Chem. Soc. 2004; 126:7736-7737.

Zhang, et al. DDQ-mediated oxidation of 4,6-O-methoxybenzylidene-protected saccharides in the presence of various nucleophiles: formation of 4-OH, 6-Cl, and 6-Br derivatives. J. Org. Chem. 1996; 61:2394-2400.

\* cited by examiner

SMALL MOLECULE STIMULATORS OF NEURONAL GROWTH

RELATED APPLICATION DATA

This application claims the benefit of and is a Continuation Application of U.S. application Ser. No. 11/140,618, filed May 26, 2005 now U.S. Pat. No. 7,638,503 which claims the benefit of U.S. Provisional Application No. 60/574,433, filed May 26, 2004; each of which is hereby incorporated by reference in its entirety.

GRANT INFORMATION

This invention was made with government support under Grant No. RGY 0072 sponsored by Human Frontiers Science Program. The United States government has certain rights in this invention.

FIELD

Provided herein are small molecule stimulators of neuronal growth, their preparation, and their use for treatment of neurological disorders. In another embodiment, provided herein are methods of treatment, prevention, or amelioration of a variety of medical conditions associated with neurological disorders using the compounds and compositions provided herein.

BACKGROUND

Neurological disorders afflict large numbers of people in the world. In disorders ranging from neurodegenerative diseases (e.g., Alzheimer's and Parkinson's diseases) to traumatic spinal cord injuries, there is a need for molecules that promote neuronal growth. While some proteins are known that can stimulate neuronal growth, few small molecules are known that can stimulate neuronal growth.

Chondroitin sulfate (CS) glycosaminoglycans are sulfated polysaccharides implicated in cell division, neuronal development, and spinal cord injury (Mizuguchi, S.; Uyama, T.; Kitagawa, H.; Nomura, K. H.; Dejima, K.; Gengyo-Ando, K.; Nitani, S.; Sugahara, K.; Nomura, K. *Nature* 2003, 423, 443-448; Sugahara, K.; Mikami, T.; Uyama, T.; Mizuguchi, S.; Nomura, K.; Kitagawa, H. *Curr. Op. Chem. Biol.* 2003, 13, 612-620; Bradbury, E. J.; Moon, L. D. F.; Popat, R. J.; King, V. R.; Bennett, G. S.; Patel, P. N.; Fawcett, J. W.; McMahon, S. B. *Nature* 2002, 416, 636-640.). As with all glycosaminoglycans, the complexity and heterogeneity of Chondroitin sulfate (CS) glycosaminoglycans have hampered efforts to understand its precise biological roles. For instance, CS has been shown to prevent the growth of axons; yet it is also found in developing, growth-permissive regions. (Bradbury et al., supra; Emerling, D. E.; Lander, A. D. *Neuron* 1996, 17, 1089-1100). CS polysaccharides have been shown both to stimulate and to attenuate the growth of cultured neurons. (Brittis, P. A. et al. *Science* 1992, 255, 733-736; Dou, C. L.; Levine, J. M. *J. Neurosci.* 1995, 15, 8053-8066; Nadanaka, S. et al. *J. Biol. Chem.* 1998, 273, 3296-3307.) Notably, the molecules used in those studies were ~200 saccharides in length, poorly defined, and heterogeneously sulfated, features that might account for the contradictory observations.

In addition, CS having a particular sulfation pattern (CS-E) is found on the protein appican, an isoform of the amyloid precursor protein that exhibits neurotrophic activity (Tsuchida, K. et al. *J. Biol. Chem.* 2001, 276, 37155-37160). Moreover, polysaccharides enriched in the CS-E motif have been shown to promote the outgrowth of neurons (Nadanaka, S. et al. *J. Biol. Chem.* 1998, 273, 3296-3307).

Because of the interest in studying neuronal growth and differentiation, there is a need for small molecule modulators of neuronal growth.

SUMMARY

Provided herein are small molecule compounds that are modulators of neuronal growth. The compounds provided herein are oligosaccharides or oligosaccharide-like molecules having a plurality of negatively charged moieties. Also provided are compositions and methods of using the compounds and compositions for the treatment of conditions associated with neurological disorders.

In certain embodiments, the compounds provided herein are polysaccharides containing repeating dimer units of formula I:

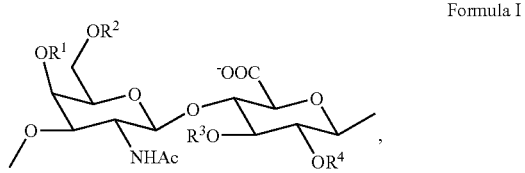

Formula I wherein $R^1$, $R^2$, $R^3$ and $R^4$ are each independently selected from hydrogen or negatively charged groups, including but not limited to sulfate, phosphate and carboxylate; with a proviso that a) at least one of $R^1$, $R^2$, $R^3$ or $R^4$ is not hydrogen;
b) when $R^1$ is sulfate, $R^2$ is not OH; and
c) when $R^2$ is sulfate, $R^1$ is not OH.

In certain embodiments, the compounds provided herein have formula II:

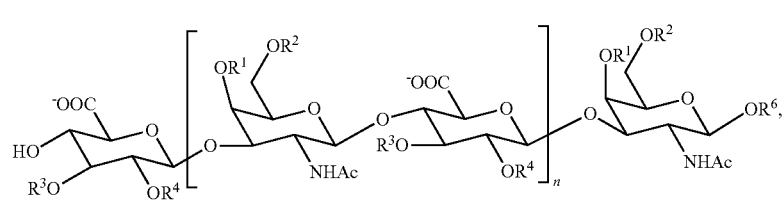

Formula II or pharmaceutically acceptable derivatives thereof, wherein $R^1$, $R^2$, $R^3$ and $R^4$ are each independently selected from hydrogen or negatively charged groups, including but not limited to sulfate, phosphate and carboxylate; $R^6$ is selected from optionally substituted alkyl, optionally substituted alkenyl or optionally substituted alkynyl; and n is 0-100; provided that at least one of $R^1$, $R^2$, $R^3$ and $R^4$ is not hydrogen.

Pharmaceutically-acceptable derivatives, including salts, esters, enol ethers, enol esters, solvates, hydrates and prodrugs of the compounds described herein are provided herein. Further provided are pharmaceutical compositions containing the compounds provided herein and a pharmaceutically acceptable carrier. In one embodiment, the pharmaceutical compositions are formulated for single dosage administration.

Methods of treating, using the compounds and compositions herein are provided. Methods of treating, preventing, or ameliorating one or more symptoms associated with neurological disorders using the compounds and compositions provided herein are provided. In practicing the methods, effective amounts of the compounds or compositions containing therapeutically effective concentrations of the compounds are administered. In certain embodiments, the compounds provided herein are used in conjunction with proteins or other factors to stimulate the growth of the implanted tissue. In certain embodiments, the compounds provided herein interact with growth factors and cytokines (e.g., tumor necrosis factor-α or TNFα and nerve growth factor or NGF).

Articles of manufacture are provided containing packaging material, a compound or composition provided herein which is useful for treating, preventing, or ameliorating one or more symptoms associated with neurological disorders using the compounds and compositions provided herein, and a label that indicates that the compound or composition is useful for treating, preventing, or ameliorating one or more symptoms associated with neurological disorders.

DETAILED DESCRIPTION

A. Definitions

Figure 1A:
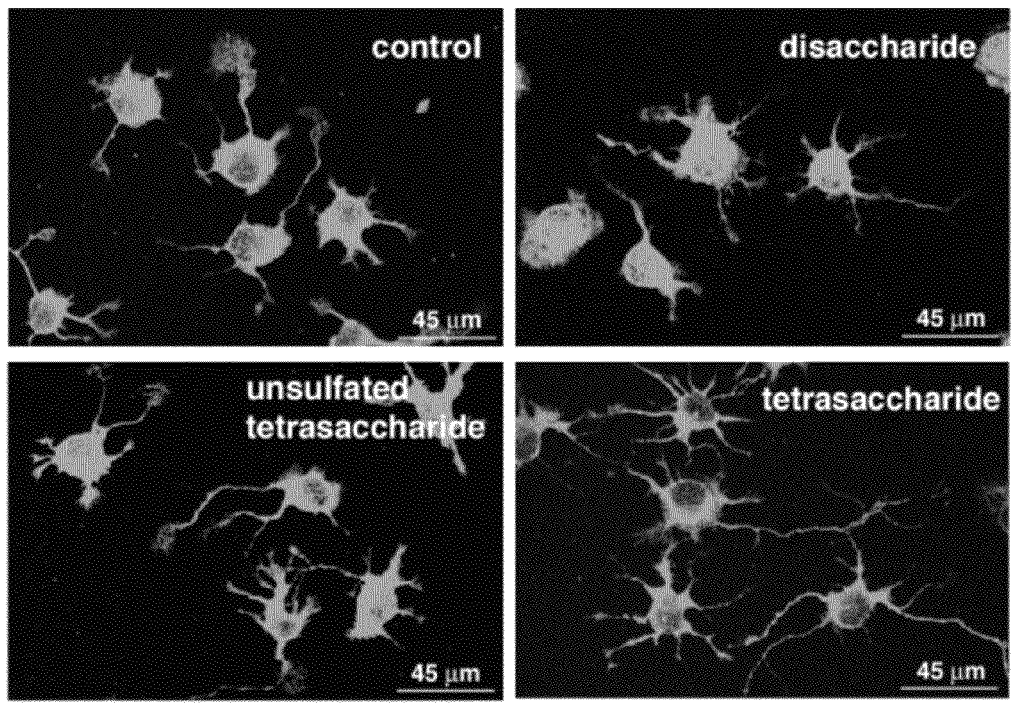
FIGS. 1A-B illustrate the effect of disaccharide CS-E, tetrasaccharide CS-E, and unsulfated tetrasaccharide on neuronal morphology and growth of hippocampal neuron.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, the term "outgrowth" refers to the process by which axons grow out of a neuron. The outgrowth can result in a totally new axon or the repair of a partially damaged axon.

As used herein, the term "CNS neurons" is intended to include the neurons of the brain and the spinal cord which are unresponsive to nerve growth factor (NOF).

As used herein, the term "injury" is intended to include a damage which directly or indirectly affects the normal functioning of the CNS. For example, the injury can be damage to retinal ganglion cells; a traumatic brain injury; a stroke related injury; a cerebral aneurism related injury; a spinal cord injury, including monoplegia, diplegia, paraplegia, hemiplegia and quadriplegia; a neuroproliferative disorder or neuropathic pain syndrome.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, and cycloalkyl. Pharmaceutically acceptable enol esters include, but are not limited to, derivatives of formula C=C(OC(O)R) where R is hydrogen, alkyl, alkenyl, alkynyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, glycopolymers refer to polymers with saccharide groups pendant to the main chain.

As used herein, "linker" refers to the intervening atoms between the two saccharide groups or the saccharide group and the polymer chain. The linker is characterized by a first chemical functional group that connects the first end of the linker to a first saccharide and a second chemical functional group that connects the second end of the linker to a second saccharide of to a polymer backbone.

As used herein, treatment means any manner in which one or more of the symptoms of a disease or disorder are ameliorated or otherwise beneficially altered. Treatment also encompasses any pharmaceutical use of the compositions herein, such as use for treating conditions associated with neurological disorders.

As used herein, amelioration of the symptoms of a particular disorder by administration of a particular compound or pharmaceutical composition refers to any lessening, whether permanent or temporary, lasting or transient that can be attributed to or associated with administration of the compound or composition provided herein.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). Other prodrugs for use herein are described elsewhere herein.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the present invention encompasses any racemic, optically active, polymorphic, or stereoisomeric form, or mixtures thereof, of a compound of the invention, which possesses the useful properties described herein, it being well known in the art how to prepare optically active forms and how to determine antiproliferative activity using the standard tests described herein, or using other similar tests which are well known in the art.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the term "alkyl" refers to a monovalent straight or branched chain or cyclic radical. In certain embodiments, the alkyl group contains from one to twenty-four carbon atoms, including methyl, ethyl, n-propyl, isopropyl, n-butyl, isobutyl, tert-butyl, n-hexyl, octadecyl, nonadecyl, eicosyl, 18-methyl-nonadecyl, 19-methyl-eicosyl, and the like. As used herein lower alkyl refers to alkyl groups of 1 to 6 carbon atoms.

As used herein, "substituted alkyl" refers to alkyl groups further bearing one or more substituents, including, but not limited to substituents selected from lower alkyl, hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, azido, nitro, nitrone, amino, amino, —C(O)H, acyl, oxyacyl, carboxyl, carbamate, sulfonyl, sulfonamide, and sulfuryl, which may be protected or unprotected as necessary, as taught in Greene, et al., Protective Groups in Organic Synthesis, John Wiley and Sons, Second Ed. 1991, hereby incorporated by reference.

As used herein, "alkenyl" refers to straight or branched chain hydrocarbon group having one or more carbon-carbon double bonds. In certain embodiments, the alkenyl group contains from 2 up to 24 carbon atoms, and "substituted alkenyl" refers to alkenyl groups further bearing one or more substituents as set forth above.

As used herein, "alkynyl" refers to straight or branched chain hydrocarbon group having one or more carbon-carbon triple bonds. In certain embodiments, the alkynyl group contains from 2 up to 24 carbon atoms, and "substituted alkynyl" refers to alkynyl groups further bearing one or more substituents as set forth above.

Where the number of any given substituent is not specified (e.g., haloalkyl), there may be one or more substituents present. For example, "haloalkyl" may include one or more of the same or different halogens.

As used herein "subject" is an animal, typically a mammal, including human, such as a patient.

The phrase "effective amount" as used herein means an amount required for prevention, treatment, or amelioration of one or more of the symptoms associated with neurological disorders. Effective amounts can be measured by any methods known to one of skill in the art. In certain embodiments, effective amounts can be measured by improvements in neuronal or ganglion cell survival, axonal regrowth or neurodegeneration and connectivity following axotomy using well known methods. See, e.g., Bray, et al., "Neuronal and Normeuronal Influences on Retinal Ganglion Cell Survival, Axonal Regrowth, and Connectivity After Axotomy", Ann. N.Y. Acad. Sci., pp. 214-228 (1991).

As used herein, the term "parenteral" includes subcutaneous, intravenous, intra-arterial, intramuscular, intrathecal or intravitreal injection, or infusion techniques.

The term "topically" encompasses administration rectally and by inhalation spray, as well as the more common routes of the skin and mucous membranes of the mouth and nose and in toothpaste.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:942-944).

B. Compounds

In one embodiment, the compounds for use in the compositions and methods provided herein have formula:

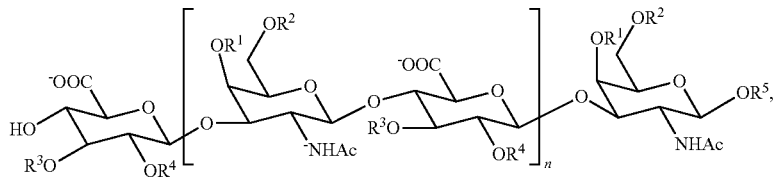

or pharmaceutically acceptable derivatives thereof, wherein $R^1$, $R^2$, $R^3$ and $R^4$ are each independently selected as follows:

i) $R^1$ and $R^2$ are each independently selected from sulfate, phosphate and carboxylate; and $R^3$ and $R^4$ are hydrogen;

ii) $R^3$ and $R^4$ are each independently selected from sulfate, phosphate and carboxylate; and $R^1$ and $R^2$ are hydrogen;

iii) $R^1$, $R^2$ and $R^3$ are each independently selected from sulfate, phosphate and carboxylate; and $R^4$ is hydrogen;

iv) $R^1$, $R^2$ and $R^4$ are each independently selected from sulfate, phosphate and carboxylate; and $R^3$ is hydrogen;

v) $R^2$ and $R^4$ are each independently selected from sulfate, phosphate and carboxylate; and $R^1$ and $R^3$ are hydrogen;

vi) $R^1$ is selected from sulfate, phosphate and carboxylate; and $R^2$, $R^3$ and $R^4$ are hydrogen;

vii) $R^2$ is selected from sulfate, phosphate and carboxylate; and $R^1$, $R^3$ and $R^4$ are hydrogen;

viii) $R^3$ is selected from sulfate, phosphate and carboxylate; and $R^2$, $R^4$ and $R^1$ are hydrogen; or ix) $R^4$ is selected from sulfate, phosphate and carboxylate; and $R^1$, $R^2$ and $R^3$ are hydrogen;

$R^5$ is optionally substituted alkyl or optionally substituted alkenyl; and n is 0-100.

In another embodiment, n is 0-50. In another embodiment, n is 0-25. In another embodiment, n is 0-20. In another embodiment, n is 0-15. In another embodiment, n is 0-10. In another embodiment, n is 0-5. In another embodiment, n is 0-4. In another embodiment, n is 2-4. In another embodiment, n is 4. In another embodiment, n is 3. In another embodiment, n is 2. In another embodiment, n is 1. In another embodiment, n is 0, 1, 2, 3 or 4.

In another embodiment, $R^5$ is lower alkenyl. In another embodiment, $R^5$ is allyl.

In another embodiment, $R^1$ is selected from hydrogen, sulfate, phosphate and carboxylate. In another embodiment, $R^1$ is sulfate.

In another embodiment, $R^2$ is selected from hydrogen, sulfate, phosphate and carboxylate. In another embodiment, $R^2$ is sulfate. In another embodiment, $R^1$ is hydrogen.

In another embodiment, $R^3$ is selected from hydrogen, sulfate, phosphate and carboxylate. In another embodiment, $R^3$ is sulfate. In another embodiment, $R^3$ is hydrogen.

In another embodiment, $R^4$ is selected from hydrogen, sulfate, phosphate and carboxylate. In another embodiment, $R^4$ is sulfate. In another embodiment, $R^4$ is hydrogen.

In one embodiment, the compounds provided herein have formula III:

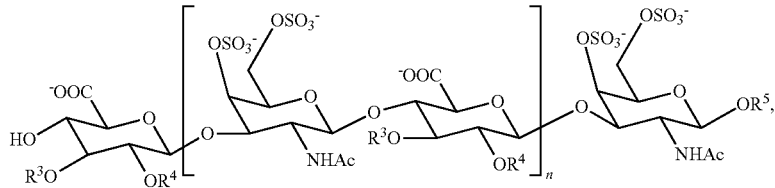

wherein the variables are as described elsewhere herein.

In one embodiment, the compounds provided herein have formula IV:

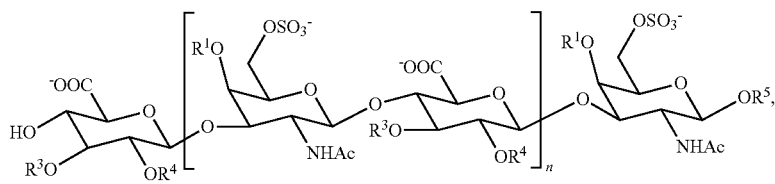

wherein the variables are as described elsewhere herein.

In one embodiment, the compounds provided herein have formula V:

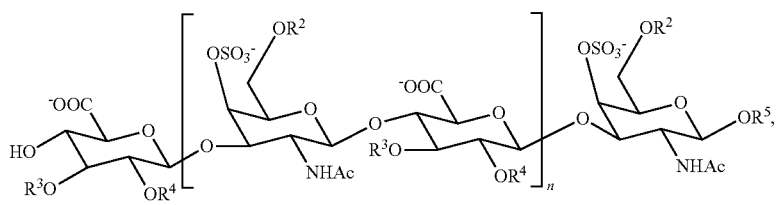

wherein the variables are as described elsewhere herein.

In one embodiment, the compounds provided herein have formula VI:

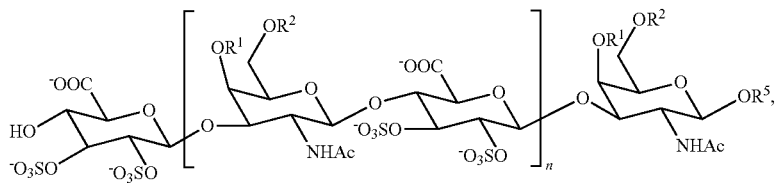

wherein the variables are as described elsewhere herein.

In one embodiment, the compounds provided herein have formula VI:

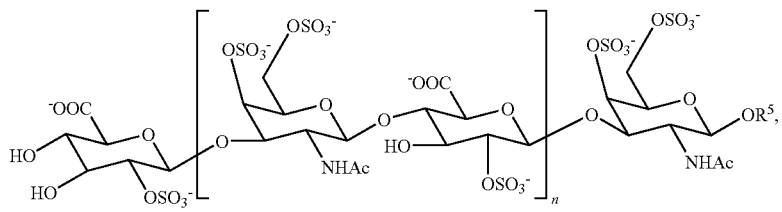

In one embodiment, the compounds provided herein have formula VII:

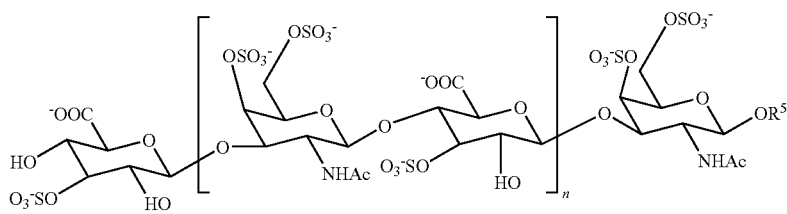

wherein the variables are as described elsewhere herein.

In one embodiment, the compounds provided herein have formula VIII:

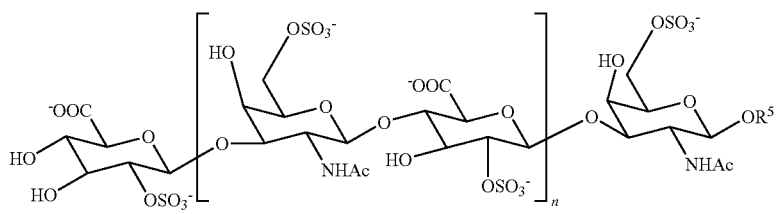

wherein the variables are as described elsewhere herein.

In one embodiment, the compounds provided herein have formula IX:

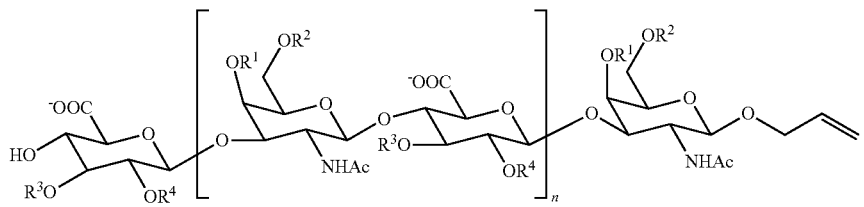

wherein the variables are as described elsewhere herein.

In one embodiment, the compounds provided herein have formula X:

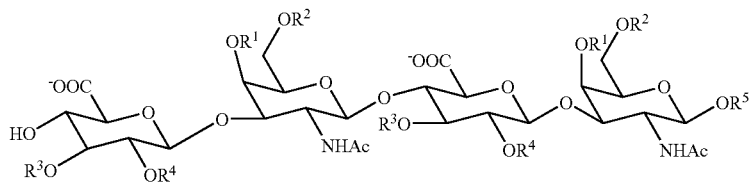

wherein the variables are as described elsewhere herein.

In one embodiment, the compounds provided herein have formula XI:

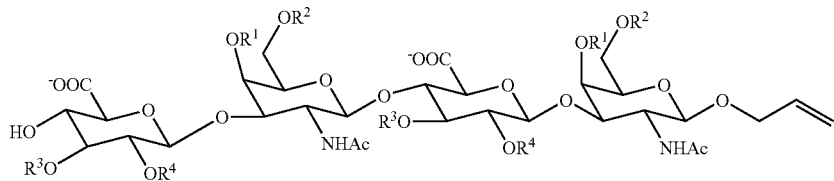

wherein the variables are as described elsewhere herein.

In one embodiment, the compounds provided herein are selected from:

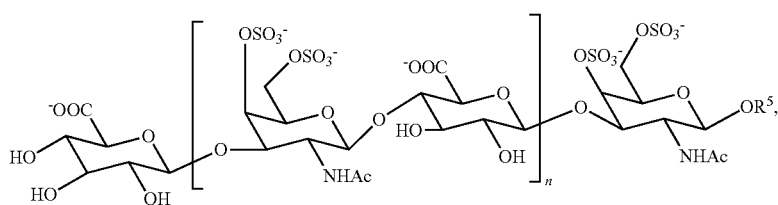

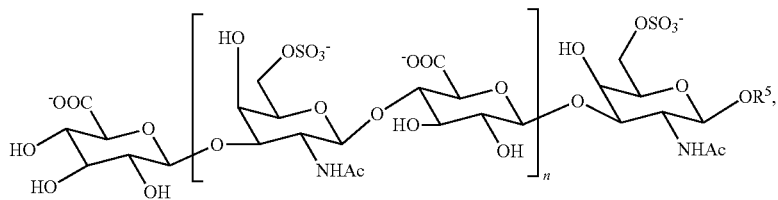

-continued
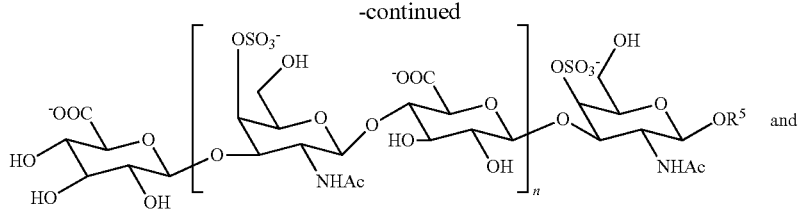
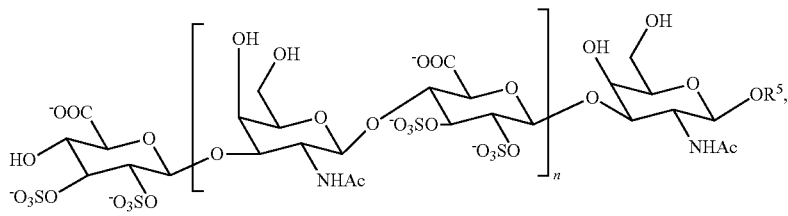
wherein the variables are as described elsewhere herein.
In one embodiment, the compound provided herein is selected from:
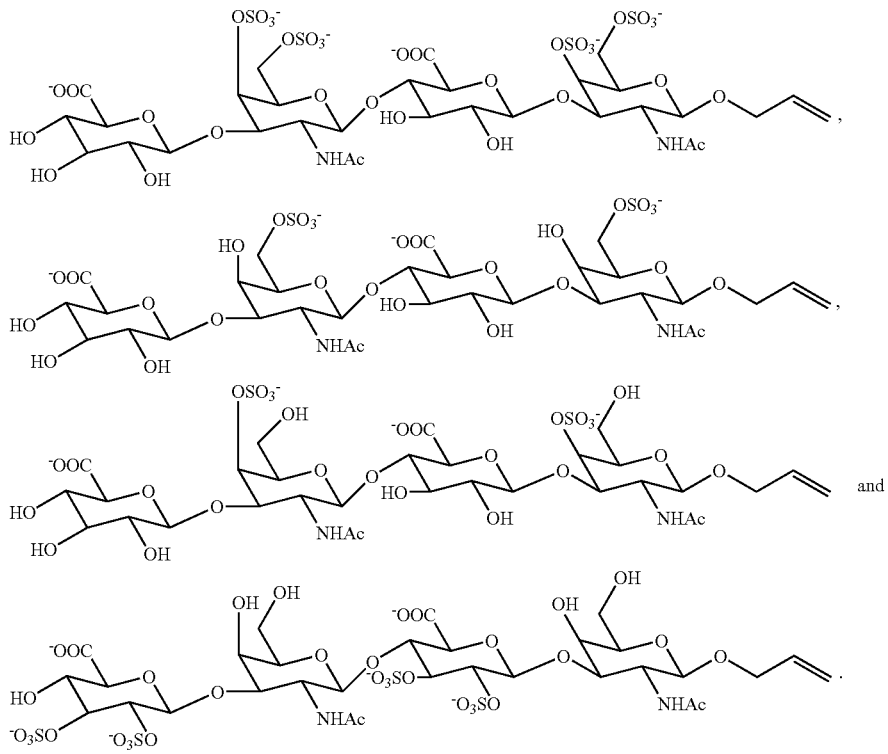
In one embodiment, the compound is selected from:
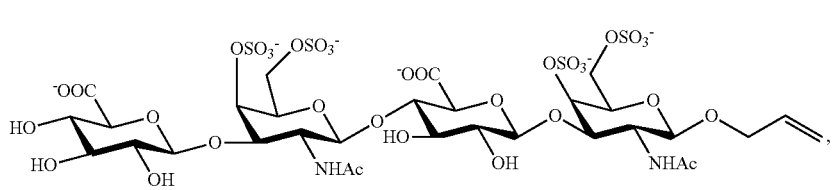

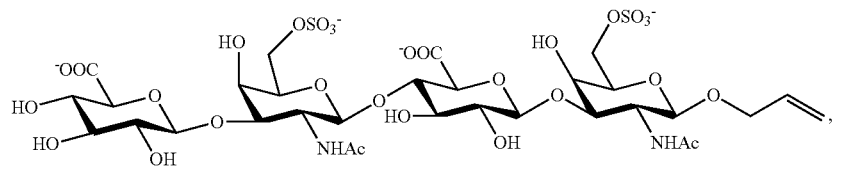

CS-C

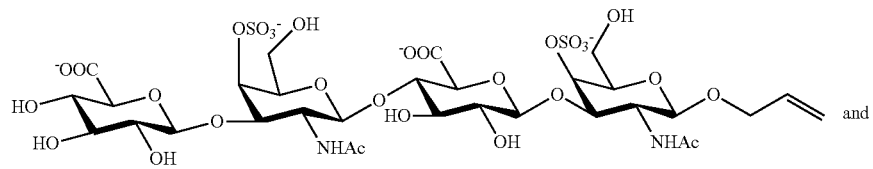

CS-A and

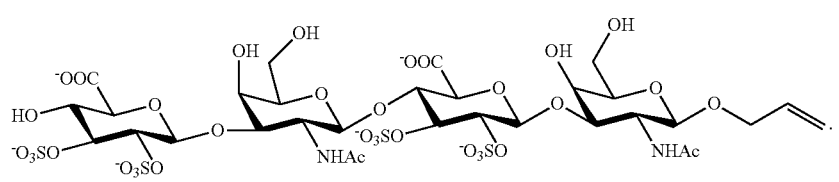

CS-R

In one embodiment, the compound is

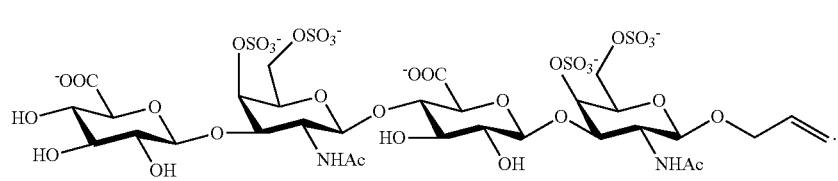

CS-E

In certain embodiments, the compounds provided herein are substantially pure. In certain embodiments, the negatively charged groups in the compounds provided herein can be prepared as a protected derivative that is unmasked in the biological milieu, e.g., an ester that can be cleaved to give a carboxyate.

In certain embodiments, the compounds provided herein are polysaccharides containing repeating dimer units of formula I:

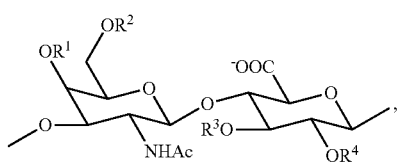

Formula I wherein $R^1$ and $R^2$ are sulfate and the other variables are as described elsewhere herein. In certain embodiments, the compounds provided herein are polysaccharides containing repeating dimer units of formula I, wherein $R^1$ and $R^2$ are sulfate and $R^3$ and $R^4$ are hydrogen.

In certain embodiments, the compounds provided herein are linked with various linker moieties to be polyvalent. In one embodiment, the linker moieties used are labile under biological conditions, such that upon exposure to biological conditions, the linker will be severed and will release the compound provided herein. Such linkers are known in the art.

In certain embodiments, the linkers are bifunctional molecules that can form a bond between the two saccharide moieties. The linker can be homobifunctional or heterobifunctional. Examples of functional groups on the linker include, but are not limited to —$NH_2$, —$ONH_2$, —NHC=(O), —OH, —CHO, —$CO_2H$, and —SH. Each of these functional groups can form a covalent linkage between the two saccharide.

The linker can include linear or acyclic portions, cyclic portions, aromatic rings or combinations thereof. In certain embodiments, the linker can have from 1 to 100 main chain atoms other than hydrogen atoms, selected from C, N, O, S, P and Si. In certain embodiments the linker contains up to 50 main chain atoms other than hydrogen, up to 40, up to 30, up to 20, up to 15, up to 10, up to 5, up to 2 main chain atoms other than hydrogen. In certain embodiments the linker is acyclic. In certain embodiments, the linker contains oligomers of ethylene glycol or alkylene chains or mixtures thereof.

In certain embodiments, the linker has formula:

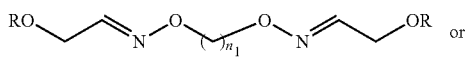

or

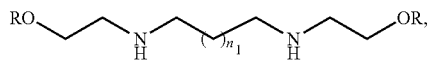

wherein $n_1$, is 1-100, 1-50, 1-40, 1-30, 1-20, 1-10, 1-9, 1-8, 1-7, 1-6, 1-5, 1-4, 1-3, 2 or 1 and R is

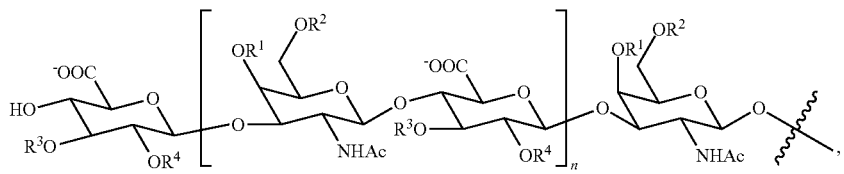

Where the variables are as described elsewhere herein.

In certain embodiments, the compounds with linker contain the repeating disaccharide units linked via a linker. In certain embodiments, the compound is dimer CS-E of formula:

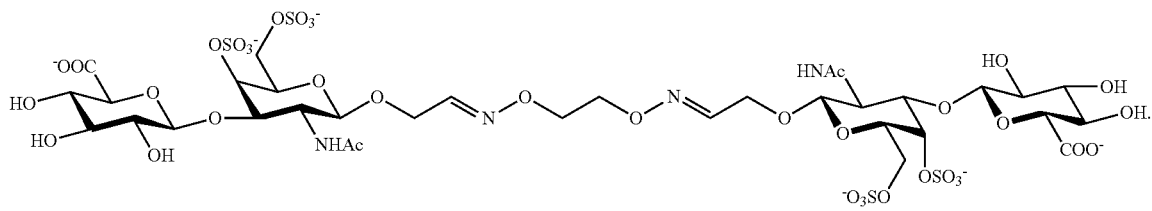

In certain embodiments, the saccharide compounds with repeating units of formula I or compounds of formula II are copolymerized or grafted into polymer backbonse to form glycopolymers. The polymer backbone in certain embodiments, is a straight chain, in other embodiments it is a branched polymer. In certain embodiments, the glycopolymer provided herein contains between about 2 and about 1000 pendent saccharide moieties.

The saccharide compounds with repeating units of formula I or compounds of formula II can be linked to the polymer backbone via linkers. The linkers are bifunctional molecules that can form a bond between the saccharide and the polymer backbone. The linker can be homobifunctional or heterobifunctional. Examples of functional groups on the linker include, but are not limited to —$NH_2$, —$ONH_2$, —NHC=(O), —OH, —CHO, —$CO_2H$, and —SH. Each of these functional groups can form a covalent linkage between the saccharide and the polymer backbone.

The linker can include linear or acyclic portions, cyclic portions, aromatic rings or combinations thereof. In certain embodiments, the linker can have from 1 to 100 main chain atoms other than hydrogen atoms, selected from C, N, O, S, P and Si. In certain embodiments the linker contains up to 50 main chain atoms other than hydrogen, up to 40, up to 30, up to 20, up to 15, up to 10, up to 5, up to 2 main chain atoms other than hydrogen. In certain embodiments the linker is acyclic. In certain embodiments, the linker contains oligomers of ethylene glycol or alkylene chains or mixtures thereof.

The polymer backbones for use herein are known in the art. In certain embodiments, the polymer backbone is polyacrylamide based. In other embodiments, the polymer is selected from polyacrylamide, polyacrylate and poly(N-acryloxy) succinimide.

In certain embodiments, the glycopolymers provided herein are selected from:

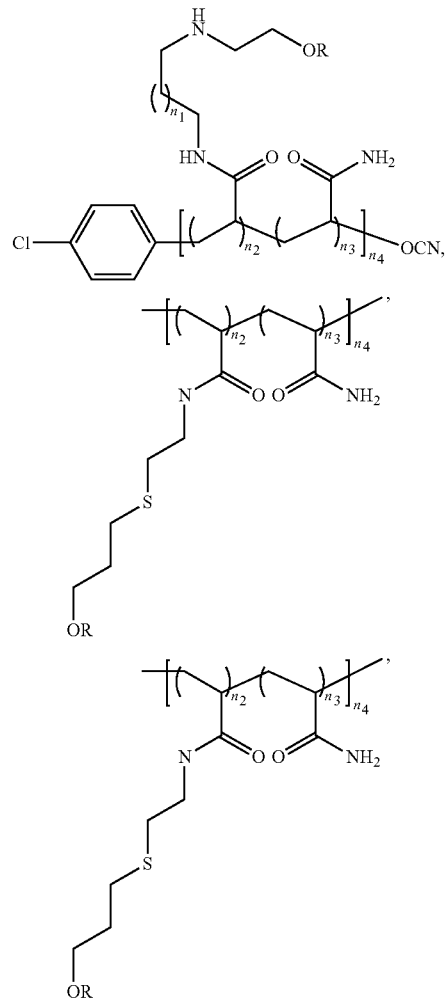

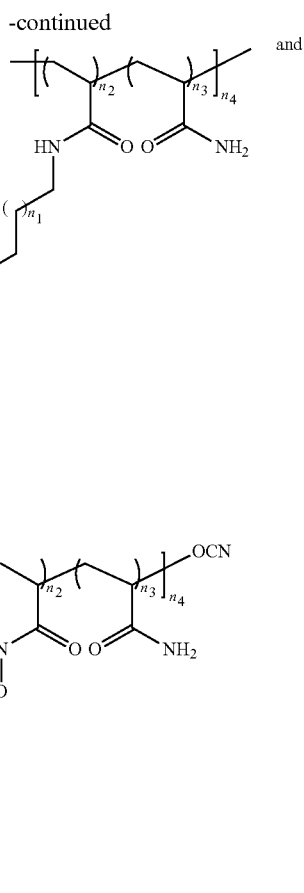

wherein $n_1$, $n_2$, $n_3$ and $n_4$ are each independently 1-100, 1-50, 1-40, 1-30, 1-20, 1-10, 1-9, 1-8, 1-7, 1-6, 1-5, 1-4, 1-3, 2 or 1 and the other variables are as described elsewhere herein.

C. Preparation of Compounds

The compounds provided herein can be prepared by using routine chemical reactions known in the art. In certain embodiments, the compounds can be prepared by using a convergent strategy (illustrated in schemes 1-3) to access various CS-E molecules from a single disaccharide building block, 4. The sulfated 4- and 6-hydroxyls of D-galactosamine were masked with a p-methoxybenzylidene acetal. This group allows access to other sulfation motifs (e.g., CS-A, CS-C). In certain embodiments, the reactions can be extended to solid-phase methodologies. In particular, oxidative removal using DDQ (Zhang, Z. Y.; Magnusson, G. *J. Org. Chem.* 1996, 61, 2394-2400) or regioselective opening of the acetal ring (Tamura, J. et al. *Carbohydr. Res.* 1997, 305, 43-63; Johansson, R.; Samuelsson, B. *J. Chem. Soc.-Perkin Trans.* 1 1984, 2371-2374), in certain embodiments, permits selective deprotection of either or both the 4- and 6-hydroxyls and circumvents the need for hydrogenolysis. The orthogonal tert-butyldimethylsilyl group can be installed at the C-4 position on the non-reducing end of 4 to facilitate chain elongation. To achieve stereoselective formation of β-glycosidic linkages, N-trichloroacetyl and benzoyl participating groups are used (Coutant, C.; Jacquinet, J. C. *J. Chem. Soc.-Perkin Trans.* 1 1995, 1573-1581). Finally, the anomeric hydroxyl of 4 is masked with an allyl group, which could be converted to activated glycosyl donors and offers a convenient means to conjugate CS to small molecules, proteins or surfaces.

The synthesis of the target compounds is illustrated in Scheme 1. Monosaccharides 5 and 6 were generated from known p-tolyl-1-thio-β-D-glucopyranose (Clingman, A. L.; Richtmyer, N. K. *J. Org. Chem.* 1964, 29, 1782-1787.) or 1,3,4,6-tetra-O-acetyl-2-azido-2-deoxy-D-galactopyranose (Lemieux, R. U.; Ratcliffe, R. M. *Can. J. Chem.-Rev. Can. Chim.* 1979, 57, 1244-1251), respectively (Schemes 2 and 3). Coupling of 5 with 6 using the trichloroacetimidate procedure (Schmidt, R. R.; Kinzy, W. In *Adv. Carbohydr. Chem. Biochem.*, 1994; Vol. 50, pp 21-123) afforded exclusively the β-linked disaccharide 4 in 74% yield. At this stage, activation of the disaccharide, in certain embodiments, proceeds through conversion of the C-1 allyl group to the lactol. However, conventional methods such as $PdCl_2$, $Pd(PPh_3)_4$, [Ir(COD)(PMePh$_2$)$_2$]PF$_6$ and Wilkinson's catalyst did not yield the desired isomerization, presumably due to interference by the neighboring trichloroacetamide (a related 2-acetamido derivative underwent isomerization readily upon treatment with [Ir(COD)(PMePh$_2$)$_2$]PF$_6$.) Treatment with Grubbs' second-generation catalyst (Scholl, M.; Ding, S.; Lee, C. W.; Grubbs, R. H. *Org. Lett.* 1999, 1, 953-956) in the presence of $H_2$ led to the desired outcome. Hydrolysis of the enol ether and conversion to tichloroacetimidate 7 proceeded smoothly under standard conditions (Driguez, P. A.; Lederman, I.; Strassel, J. M.; Herbert, J. M.; Petitou, M. *J. Org. Chem.* 1999, 64, 9512-9520; Shiozaki, M et al. *Carbohydr. Res.* 1991, 222, 57-68). Disaccharide 4 also provided ready access to glycosyl acceptor 8 via desilylation. Subsequent glycosylation of 7 and 8 delivered the desired tetrasaccharide with good stereoselectivity.

The fully protected di- and tetrasaccharides were subjected to the final deprotection-sulfation steps. Radical-mediated conversion of the N-trichloroacetyl group into an N-acetyl (Coutant, C.; Jacquinet, J. C. *J. Chem. Soc.-Perkin Trans.* 1 1995, 1573-1581) followed by oxidative cleavage of the p-methoxybenzylidene acetal (Zhang, Z. Y.; Magnusson, G. *J. Org. Chem.* 1996, 61, 2394-2400.) afforded 9 and 10. Treatment of 9 and 10 with $SO_3$.timethylamine complex in DMF delivered the sulfated compounds in 67% and 93% yield, respectively, see Tamura, J.; Neumann, K. W.; Kurono, S.; Ogawa, T. *Carbohydr. Res.* 1997, 305, 43-63. The target CS-E di- and tetrasaccharides 1 and 2 were obtained after silyl deprotection and saponification utilizing NaOH or sequential LiOOH—NaOH treatment (Lucas, H.; Basten, J. E. M.; Van Dinther, T. G.; Meuleman, D. G.; Van Aelst, S. F.; Van Boeckel, C. A. A. *Tetrahedron* 1990, 46, 8207-8228) to minimize β-elimination at the C-4 position. Deprotection of 9 under similar conditions furnished the unsulfated tetrasaccharide 3.

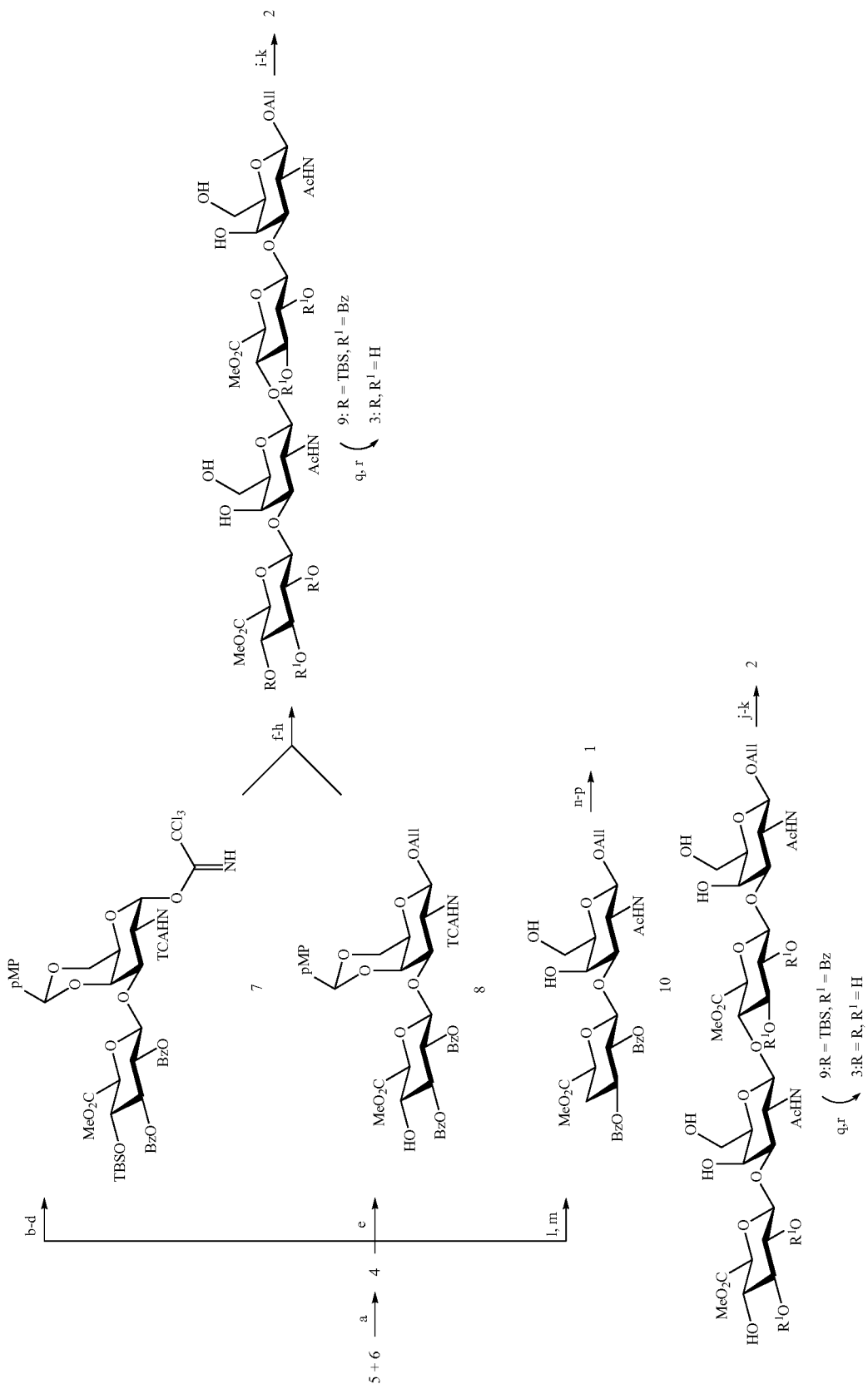
Scheme 1: Synthesis of the tetrasaccharide a) TMSOTf, CH$_2$Cl$_2$, −40° C.→−15° C., 74%. (b) L(PCy$_3$)Cl$_2$Ru=CHPh, L=1,3-dimesitylimidazolylidene (20 mol %), H$_2$, 77%. (c) I$_2$, H$_2$O, pyr/THF, 81%. (d) DBU, CCl$_3$CN, CH$_2$Cl$_2$, 90%. (e) HF.pyr, pyr/THF, 0° C., 85%. (f) TMSOTf, CH$_2$Cl$_2$, −15° C., 31%. (g) TBTH, AIBN, DMA/benzene, 25° C.→80° C., 85%. (h) DDQ, H$_2$O/CH$_2$Cl$_2$, 75%. (i) SO$_3$.Me$_3$N, DMF, 50° C., 67%. (j) HF.pyr, pyr/THF/H$_2$O, 0° C. (k) LiOH, H$_2$O$_2$, THF/H$_2$O, then NaOH, MeOH/H$_2$O, 25% over three steps. (l) TBTH, AIBN, benzene, 25° C.→80° C., 85%. (m) DDQ, H$_2$O/CH$_2$Cl$_2$, 62%. (n) SO$_3$Me$_3$N, DMF, 50° C., 93%. (o) HF.pyr, pyr/THF/H$_2$O, 0° C. (p) NaOH, MeOH/H$_2$O, 55% over two steps (q) HF.pyr, pyr/THF/H$_2$O, 0° C. (r) LiOH, H$_2$O$_2$, THF/H$_2$O, then NaOH, MeOH/H$_2$O, 52% over three steps.

Scheme 2: Synthesis of the Glucuronic Acid Monomer 5

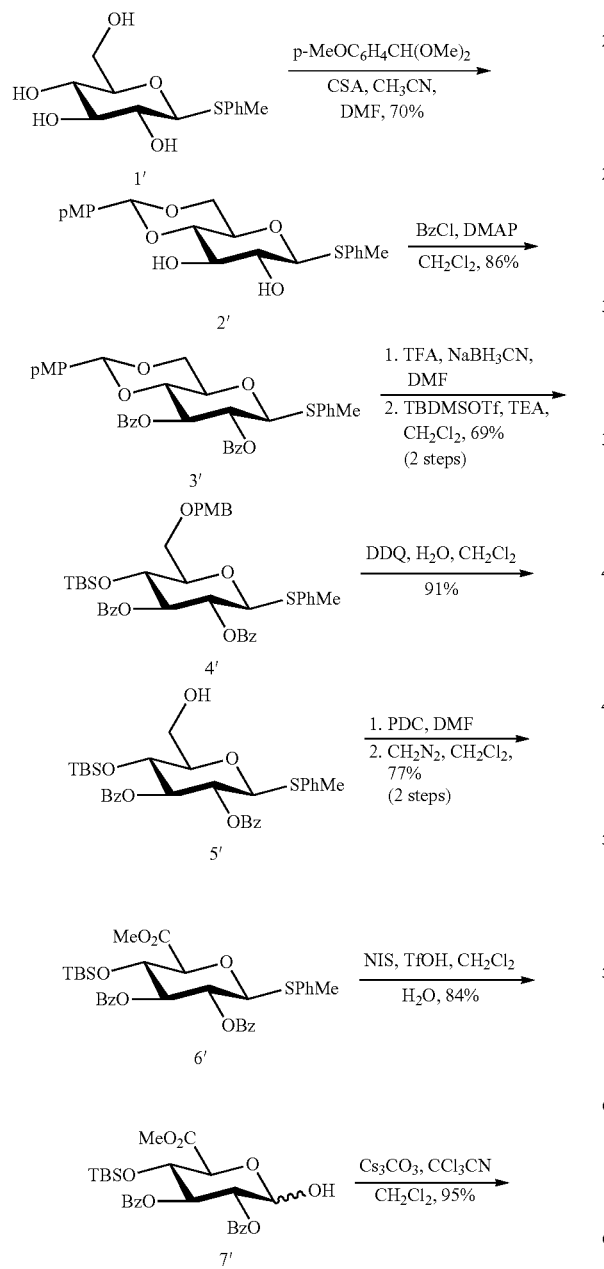

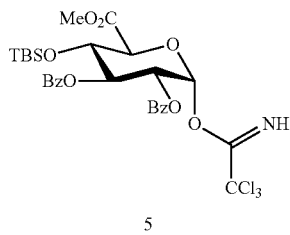

5

Scheme 3: Synthesis of the Galactosamine Monomer 6

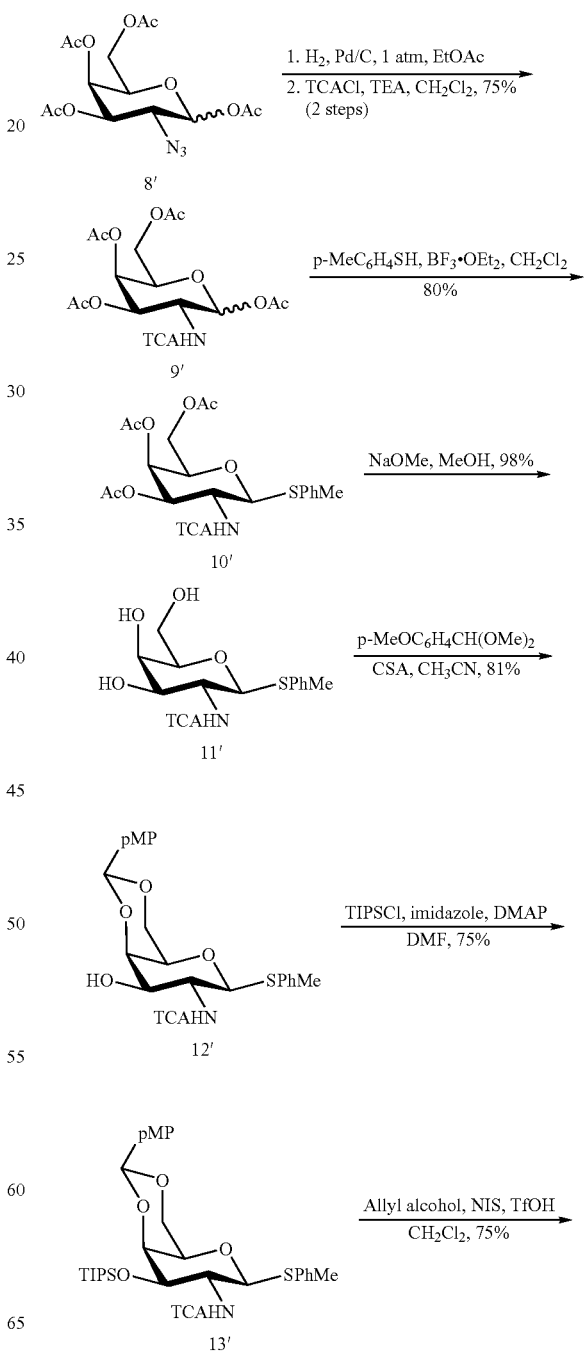

25
-continued
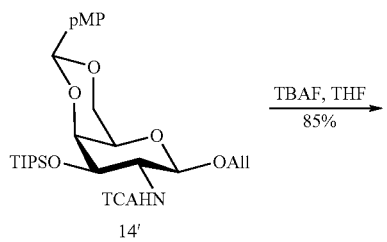
14'
26
-continued
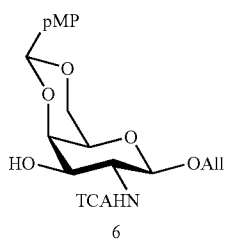
6
Scheme 4 represents synthesis of exemplary compounds provided herein:
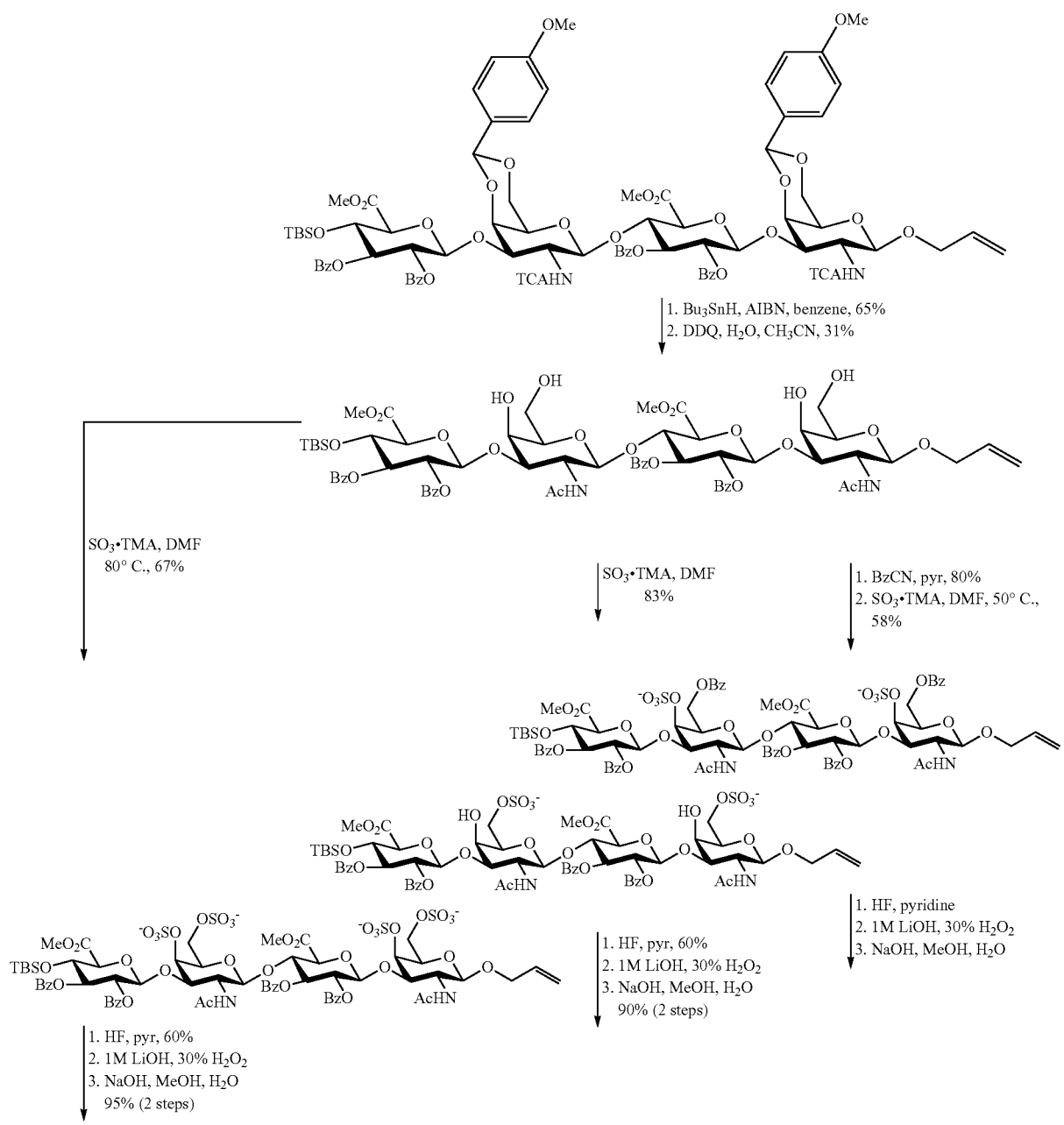

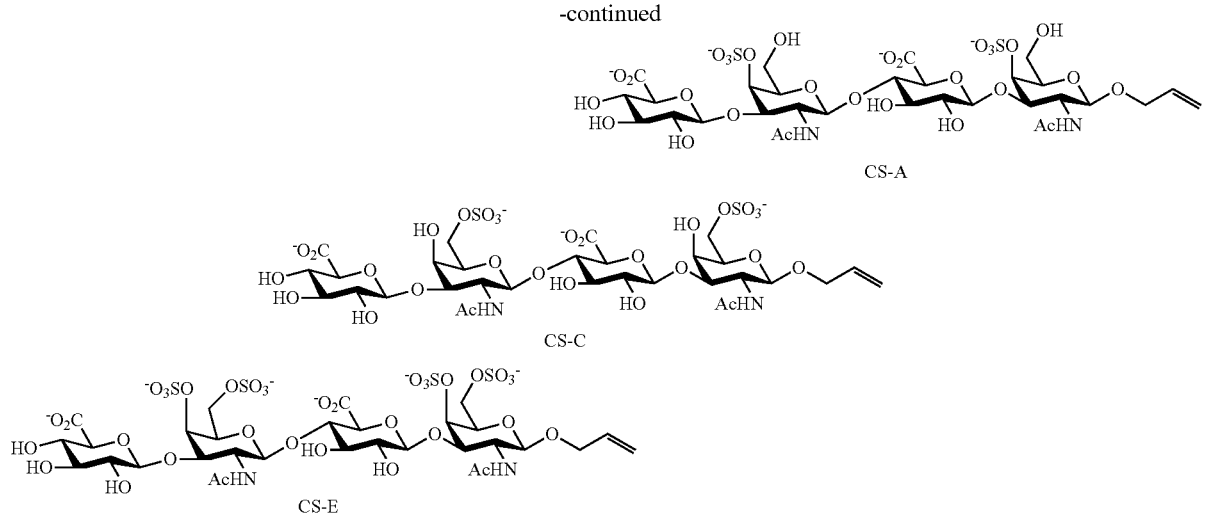

CS-A

CS-C

CS-E

The preparation of glycoconjugates provided herein can be represented as follows:

a) Copolymerization of acrylamide with monomeric acrylamides in which one of the acrylamide possesses the compound of formula I or II described herein.

Scheme 5:

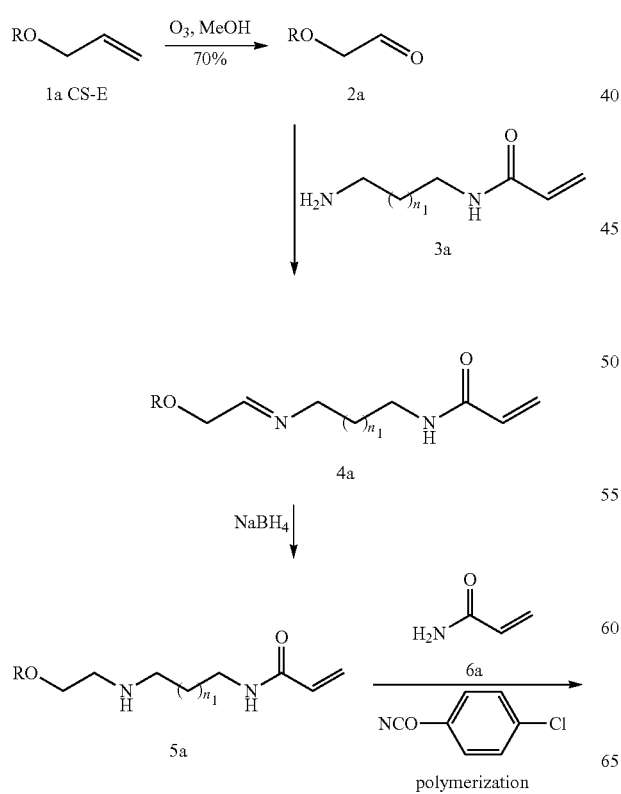

-continued

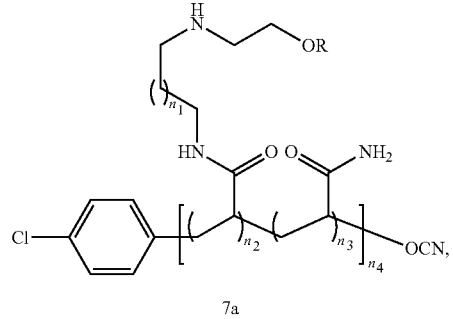

7a

Where the variables are as described elsewhere herein.

b1) Graft conjugation of nucleophilic ligands to poly[(N-acryloxy)succinimide] based on oxide linkers:

Scheme 6:

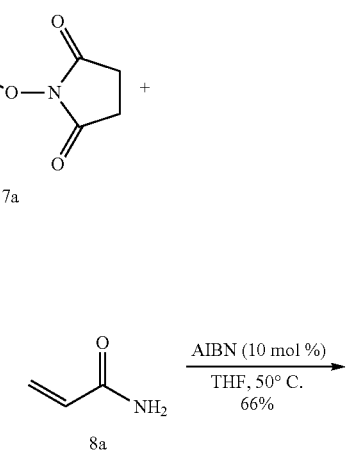

29
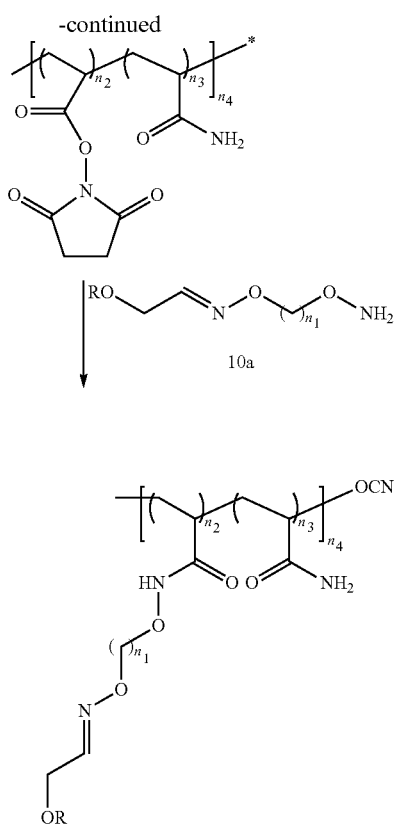
b2) Polyacryamide based polymers based on oxime linkers.
Scheme 7:
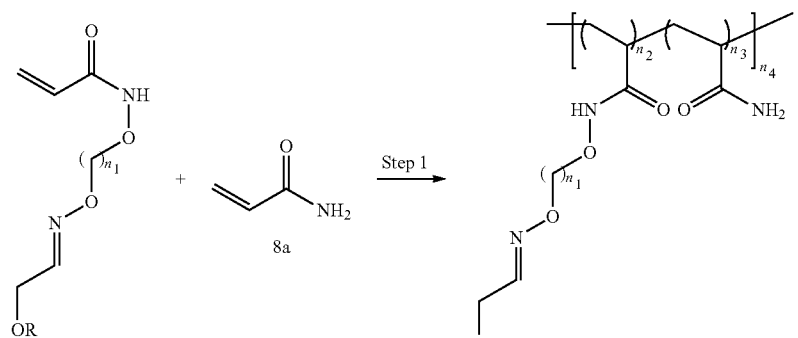
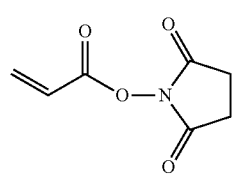
30
c1) Polyacrylamide based polymers based on 2-aminoethanethiol.
Scheme 8:
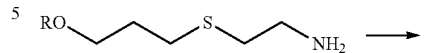
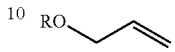
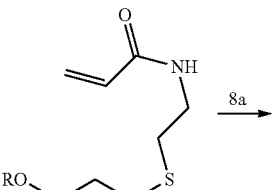
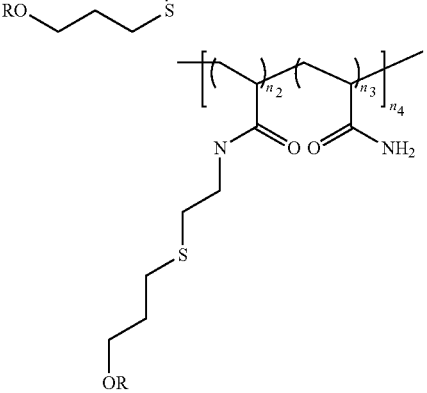

c2) Polyacrylamide based polymers based on 2-aminoethanethiol
Scheme 9:
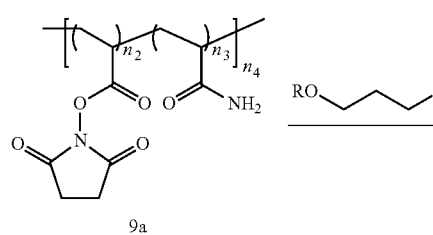
9a
d) Other polyacrylamide based polymers
Scheme 10:
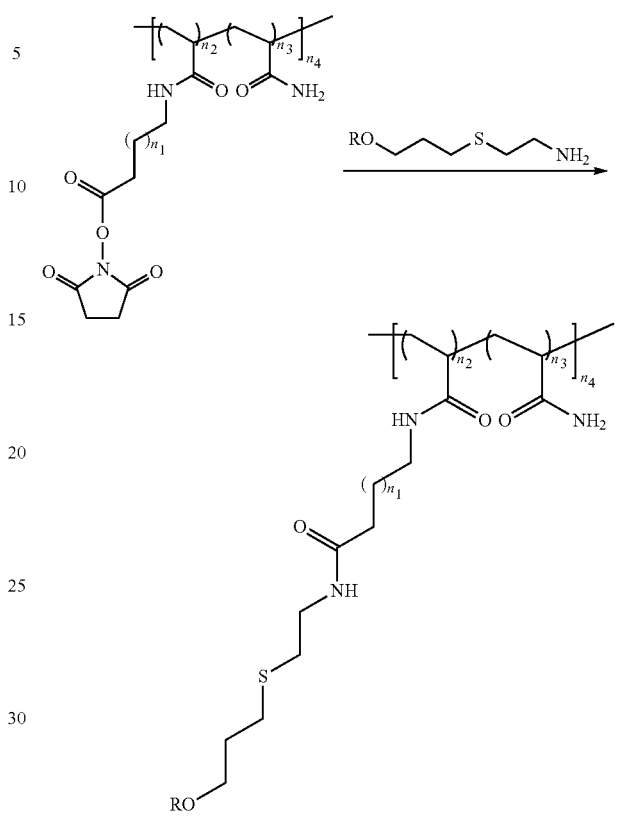
e) Scheme 9 illustrates Grubbs metathesis approach towards glycopolymers with an exemplary compound provided herein
Scheme 11:
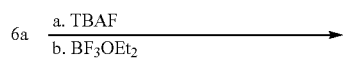
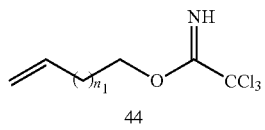
44
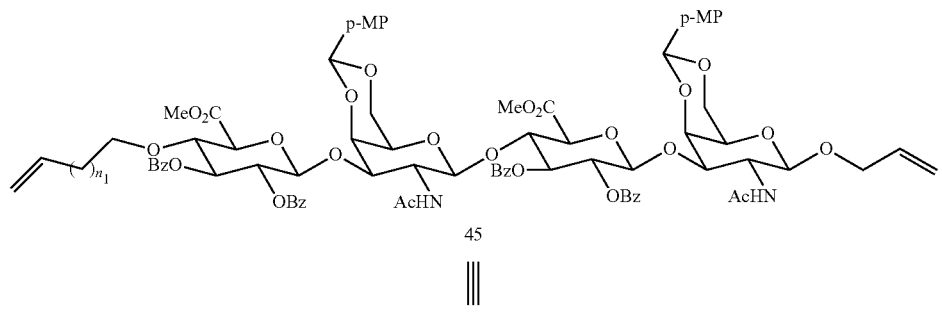
45
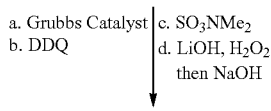
a. Grubbs Catalyst  c. SO₃NMe₂
b. DDQ             d. LiOH, H₂O₂
                      then NaOH -continued

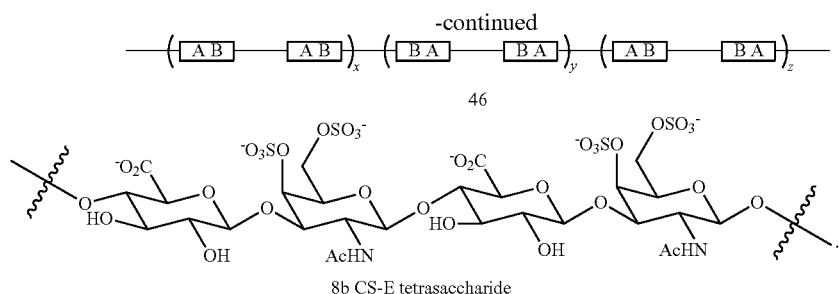

8b CS-E tetrasaccharide
a1 and b1 represent the non-reducing and reducing end of the tetrasaccharide 45
A and B represent the non-reducing and reducing of the tetrasaccharide 8b Synthesis of saccharides linked via linkers provided herein is represented in schemes 10 and 11 as follows:
1. Oxime Linker:

Scheme 12:

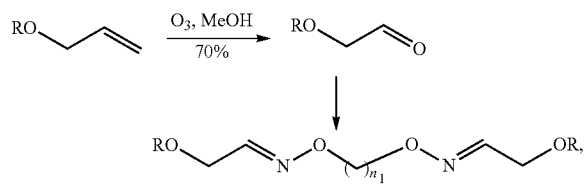

where the variables are as described elsewhere herein.
2. Amine Linker

Scheme 13:

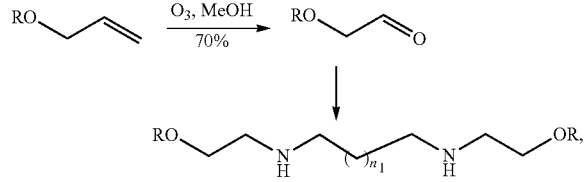

where the variables are as described elsewhere herein.
In certain embodiments, R is

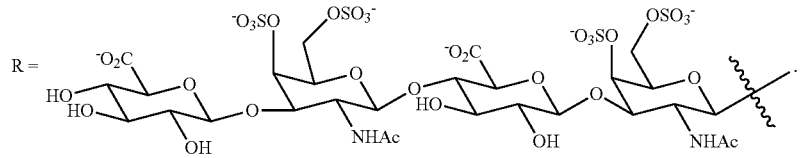

D. Formulation of Pharmaceutical Compositions

The pharmaceutical compositions provided herein contain therapeutically effective amounts of one or more of the compounds provided herein that are useful in the prevention, treatment, or amelioration of one or more of the symptoms associated with neurological disorders and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms associated with neurological disorders. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems well known to those of skill in the art and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms associated with neurological disorders, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included. In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous. If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone.

Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment. The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For nasal administration, the preparation may contain an esterified phosphonate compound dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

These solutions, particularly those intended for ophthalmic use, may be formulated as 0.01%-10% isotonic solutions, pH about 5-7, with appropriate salts.

5. Compositions for other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MDT's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms associated with neurological disorders, within the packaging material, and a label that indicates that the compound or composition, or pharmaceutically acceptable derivative thereof, is used for the treatment, prevention or amelioration of one or more symptoms associated with neurological disorders.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any symptoms associated with neurological disorders.

E. Evaluation of the Activity of the Compounds

The activity of the compounds provided herein can be assessed by methods and assays known to one of skill in the art. For example, the biological activity can be assessed in assays known for testing the activity of chondroitin sulfate.

Figure 1B:
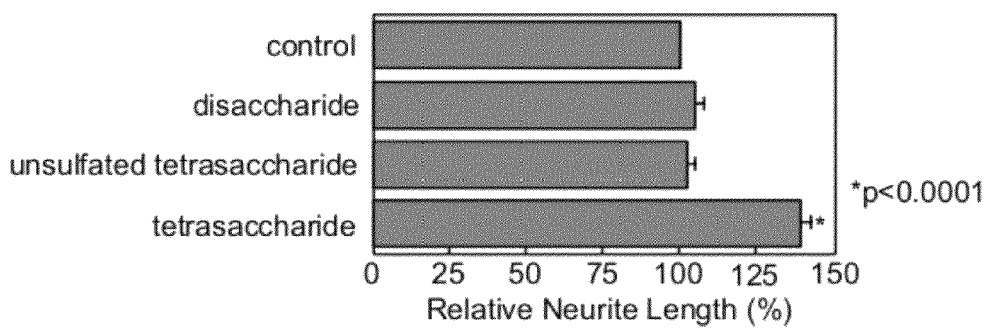
Figure 2A:
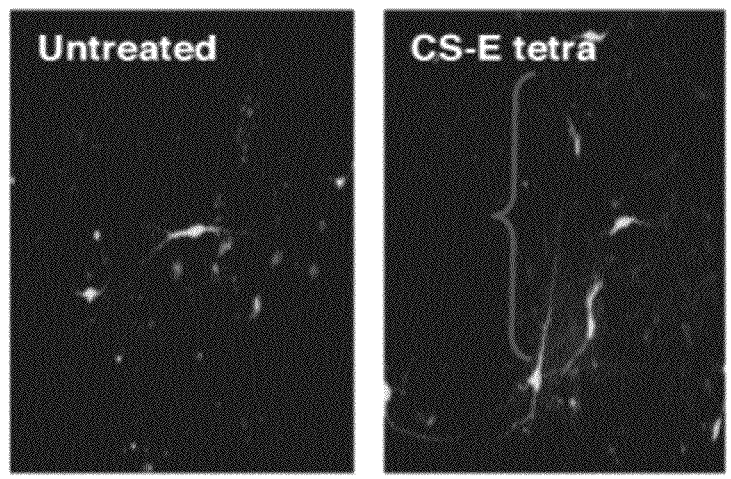
FIGS. 2A-B show the effect of disaccharide CS-E, tetrasaccharide CS-E, and unsulfated tetrasaccharide on the growth of dopaminergic neurons.
Figure 2B:
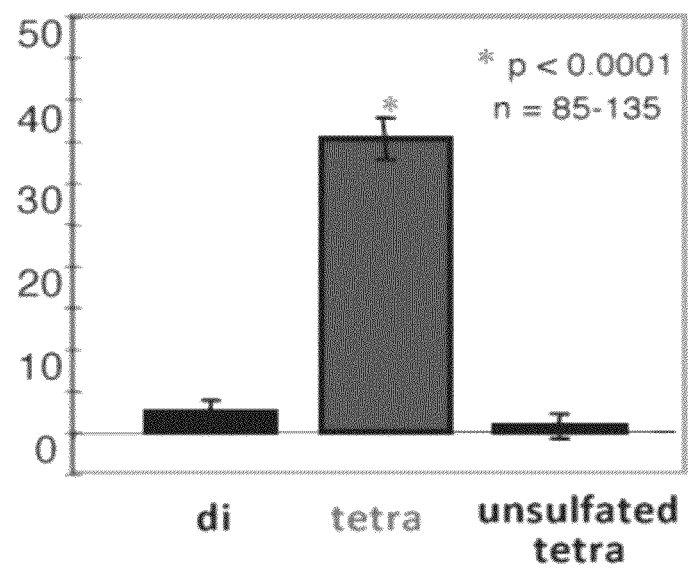
Figure 3A:
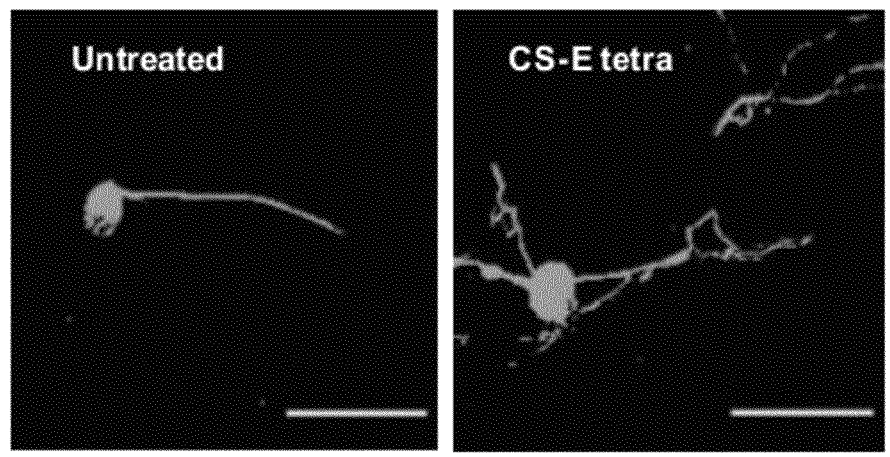
FIGS. 3A-B show the effect of disaccharide CS-E, tetrasaccharide CS-E, and unsulfated tetrasaccharide on the growth of dorsal root ganglion (DRG) neurons from the spinal cord.
Figure 3B:
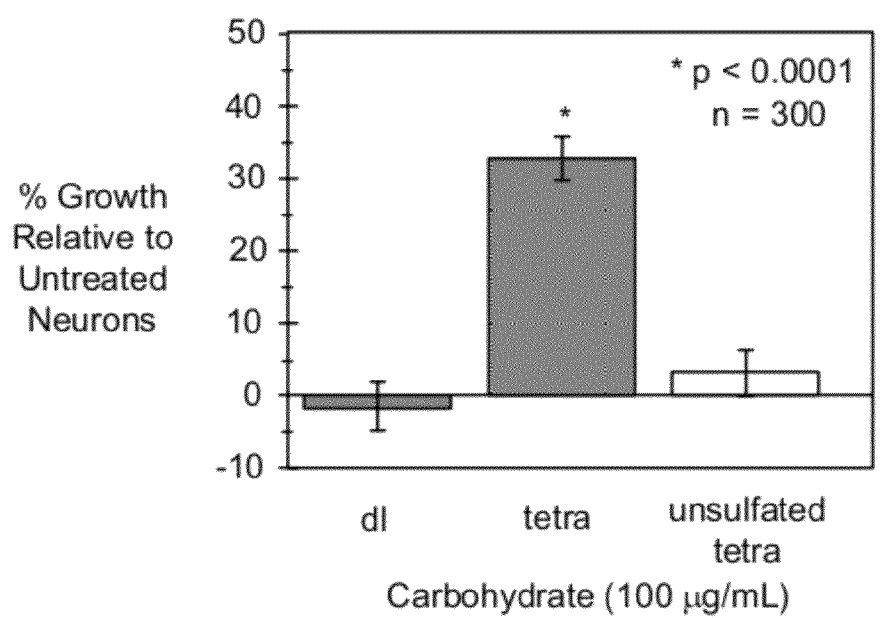
Figure 4:
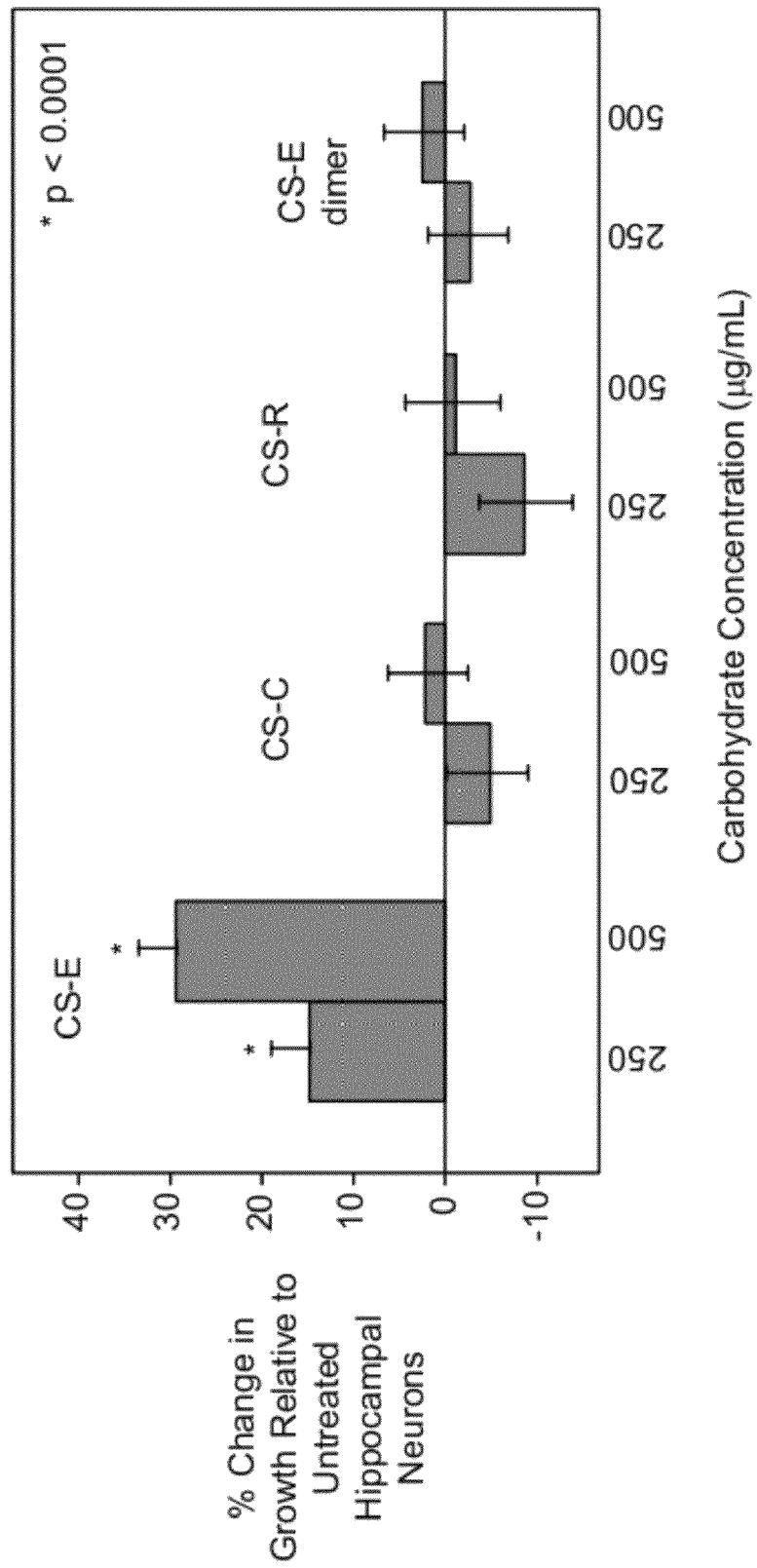
FIG. 4 illustrates the effect of tetrasaccharides CS-E, CS-C, CS-R and CS-E dimer on neuronal growth of hippocampal neuron.

In certain embodiments, the activity of the compounds provided herein to modulate neuronal growth, can be tested using cultured primary hippocampal neurons. Primary hippocampal neurons are cultured on poly-DL-ornithine-coated coverslips with or without each compound. After 48 h, the neurons are fixed, immunostained with anti-tau antibodies, and examined by confocal fluorescence microscopy. The effect of sulfated tetrasaccharide CS-E on neuronal morphology and growth is illustrated in FIGS. 1A-B. The number of neurites emanating from the cell body was enhanced, and the growth of the major extension was stimulated by 39.3±3.6% relative to the poly-DL-ornithine control. In contrast, sulfated disaccharide and unsulfated tetrasaccharide had no significant effect on neuronal outgrowth.

Figure 5:
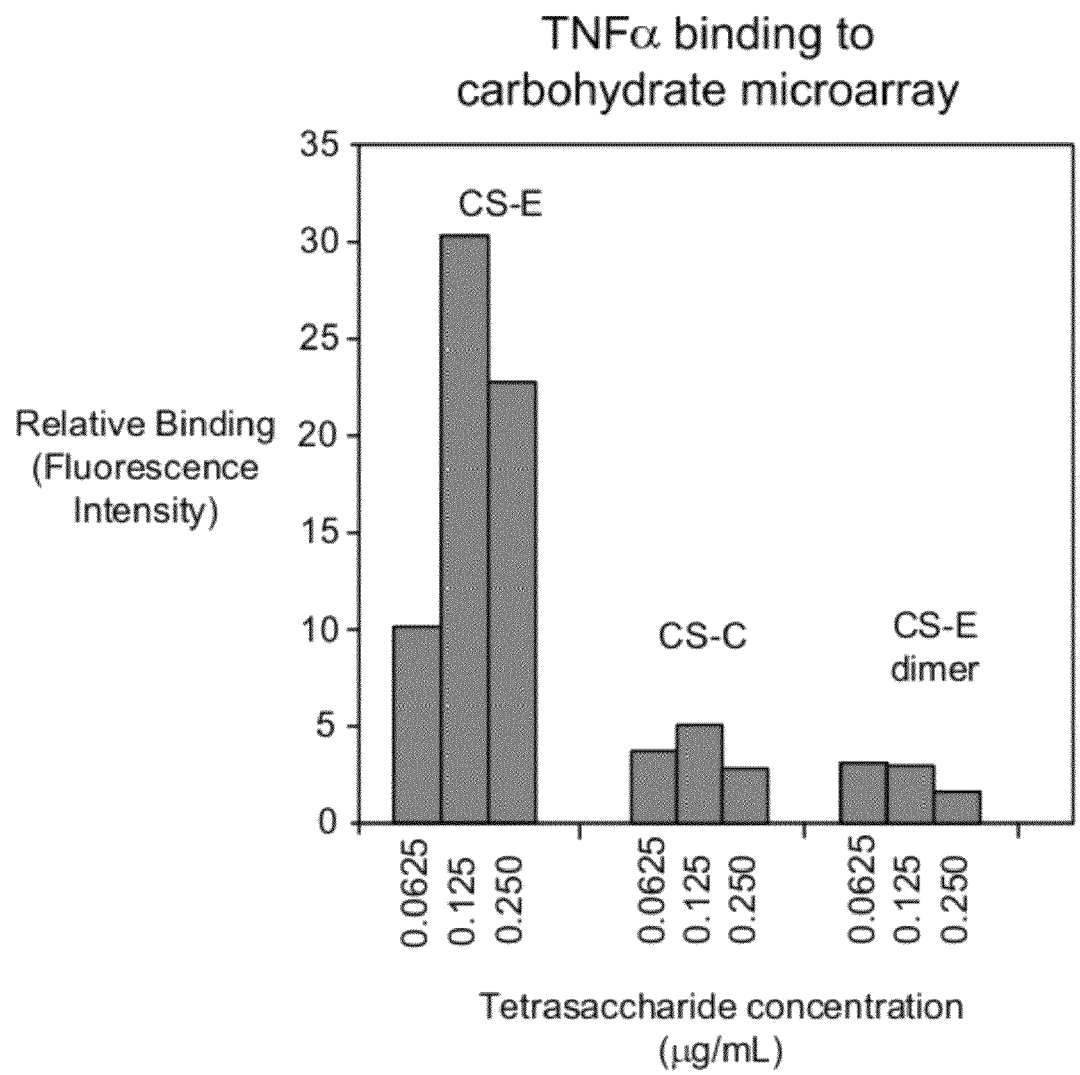
FIG. 5 illustrates binding selectivity of tetrasaccharides CS-E and CS-C, and dimer CS-E to tumor necrosis factor-α.
Figure 6:
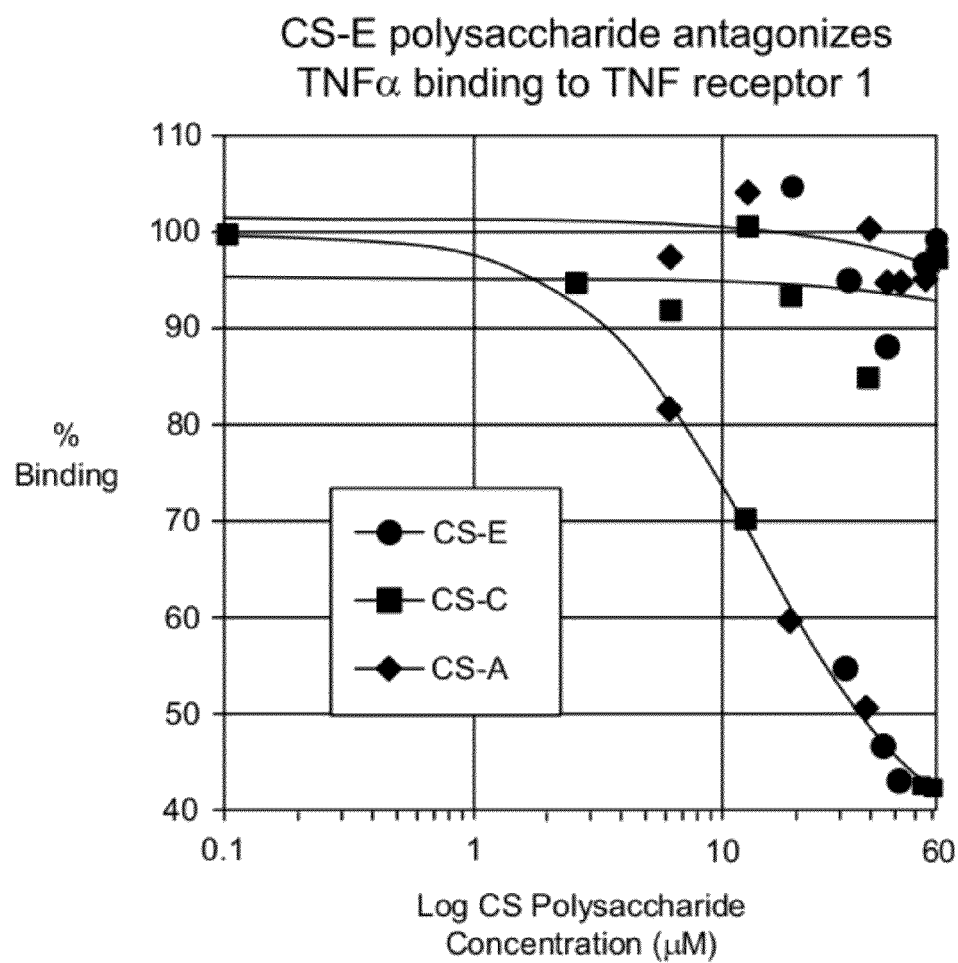
FIG. 6 shows the antagonizing effect of CS polysaccharides enriched in the CS-E, CS-C and CS-A sulfation pattern on binding of TNFα to its receptor, as demonstrated by competition ELISA.
Figure 7:
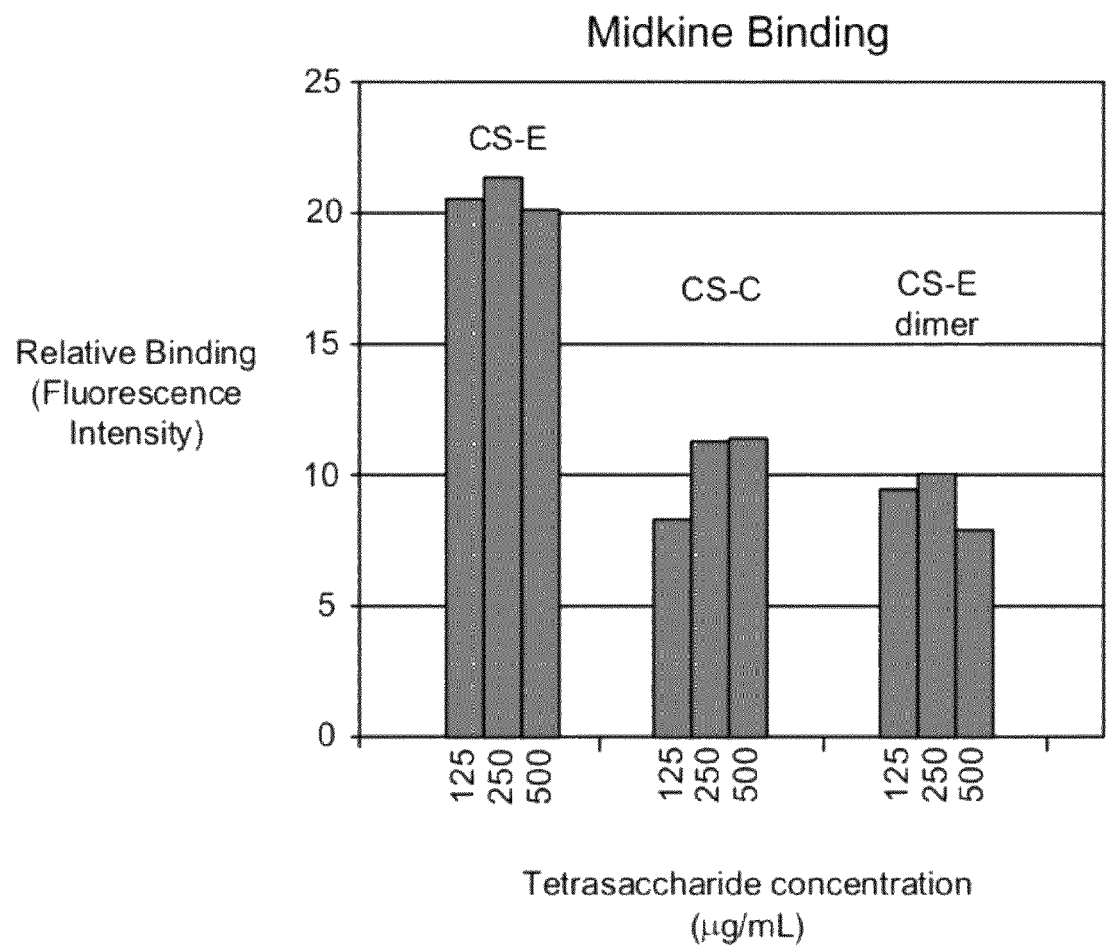
FIG. 7 illustrates binding of tetrasaccharides CS-E, CS-C and disaccharide CS-E to neuronal growth factor midkine.

Effect of disaccharide CS-E, tetrasaccharides CS-E, and unsulfated tetrasaccharide on the growth of dopaminergic neurons as well as dorsal root ganglion (DRG) neurons from the spinal cord is illustrated in FIGS. 2A-B and 4A-B, respectively. In certain embodiments, the CS-E tetrasaccharide promoted the outgrowth of cultured dopaminergic and DRG neurons by 30-40% relative to the untreated controls. FIGS. 5 and 7 illustrate binding of tetrasaccharides CS-E, CS-C and disaccharide CS-E to tumor necrosis factor-α and midkine, respectively.

F. Methods of Use

In one embodiment, the compounds provided herein are useful as modulators of neuronal growth. Thus, provided herein are methods of promoting regeneration of an injured or severed nerve or nerve tissue, or promoting outgrowth in neuronal cells under a variety of neurological conditions requiring neuronal cell outgrowth. The methods include contacting a neuronal cell, or an injured or severed nerve, with a compound provided herein in an amount effective to promote neuronal outgrowth. The method may be carried out in vitro or in vivo.

In certain embodiments, the compounds are used in in vitro studies of neuronal growth. Any of a variety of mammalian neuronal cells, including neuronal cells from brain, CNS, peripheral nerves and the like, can be treated by the methods provided herein. In addition, the cells can be from any of a variety of mammalian species, including human, mouse, chicken, and any other mammalian species, including the agricultural stock and non-domesticated mammals. In certain embodiments, the compounds are used to induce neuronal growth in cultured neurons, including, but not limited to cultured hippocampal neurons, dopaminergic neurons and dorsal root ganglion (DRG) neurons from the spinal cord. In certain embodiments, the compounds provided herein are useful in inducing growth of differentiated neural stem cells prior to implantation. In the case of Parkinson's disease, for instance, implanted tissue has promise as a replacement for dying dopaminergic neurons.

In certain embodiments, the methods provided herein are useful in treating peripheral nerve damage associated with physical or surgical trauma, infarction, bacterial or viral infection, toxin exposure, degenerative disease, malignant disease that affects peripheral or central neurons, or in surgical or transplantation methods in which new neuronal cells from brain, spinal cord or dorsal root ganglia are introduced and require stimulation of neuronal outgrowth from the implant and innervation into the recipient tissue. Such diseases further include but are not limited to CNS lesions, gliosis, Parkinson's disease, Alzheimer's disease, neuronal degeneration, and the like.

In other embodiment, the compounds are used in in vivo applications and as therapeutics for treating a variety of conditions, including, but not limited to neurological disorders resulting from brain disorders or spinal cord trauma. In the case of spinal cord injury, the compounds provided herein, in certain embodiments, assist in the rebuilding of damaged axons.

In certain embodiments, the compounds provided herein modulate the activity of fibroblast growth factors. In other embodiments, the compounds provided herein are used in the treatment of stroke, Parkinson's, and other neurological diseases in conjunction with fibroblast growth factors.

In certain embodiments, the compounds provided herein are administered in combination with proteins that either induce neuronal growth or inhibit neuronal growth. In certain embodiments, the compounds provided herein are used to stimulate the growth of an implanted tissue, in conjunction with proteins or other factors that stimulate the growth. In certain embodiments, the compounds provided herein are administered in combination with tumor necrosis factor-α or TNFα and nerve growth factor or NGF. In certain embodiments, the compounds provided herein interact with growth factors and cytokines (e.g., tumor necrosis factor-α or TNFα and nerve growth factor or NGF).

In certain embodiments, provided herein are methods of screening for small molecule inducers of neuronal growth. The methods involve applying to a cultured neuron a small molecule bearing a plurality of negatively charged groups, and determining the increase in axon length of a treated versus an untreated cell. The compounds provided herein, in certain embodiments, cause an increase in mean axon length relative to an untreated cell between about 1 to about 50%. In certain embodiments, the increase in mean axon length caused by the compounds provided herein is greater than about 1%, about 5%, about 10%, about 15%, about 20%, about 25%, about 30%, about 35%, about 40%, about 45% or about 50%. In certain embodiments, the increase in mean axon length is greater than about 10%, in other embodiment, greater than 20% and in another embodiment, greater than 30% relative to an untreated cell.

The following examples are provided for illustrative purposes only and are not intended to limit the scope of the invention.

EXAMPLES

General Methods and Experimental Details

Unless stated otherwise, reactions were performed in flame-dried glassware under a nitrogen or an argon environment, using freshly distilled solvents. All other commercially obtained reagents were used as received. Thin-layer chromatography (TLC) was performed using E. Merck silica gel 60 F254 precoated plates (0.25 mm). Visualization of the developed chromatogram was performed by fluorescence quenching, cerium ammonium molybdate stain, or ninhydrin stain as necessary. ICN silica gel (particle size 0.032-0.063 mm) was used for flash chromatography. Gel filtration chromatography (Sephadex® G-10 and G-25 ultrafine) was used in order to achieve purification of the final products.

$^1$H NMR and proton decoupling experiments were recorded on Varian Mercury 300 (300 MHz) and Varian Mercury 600 (600 MHz) spectrometers and are reported in parts per million (δ) relative to Me$_4$Si (0.0 ppm). Data for $^1$H are reported as follows: chemical shift (δ ppm), multiplicity (s=singlet, d=doublet, t=triplet, q=quartet, m=multiplet), coupling constant in Hz, and integration. $^{13}$C NMR spectra were obtained on a Varian Mercury 300 (75 MHz) spectrometer and are reported in terms of chemical shift. IR spectra were recorded on a Perkin Elmer Paragon 1000 spectrometer and are reported in terms of frequency of absorption (cm$^{-1}$).

Example 1

A). Synthesis of the Glucuronic Acid Monomer 5

A1) p-Methylphenyl 4,6-O-p-methoxybenzylidene-1-thio-β-D-glucopyranoside (2'). The procedure for the preparation of 2' was adapted from Ye et al. (Ye, X.-S.; Wong, C.-H. *J. Org. Chem.* 2000, 65, 2410-2431) p-Methylphenyl-1-thio-β-D-glucopyranoside (Clingman, A. L.; Richtmyer, N. K. *J. Org. Chem.* 1964, 29, 1782-1787) 1' (36.7 g, 128 mmol) was dissolved in DMF (30.0 mL) and $CH_3CN$ (300 mL). p-Anisaldehyde dimethyl acetal (44.0 mL, 256 mmol) and DL-10-camphorsulfonic acid (6.00 g, 25.6 mmol) were added. The reaction was stirred at rt for 12 h. The reaction was quenched with TEA and concentrated to afford an orange syrup. The product was purified by flash chromatography (50%→70% EtOAc:hexanes) to afford 2' (36.3 g, 70%) as a white crystalline solid. $R_f$ 0.26 (50% EtOAc:hexanes). $[\alpha]_D^{21}$=−38 (c=1.0, $CH_2Cl_2$); IR (thin film on NaCl): ν=3447, 2869, 1614, 1518, 1250, 1104, 1084, 1033 $cm^{-1}$; $^1$H NMR (300 MHz, $CDCl_3$): δ=7.43 (d, J=8.1 Hz, 2H, $SC_6H_4Me$), 7.39 (d, J=9.0 Hz, 2H, $C_6H_4OMe$), 7.15 (d, J=7.5 Hz, 2H, $SC_6H_4Me$), 6.88 (d, J=9.0 Hz, 2H, $C_6H_4OMe$), 5.48 (s, 1H, MeOPhCH), 4.56 (d, J=9.9 Hz, 1H, H-1), 4.35 (dd, J=3.9, 10.5 Hz, 1H), 3.85-3.72 (m, 5H), 3.50-3.39 (m, 3H), 2.80 (br s, 1H, OH), 2.67 (br s, 1H, OH), 2.36 (s, 3H, $SPhCH_3$); $^{13}$C NMR (75 MHz, $CDCl_3$): δ=138.8, 138.2, 133.6, 132.1, 129.9, 129.4, 127.7, 113.7, 101.8, 88.7, 80.2, 74.5, 72.5, 70.5, 68.6, 55.3, 21.2; FAB MS: m/z: calcd for $C_{21}H_{25}O_6S$: 405.1372. found: 405.1359 $[M+H]^+$.

A2) p-Methylphenyl 2,3-di-O-benzoyl-4,6-O-p-methoxybenzylidene-1-thio-β-D-glucopyranoside (3'). 2' (23.7 g, 58.6 mmol) was dissolved in $CH_2Cl_2$ (670 mL). In a separate flask, benzoyl chloride (17.0 mL, 146 mmol) was added dropwise to a solution of 4-(dimethylamino)pyridine (DMAP, 25.1 g, 205 mmol) in $CH_2Cl_2$ (225 mL). The benzoyl chloride/DMAP solution was then slowly added to the solution of 2'. An additional volume of $CH_2Cl_2$ (19.0 mL) was used to complete the transfer of solution. The reaction was allowed to stir at rt for 25 min and then quenched with saturated aqueous $NaHCO_3$. The aqueous layer was extracted with $CH_2Cl_2$ (2×). The combined organic layers were washed with brine, dried over $Na_2SO_4$, filtered, and concentrated to yield a pale yellow solid. This crude material was washed with MeOH and crystallization from EtOAc afforded 3' as a white solid (30.8 g, 86%). $R_f$ 0.43 (30% EtOAc:hexanes). $[\alpha]_D^{22}$=+25 (c=0.42, $CH_2Cl_2$); IR (thin film on NaCl): ν=2934, 1740, 1735, 1730, 1715, 1700, 1617, 1614, 1517, 1272, 1251, 1095 $cm^{-1}$; $^1$H NMR (300 MHz, $CDCl_3$): δ=7.98-7.90 (m, 4H, ArH), 7.56-7.30 (m, 10H, ArH), 7.12 (d, J=8.1 Hz, 2H, $SC_6H_4Me$), 6.82 (d, J—, 8.7 Hz, 2H, $C_6H_4OMe$), 5.76 (dd, J=9.3, 9.3 Hz, 1H, H-3), 5.49 (s, 1H, MeOPhCH), 5.43 (dd, J=9.3, 9.3 Hz, 1H, H-2), 4.95 (d, J=10.5 Hz, 1H, H-1), 4.43 (dd, J=4.5, 10.8 Hz, 1H), 3.90-3.82 (m, 2H), 3.76-3.67 (m, 4H), 2.35 (s, 3H, $SPhCH_3$); $^{13}$C NMR (75 MHz, $CDCl_3$): δ=165.6, 165.2, 160.1, 138.8, 133.8, 133.3, 133.1, 129.9, 129.8, 129.8, 129.4, 129.3, 129.2, 128.4, 128.3, 127.9, 127.5, 113.6, 101.5, 87.3, 78.5, 73.4, 71.1, 71.0, 68.5, 55.3, 21.3; FAB MS: m/z: calcd for $C_{35}H_{33}O_8S$: 613.1896. found: 613.1879 $[M+H]^+$.

A3) p-Methylphenyl 2,3-di-O-benzoyl-4-O-tert-butyldimethylsilyl-6-O-p-methoxybenzyl-1-thio-β-D-glucopyranoside (4'). The procedure for the regioselective ring opening of 3' was adapted from Johansson et al. (Johansson, R.; Samuelsson, B. *J. Chem. Soc, Perkin Trans.* 1 1984, 2371-2374) 3' (12.0 g, 19.6 mmol) was combined with sodium cyanoborohydride (6.15 g, 97.9 mmol), activated 3 Å powdered molecular sieves (12.0 g), and dissolved in DMF (261 mL). The reaction was cooled to 0° C. Trifluoroacetic acid (15.3 mL, 196 mmol) was added dropwise to the reaction. The reaction was stirred at 0° C. for 1 h, and then allowed to warm to rt. The reaction stirred at rt for 1 d. It was then filtered, diluted with $CH_2Cl_2$, and quenched with cold saturated aqueous $NaHCO_3$. The aqueous layer was separated and extracted with $CH_2Cl_2$ (2×). The combined organic layers were washed with saturated aqueous $NaHCO_3$ (1×) and brine (1×), dried over $Na_2SO_4$, filtered, and concentrated. To remove the remaining sodium cyanoborohydride, the crude material was re-dissolved in $CH_2Cl_2$ (250 mL) and washed with brine (3×). The organic layer was dried over $Na_2SO_4$, filtered, and concentrated to afford a white solid containing the desired alcohol. $R_f$ 0.23 (30% EtOAc:hexanes).

The crude alcohol was dissolved in $CH_2Cl_2$ (476 mL), TEA (8.20 mL, 58.6 mmol) was added, and the reaction cooled to 0° C. tert-Butyldimethylsilyl trifluoromethanesulfonate (11.2 mL, 48.8 mmol) was added dropwise to the reaction. The reaction was allowed to warm to rt and stirred for 3 h. It was then quenched with saturated aqueous $NaHCO_3$ and diluted with $CH_2Cl_2$. The aqueous layer was separated and extracted with $CH_2Cl_2$ (3×). The combined organic layers were washed with brine, dried over $Na_2SO_4$, filtered, and concentrated to afford an orange syrup. The product was purified by flash chromatography (10%→12% EtOAc:hexanes) to afford 4' (13.2 g, 94%) as a white foam. $R_f$ 0.64 (30% EtEtOAc:hexanes). $[\alpha]_D^{22}$=+36 (c=1.0, $CH_2Cl_2$); IR (thin film on NaCl): ν=2953, 2928, 2856, 1734, 1612, 1602, 1513, 1451, 1272, 1251, 1106, 1089, 1069 $cm^{-1}$; $^1$H NMR (300 MHz, $CDCl_3$): δ=7.92-7.87 (m, 4H, ArH), 7.51-7.27 (m, 10H, ArH), 7.03 (d, J=7.8 Hz, 21-1, $SC_6H_4Me$), 6.94-6.91 (m, 2H, ArH), 5.59 (dd, J=9.2, 9.2 Hz, 1H, H-3), 5.30 (dd, J=9.6, 9.6 Hz, 1H, H-2), 4.88 (d, J=9.6 Hz, 1H, H-1), 4.60 (d, J=11.4 Hz, 1H, $CH_2PhOMe$), 4.51 (d, J=11.7 Hz, 1H, $CH_2PhOMe$), 4.01 (dd, J=9.0, 9.0 Hz, 1H, H-4), 3.84-3.64 (m, 6H, H-5, 11-6, H-6, $PhOCH_3$), 2.32 (s, 3H, $SPhCH_3$), 0.74 (s, 9H, $(CH_3)_3CSi$), 0.02 (s, 3H, $CH_3Si$), −0.22 (s, 3H, $CH_3Si$); $^{13}$C NMR (75 MHz, $CDCl_3$): δ=165.9, 165.3, 159.2, 138.2, 133.4, 133.1, 133.0, 130.5, 129.9, 129.9, 129.8, 129.7, 129.5, 129.3, 128.6, 128.4, 128.3, 113.9, 86.1, 81.0, 77.5, 73.3, 71.3, 69.4, 68.7, 55.5, 25.9, 21.5, 18.1, −3.9, −4.4; FAB MS: m/z: calcd for $C_{41}H_{47}O_8SSi$: 727.2785. found: 727.2761 $[M]^+$.

A4) p-Methylphenyl 2,3-di-O-benzoyl-4-O-tert-butyldimethylsilyl-1-thio-β-D-glucopyranoside (5'). In a flask covered with aluminum foil, 4' (13.2 g, 18.1 mmol) was dissolved in $CH_2Cl_2$ (440 mL). Water (23.0 mL) and 2,3-dichloro-5,6-dicyano-1,4-benzoquinone (4.93 g, 21.7 mmol) were added. The reaction was stirred at rt for 13 h. The reaction was then quenched with aqueous $NaHCO_3$, and water was added to dissolve all solids. The aqueous layer was separated and extracted with $CH_2Cl_2$ (3×). The combined organic layers were washed with brine, dried over $Na_2SO_4$, filtered, and concentrated to yield a peach solid. The product was purified by flash chromatography (40% $CH_2Cl_2$:hexanes→100% $CH_2Cl_2$→10% EtOAc: $CH_2Cl_2$) to afford 5' (9.42 g, 86%) as a white foam. $R_f$ 0.41 (20% EtOAc:hexanes). $[\alpha]_D^{22}$=+62 (c=1.0, $CH_2Cl_2$); IR (thin film on NaCl): ν=3442, 2951, 2928, 2856, 1733, 1602, 1493, 1451, 1273, 1088, 1070, 1027 $cm^{-1}$; $^1$H NMR (300 MHz, $CDCl_3$): δ=7.92-7.88 (m, 4H, ArH), 7.52-7.45 (m, 2H, ArH), 7.38-7.32 (m, 6H, ArH), 7.12 (d, J=8.1 Hz, 2H, $SC_6H_4Me$), 5.62 (dd, J=9.3, 9.3 Hz, 1H, H-3), 5.29 (dd, J=9.6, 9.6 Hz, 1H, H-2), 4.93 (d, J=9.9 Hz, 1H, H-1), 4.02-3.92 (m, 2H), 3.81-3.73 (m, 1H), 3.60-3.55 (d, J=11.4 Hz, 1H), 2.35 (s, 3H, SPhCH$_3$), 1.95 (br s, 1H, OH), 0.76 (s, 9H, (CH$_3$)$_3$CSi), 0.07 (s, 3H, CH$_3$Si), −0.20 (s, 3H, CH$_3$Si); $^{13}$C NMR (75 MHz, CDCl$_3$): δ=165.9, 165.4, 138.7, 133.5, 133.3, 133.2, 130.0, 130.0, 129.9, 129.8, 129.4, 128.5, 128.5, 128.4, 86.4, 81.1, 77.2, 71.3, 69.0, 62.0, 25.9, 21.6, 18.2, −3.9, −4.3; FAB MS: m/z: calcd for C$_{33}$H$_{41}$O$_7$SSi: 609.2342. found: 609.2321 [M+H]$^+$.

A5) p-Methylphenyl (methyl 2,3-di-O-benzoyl-4-O-tert-butyldimethylsilyl-1-thio-β-D-glucopyranosyluronate (6'). 5' (9.42 g, 15.5 mmol) was dissolved in DMF (115 mL). Pyridinium dichromate (34.9 g, 92.8 mmol) was added, and the reaction was stirred at rt for 3 d. To precipitate and remove the chromium salts, EtOAc was added, and the reaction was filtered and concentrated (3×). The remaining salts were removed by flash chromatography (100% EtOAc) to yield a white foam containing the desired carboxylic acid. R$_f$ 0.17 (30% EtOAc:hexanes).

The crude acid was dissolved in CH$_2$Cl$_2$ (187 mL) and cooled to 0° C. Diazomethane (93.0 mL, 0.2 M in diethyl ether, 18.6 mmol) was slowly added. The reaction stirred at 0° C. for 1 h. Glacial acetic acid was added to quench the reaction. It was then concentrated and purified by flash chromatography (10%→15% EtOAc:hexanes) to yield 6' (6.04 g, 61%) as a white solid. R$_f$ 0.67 (30% EtOAc:hexanes). [α]$_D^{22}$=+54 (c=1.0, CH$_2$Cl$_2$); IR (thin film on NaCl): ν=3443, 2953, 2928, 2857, 1732, 1601, 1493, 1451, 1437, 1269, 1085, 1069 cm$^{-1}$; $^1$H NMR (300 MHz, CDCl$_3$): δ=7.90-7.86 (m, 4H, ArH), 7.52-7.46 (m, 2H, ArH), 7.38-7.31 (m, 6H, ArH), 7.10 (d, J=8.1 Hz, 2H, SC$_6$H$_4$Me), 5.59 (dd, J=9.3, 9.3 Hz, 1H, H-3), 5.30 (dd, J=9.6, 9.6 Hz, 1H, H-2), 4.90 (d, J=9.9 Hz, 1H, H-1), 4.26 (dd, J=9.2, 9.2 Hz, 1H, H-4), 4.08 (d, J=8.7 Hz, 1H, H-5), 3.82 (s, 31-1, CO$_2$CH$_3$), 2.33 (s, 3H, SPhCH$_3$), 0.71 (s, 9H, (CH$_3$)$_3$CSi), −0.05 (s, 3H, CH$_3$Si), −0.22 (s, 3H, CH$_3$Si); $^{13}$C NMR (75 MHz, CDCl$_3$): δ=168.3, 168.3, 165.9, 165.3, 138.8, 133.7, 133.4, 133.4, 130.0, 130.0, 130.0, 129.7, 129.5, 128.5, 128.2, 87.2, 80.4, 76.6, 70.9, 70.7, 52.8, 25.6, 21.4, 18.0, −4.2, −4.9; FAB MS: m/z: calcd for C$_{34}$H$_{41}$O$_8$SSi: 637.2291. found: 637.2284 [M+H]

A6) Methyl 2,3-di-O-benzoyl-4-O-tert-butyldimethylsilyl-α/β-D-glucopyranosyluronate (7'). 6' (6.09 g, 9.56 mmol) was dissolved in CH$_2$Cl$_2$ (67.0 mL) and water (0.700 mL) was added. A solution was prepared containing 2.93 g N-iodosuccinimide, 127 mL CH$_2$Cl$_2$, 3.10 mL THF, and 78.0 μL triflic acid. 130 mL of this solution was added to the reaction mixture. The reaction stirred at rt. for 5.5 h. It was then quenched with 1 M Na$_2$S$_2$O$_3$ and diluted with CH$_2$Cl$_2$. The aqueous layer was separated and extracted with CH$_2$Cl$_2$ (3×). The combined organic layers were washed with brine, dried over Na$_2$SO$_4$, filtered, and concentrated. The product was purified by flash chromatography (15%→30% EtOAc:hexanes) to afford 7' (4.27 g, 84%, 6.2β:1α) as a white foam. R$_f$ 0.30, 0.36 (30% EtOAc:hexanes). [α]$_D^{22}$=+99 (c=1.0, CH$_2$Cl$_2$); IR (thin film on NaCl): ν=3455, 2954, 2930, 2857, 1732, 1602, 1451, 1275, 1110, 1070 cm$^{-1}$; $^1$H NMR (300 MHz, CDCl$_3$): δ=8.18-8.07 (m, 4H, ArH), 7.99-7.90 (m, 4H, ArH), 7.69-7.31 (m, 12H, ArH), 6.55 (d, J=3.3 Hz, 1H, H-1, α), 5.94 (dd, J=9.0, 9.9 Hz, 1H), 5.72-5.58 (m, 3H), 5.22-5.14 (m, 2H), 4.62 (d, J=9.3 Hz, 1H, H-1, β), 4.40-4.27 (m, 2H), 4.13 (d, J=9.3 Hz, 1H), 3.81 (s, 3H, CO$_2$CH$_3$), 3.80 (s, 3H, CO$_2$CH$_3$), 3.46 (d, J=3.6 Hz, 1H), 0.76 (s, 9H, (CH$_3$)$_3$CSi), 0.75 (s, 9H, (CH$_3$)$_3$CSi), −0.01 (s, 6H, CH$_3$Si), −0.15 (s, 6H, CH$_3$Si); $^{13}$C NMR (75 MHz, CDCl$_3$): δ=169.8, 169.0, 168.7, 167.4, 167.3, 166.1, 165.9, 165.0, 134.2, 133.9, 133.8, 133.6, 133.4, 130.3, 130.2, 130.1, 129.9, 129.1, 129.0, 128.8, 128.6, 128.6, 92.2, 90.9, 75.8, 74.8, 74.6, 74.6, 72.5, 72.4, 72.3, 71.1, 70.5, 70.2, 52.9, 25.7, 25.6, 18.0, −4.2, −4.9; FAB MS: m/z: calcd for C$_{27}$H$_{35}$O$_9$Si: 531.2050. found: 531.2041 [M+H]$^+$.

A7) Methyl 2,3-di-O-benzoyl-4-O-tert-butyldimethylsilyl-α-D-glucopyranosyluronate trichloroacetimidate (5). The preparation of 5 was performed by using a procedure modified from Driguez et. al. (Driguez, P.-A.; Lederman, I.; Strassel, J.-M.; Herbert, J.-M.; Petitou, M. J. Org. Chem. 1999, 64, 9512-9520) 7' (3.32 g, 6.26 mmol) was coevaporated with toluene (2×20 mL) and dried under vacuum overnight. It was then dissolved in CH$_2$Cl$_2$ (49.0 mL). Trichloroacetonitrile (3.80 mL, 37.5 mmol) and Cs$_2$CO$_3$ (0.820 g, 2.50 mmol) were added. After stirring at rt for 4 h, additional trichloroacetonitrile (0.950 mL, 9.50 mmol) and Cs$_2$CO$_3$ (0.200 g, 0.600 mmol) were added. The reaction was allowed to stir an additional 4 h and then concentrated. The product was purified by flash chromatography (10% EtOAc:hexanes+ 0.1% TEA) to afford 5 (3.77 g, 89%), with a trace amount of the 13 anomer, as a white foam. R$_f$ 0.57 (30% EtOAc:hexanes). [α]$_D^{22}$=+99 (c=1.0, CH$_2$Cl$_2$); IR (thin film on NaCl): ν=3343, 2954, 2930, 2858, 1757, 1735, 1676, 1602, 1451, 1315, 1267, 1111, 1095 cm$^{-1}$; $^1$H NMR (300 MHz, CDCl$_3$): δ=8.60 (s, 1H, C=NH), 7.96-7.87 (m, 4H, ArH), 7.53-7.29 (m, 6H, ArH), 6.74 (d, J=3.9 Hz, 1H, H-1), 5.99 (dd, J=9.0, 10.2 Hz, 1H, H-3), 5.43 (dd, J=3.9, 10.5 Hz, 1H, H-2), 4.51 (d, J=9.3 Hz, 1H, H-5), 4.38 (dd, J=9.3, 9.3 Hz, 1H, H-4), 3.81 (s, 3H, CO$_2$CH$_3$), 0.74 (s, 9H, (CH$_3$)$_3$CSi), −0.01 (s, 3H, CH$_3$Si), −0.15 (s, 3H, CH$_3$Si); $^{13}$C NMR (75 MHz, CDCl$_3$): δ=168.7, 165.7, 165.7, 160.8, 133.7, 133.5, 130.1, 129.9, 129.7, 128.7, 128.6, 128.6, 93.4, 74.6, 72.5, 70.9, 70.8, 53.0, 53.0, 25.7, 18.0, −4.1, −4.9; ESI MS: m/z: calcd for C$_{29}$H$_{34}$Cl$_3$NNaO$_9$Si: 696.1. found: 696.2 [M+Na]$^+$.

B) Synthesis of the Galactosamine Monomer 6

B1) 1,3,4,6-tetra-O-acetyl-2-deoxy-2-trichloroacetamido-α/β-D-galactopyranoside (9'). 1,3,4,6-tetra-O-acetyl-2-azido-2-deoxy-D-galactopyranoside (Lemieux, R. U.; Ratcliffe, R. M. Can. J. Chem. —Rev. Can. Chim. 1979, 57, 1244-1251) 8' (0.100 g, 0.268 mmol) in THF (5.00 mL), was added p-tosic acid monohydrate (0.051 g, 0.27 mmol) followed by Pd/C (0.017 g, 6 mol %). The reaction was then placed under an atmosphere of H$_2$ and stirred at rt for 18 h. The Pd/C was removed by filtration through Celite and the solvent concentrated to afford an anomeric mixture of crude amines as a pale yellow foam. The crude mixture was used for the next step without purification. To a solution of crude amines in THF (5 mL), cooled to 0° C. was added trichloroacetylchloride (0.220 g, 1.21 mmol, 0.130 mL) followed by TEA (0.180 g, 1.79 mmol, 0.250 mL). The reaction mixture was stirred at 0° C. for 15 min and then quenched with saturated aqueous NaHCO$_3$. The water layer was separated and extracted with CH$_2$Cl$_2$ (2×) and the combined organics dried over Na$_2$SO$_4$ and the solvent removed in vacuo to afford a yellow oil. Purification of this oil by flash chromatography (30%→40% EtOAc:hexanes) afforded 9' (0.099 g, 75%, 3.1β:1α) as a white solid R$_f$ 0.61 and 0.53 (60% EtOAc: hexanes). $^1$H NMR (300 MHz, CDCl$_3$): δ=6.73 (d, J=9.0 Hz, 2H, NH), 6.30 (d, J=3.9 Hz, 1H, H-1, a), 5.45 (d, J=3.3 Hz, 3H), 5.32 (dd, J=3.5 Hz and 11.3 Hz, 2H), 4.58 (m, 2H), 4.26 (dd, J=6.6 Hz, 6.6 Hz, 2H), 4.20-4.03 (m, 4H), 2.17 (s, 6H), 2.15 (s, 6H), 2.02 (s, 6H), 2.00 (s, 6H); $^{13}$C NMR (75 MHz, CDCl$_3$): δ=171.2, 170.5, 170.2, 168.7, 162.2, 90.5, 69.0, 67.8, 66.8, 61.5, 49.6, 21.2, 21.0; ESI MS: m/z: calcd for C$_{16}$H$_{19}$C$_{13}$NO$_{10}$: 490.0075. found: 490 [M−H]$^-$.

B2) p-Methylphenyl 2-deoxy-2-trichloroacetamido-3,4,6-tri-O-acetyl-1-thio-β-D-galactopyranoside (10'). To a solution of 9' (0.050 g, 0.10 mmol) in dry CH$_2$Cl$_2$ (0.35 mL) was added p-toluenethiol (0.042 g, 0.34 mmol) followed by $BF_3 \cdot OEt_2$ (0.043 g, 0.30 mmol, 38 μL) and the reaction mixture stirred at rt. After 2 h, a further addition of p-toluenethiol (0.012 g, 0.10 mmol) and $BF_3 \cdot OEt_2$ (0.014 g, 0.10 mmol, 13 μL) was made followed by stirring at rt for 1 h. The reaction mixture was quenched with saturated aqueous $NaHCO_3$ and the organic phase washed twice with saturated aqueous $NaHCO_3$ and water. The aqueous layers were back extracted with $CH_2Cl_2$ (3×) and the combined organics washed with brine and dried over $Na_2SO_4$ to afford an amber oil. Purification of this oil by flash chromatography (20%→25% EtOAc:hexanes) afforded 10' (0.044 g, 80%) as a white solid. $R_f$ 0.51 (50% EtOAc:hexanes). $[\alpha]_D^{23}=-2.4$ (c=0.5, $CH_2Cl_2$); IR (thin film on NaCl): ν=3450, 1752, 1655, 1529, 1493, 1370, 1230, 1082, 1045 cm$^{-1}$; $^1$H NMR (300 MHz, CDCl$_3$): δ=7.42 (d, J=8.3 Hz, 2H, SC$_6$H$_4$Me), 7.12 (d, J=8.3 Hz, 2H, SC$_6$H$_4$Me), 6.77 (d, J=8.7 Hz, 1H, NH), 5.39 (d, J=3.3 Hz, 1H, H-4), 5.29 (dd, J=3.3, 11.1 Hz, 1H, H-3), 4.89 (d, J=10.5 Hz, 1H, H-1), 4.22-4.09 (m, 3H, H-2, H-6), 3.94 (dd, J=6.6, 6.6 Hz, 1H, H-5), 2.34 (s, 3H, SPhCH$_3$), 2.13 (s, 3H, OC(O)CH$_3$), 2.04 (s, 3H, OC(O)CH$_3$), 1.97 (s, 3H, OC(O)CH$_3$); $^{13}$C NMR (75 MHz, CDCl$_3$): δ=170.6, 170.5, 170.2, 161.9, 138.8, 133.5, 129.9, 128.5, 92.5, 87.2, 74.9, 70.9, 67.1, 62.0, 51.7, 21.6, 21.1, 21.0, 20.9; FAB MS: m/z: calcd for $C_{21}H_{25}C_{13}NO_8S$: 556.0367. found: 556.0369 [M+H]$^+$.

B3)$_p$-Methylphenyl 2-deoxy-2-trichloroacetamido-3-O-triisopropylsilyl-4,6-O-p-methoxybenzylidene-1-thio-β-D-galactopyranoside (11'). A solution of 10' (17.9 g, 0.0320 mol) in dry $CH_2Cl_2$ (85 mL) and MeOH (435 mL) was stirred at rt for 30 min and NaOMe (25 wt % solution in MeOH, 0.517 g, 9.58 mmol, 2.07 mL) was then added. The mixture was stirred for 2 h and DOWEX 50×8-200 added and stirring continued for a further 30 min. The DOWEX was removed by filtration and the solvent removed in vacuo to afford 11' (13.5 g, 98%) as a yellow solid. This compound was suitable for the next step without purification.

B4) p-Methylphenyl 2-deoxy-2-trichloroacetamido-4,6-O-p-methoxybenzylidene-1-thio-β-D-galactopyranoside (12'). To a solution of 11' (13.5 g, 0.0310 mol) in acetonitrile (800 mL, minimum amount) was added p-anisaldehyde dimethyl acetal (11 g, 0.063 mol, 12 mL) and DL-10-camphorsulfonic acid (10 mol %) and the mixture stirred at rt for 12 h. The reaction mixture was quenched with TEA and the solvent concentrated to afford a yellow solid. Purification of this solid by flash chromatography (40%→80% EtOAc:hexanes) afforded 12' (13 g, 76%) as a white solid. $R_f$ 0.25 (50% EtOAc:hexanes). $[\alpha]_D^{24}=-14.6$ (c=0.5, $CH_2Cl_2$); IR (thin film on NaCl): ν=3333, 1687, 1615, 1519, 1492, 1403, 1364, 1301, 1248, 1167, 1095, 1055 cm$^{-1}$; $^1$H NMR (300 MHz, CDCl$_3$): δ=7.55 (d, J=8.4 Hz, 2H, SC$_6$H$_4$Me), 7.34 (d, J=8.7 Hz, 2H, C$_6$H$_4$OMe), 7.12 (d, J=8.4 Hz, 2H, SC$_6$H$_4$Me), 6.88 (d, J=8.7 Hz, 2H, C$_6$H$_4$OMe), 6.81 (d, J=7.5 Hz, 1H, NH), 5.48 (s, 1H, MeOPhCH), 5.03 (d, J=9.9 Hz, 1H, H-1), 4.37 (dd, J=1.5, 12.6 Hz, 1H, H-6), 4.20-4.10 (m, 2H, H-3, H-4), 4.01 (dd, J=1.5, 12.6 Hz, 1H, H-6), 3.83 (s, 3H, PhOCH$_3$), 3.69 (m, 1H, H-2), 3.57 (s, 1H, H-5), 2.58 (d, J=10.5 Hz, 1H, OH), 2.37 (s, 31-1, SPhCH$_3$); $^{13}$C NMR, (75 MHz, CDCl$_3$): δ=162.1, 160.5, 139.0, 134.7, 130.2, 130.0, 128.1, 126.9, 113.8, 101.4, 84.0, 75.2, 70.7, 70.3, 69.5, 55.7, 54.4, 21.7; FAB MS: m/z: calcd for $C_{23}H_{25}Cl_3NO_6S$: 548.0469. found: 548.0448 [M+H]$^+$.

B5) p-Methylphenyl 2-deoxy-2-trichloroacetamido-3-O-triisopropylsilyl-4,6-O-p-methoxybenzylidene-β-D-galactopyranoside (13'). To a solution of 12' (5.6 g, 0.010 mol) in dry DMF (50 mL) at rt was added triisopropylsilyl chloride (6.3 g, 0.033 mol, 7.0 mL), imidazole (2.7 g, 0.040 mol) and DMAP (0.49 g, 40 mol %). The reaction mixture was stirred for 4 h whereupon further addition of triisopropylsilyl chloride (3.2 g, 0.016 mol, 3.5 mL), imidazole (1.4 g, 0.020 mol) and DMAP (0.25 g, 20 mol %) were added. The reaction mixture was stirred for 12 h and quenched with saturated aqueous $NaHCO_3$. The aqueous layer was extracted with EtOAc (3×) and the combined organics washed with brine and dried over $MgSO_4$ to afford a pale yellow oil. Purification of this oil by flash chromatography (10%→15% EtOAc:hexanes) afforded 13' (5.3 g, 75%) as a white solid. $R_f$ 0.57 (30% EtOAc:hexanes). $[\alpha]_D^{23}=+5.9$ (c=0.5, $CH_2Cl_2$); ER (thin film on NaCl): ν=2943, 2866, 1705, 1616, 1519, 1493, 1464, 1365, 1249, 1170, 1139, 1083, 1051 cm$^{-1}$; $^1$H NMR (300 MHz, CDCl$_3$): δ=7.57 (d, J=8.1 Hz, 2H, SC$_6$H$_4$Me), 7.38 (d, J=8.7 Hz, 2H, C$_6$H$_4$OMe), 7.07 (d, J=8.1 Hz, 2H, SC$_6$H$_4$Me), 6.87 (d, J=8.7 Hz, 2H, C$_6$H$_4$OMe), 6.85 (m, 1H, NH), 5.45 (s, 1H, MeOPhCH), 5.39 (d, J=9.9 Hz, 1H, H-1), 4.62 (dd, J=3.2, 10.2 Hz, 1H, H-3), 4.37 (dd, J=1.7, 12.5 Hz, 1H, H-6), 4.13 (d, J=3.2 Hz, 1H, H-4), 4.01 (dd, J=1.7, 12.5 Hz, 1H, H-1-6), 3.83 (s, 3H, PhOCH$_3$), 3.71 (m, 1H, H-2), 3.55 (s, 1H, H-5), 2.34 (s, 3H, SPhCH$_3$), 1.01 (s, 21H, [(CH$_3$)$_2$CH]$_3$), $^{13}$C NMR (75 MHz, CDCl$_3$): δ=161.3, 160.1, 138.5, 134.1, 130.7, 130.0, 128.0, 127.9, 113.5, 101.1, 83.4, 76.7, 71.0, 70.3, 69.7, 55.6, 54.8, 21.7, 18.5, 18.4, 13.1; FAB MS: m/z: calcd for $C_{32}H_{45}Cl_3NO_6SSi$: 704.1621. found: 704.1623 [M+H]$^+$.

B6) Allyl 2-deoxy-2-trichloroacetamido-3-O-triisopropylsilyl-4,6-O-p-methoxybenzylidene-β-D-galactopyranoside (14'). To a solution of 13' (11 g, 0.016 mol) in dry $CH_2Cl_2$ (675 mL) was added 4 Å powdered molecular sieves and the mixture stirred for 1 h. Allyl alcohol (9.3 g, 0.16 mol, 11 mL) and N-iodosuccinimide (5.3 g, 0.023 mol) was added and the mixture cooled to 0° C. Triflic acid (0.5 N solution in $CH_2Cl_2$, 1.44 g, 9.60 mmol, 19.2 mL) was added and the reaction stirred at 0° C. for 10 min. The mixture was quenched with TEA, washed with brine and dried over $MgSO_4$. The solvent was removed in vacuo to afford a yellow oil. Purification of this oil by flash chromatography (5%→15% EtOAc:hexanes) afforded 14' (8.1 g, 79%) as a white solid. $R_f$ 0.41 (30% EtOAc:hexanes). $[\alpha]_D^{24}=+38.1$ (c=0.5, $CH_2Cl_2$); IR (thin film on NaCl): ν=3445, 1644, 1520, 1463, 1368, 1249, 1171, 1123, 1060 cm$^{-1}$; $^1$H NMR (300 MHz, CDCl$_3$): δ=7.45 (d, J=8.9 Hz, 2H, C$_6$H$_4$OMe), 6.97 (d, J=7.2 Hz, 1H, NH), 6.87 (d, J=8.9 Hz, 2H, C$_6$H$_4$OMe), 5.96-5.83 (m, 1H, OCH$_2$CH=CH$_2$), 5.49 (s, 1H, MeOPhCH), 5.26 (dd, J=1.4, 17.3 Hz, 1H, OCH$_2$CH=CH$_2$), 5.17 (dd, J=1.4, 10.5 Hz, 1H, OCH$_2$CH=CH$_2$), 5.16 (d, J=8.1 Hz, 1H, H-1), 4.65 (dd, J=3.3, 10.5 Hz, 1H, H-3), 4.37 (m, 2H, OCH$_2$CH=CH$_2$, H-6), 4.13-4.05 (3H, m, OCH$_2$CH=CH$_2$, H-4, H-6), 3.81 (s, 311, PhOCH$_3$), 3.75 (m, 1H, H-2), 3.48 (s, 1H, H-5), 1.05 (s, 21H, [(CH$_3$)$_2$CH]$_3$); $^{13}$C NMR (75 MHz, CDCl$_3$): δ=161.7, 160.1, 134.0, 130.5, 127.8, 118.2, 113.6, 101.2, 97.8, 76.6, 70.6, 69.9, 69.5, 66.7, 64.2, 57.6, 55.6, 18.5, 18.4, 13.1; FAB MS: m/z: calcd for $C_{25}H_{37}Cl_3NO_6Si$: 580.1456. found: 580.1474 [M$^+$-OAll].

B7) Allyl 2-deoxy-2-trichloroacetamido-4,649-p-methoxybenzylidene-β-D-galactopyranoside (6). To a solution of 14' (8.00 g, 12.5 mmol) in THF (290 mL) was added tetrabutylammonium fluoride (1 N solution in THF, 4.91 g, 18.8 mmol, 18.8 mL) and the mixture stirred at rt for 8 h. At this time a second addition of tetrabutylammonium fluoride (2.5 g, 9.4 mmol, 9.4 mL) was made and the reaction stirred for a further 12 h. The solvent was removed in vacuo to afford a yellow oil. Purification of this oil by flash chromatography (40%→80% EtOAc:hexanes) afforded 6 (5.14 g, 85%) as a white solid. $R_f$ 0.17 (50% EtOAc:hexanes). $[\alpha]_D^{24}=+0.62$ (c=0.5, $CH_2Cl_2$); IR (thin film on NaCl): ν=3423, 1686, 1616, 1531, 1402, 1366, 1303, 1249, 1170, 1097, 1060 cm$^{-1}$; $^1$H NMR (300 MHz, CDCl$_3$): δ=7.43 (d, J=8.7 Hz, 2H, C$_6$H$_4$OMe), 6.89 (d, J=8.7 Hz, 2H, C$_6$H$_4$OMe), 6.87 (m, 1H, NH), 5.95-5.82 (m, 1H, OCH$_2$CH=CH$_2$), 5.54 (s, 1H, MeOPhCH), 5.29 (dd, J=1.4, 17.7 Hz, 1H, OCH$_2$CH=CH$_2$), 5.19 (dd, J=1.4, 10.5 Hz, 1H, OCH$_2$CH=CH$_2$), 4.84 (d, J=8.4 Hz, 1H, H-1), 4.44±4.32 (m, 2H, H-3, H-6), 4.26-4.07 (m, 4H, OCH$_2$CH=CH$_2$, H-4, H-6), 3.81 (m, 1H, H-2), 3.81 (s, 3H, PhOCH$_3$), 3.53 (s, 1H, H-5), 2.71 (d, J=9.9 Hz, 1H, OH); $^{13}$C NMR (75 MHz, CDCl$_3$): δ=162.5, 160.4, 153.6, 133.7, 130.0, 127.9, 118.3, 113.8, 101.6, 98.7, 75.2, 70.4, 69.4, 69.3, 67.0, 57.2, 55.7; FAB MS: m/z: calcd for C$_{19}$H$_{23}$Cl$_3$NO$_7$: 482.0540. found: 482.0531 [M+H]$^+$.

C. Reaction of Glucuronic Acid Monomer 5 and Galactosamine Monomer 6

C1. Allyl (methyl 2,3-di-O-benzoyl-4-O-tert-butyldimethylsilyl-β-D-glucopyranosyluronate)-(1→3)-4,6-O-p-methoxybenzylidene-2-deoxy-2-trichloroacetamido-β-D-galactopyranoside (4).

A mixture of donor 5 (0.50 g, 0.74 mmol) and acceptor 6 (0.30 g, 0.62 mmol) was coevaporated with toluene (3×3 mL) and dried under vacuum overnight. The mixture was dissolved in CH$_2$Cl$_2$ (16 mL), and activated 4 Å powdered molecular sieves were added. The reaction was stirred at rt for 1.5 h. The reaction was then cooled to −40° C. and stirred for an additional 30 min. Trimethylsilyl trifluoromethanesulfonate (1 M in CH$_2$Cl$_2$, 125 μL, 0.123 mmol) at −40° C. was added to the reaction dropwise. The reaction was allowed to stir an additional 30 min. It was then warmed to −10° C. over a period of 30 min (a carefully controlled temperature gradient was essential to avoid formation of the inseparable ortho ester) quenched with TEA, and allowed to warm to rt. The reaction was filtered and concentrated to afford a yellow syrup. The product was purified by flash chromatography (30% EtOAc:hexanes) to afford 4 (0.46 g, 74%) as a white solid. R$_f$ 0.12 (30% EtOAc:hexanes). NMR (300 MHz, CDCl$_3$): δ=7.87-7.82 (m, 4H, ArH), 7.48-7.39 (m, 4H, ArH), 7.35-7.26 (m, 4H, Ph ArH), 6.86 (d, J=8.7 Hz, 2H, C$_6$H$_4$OMe), 6.82 (d, J=7.2 Hz, 1H, NH), 5.89-5.76 (m, 1H, OCH$_2$CH=CH$_2$), 5.45 (s, 1H, MeOPhCH), 5.52-5.39 (m, 2H, H-2', H-3'), 5.22 (dd, J=1.6, 17.6 Hz, 1H, OCH$_2$CH=CH$_2$), 5.13 (dd, J=1.0, 10.4 Hz, 1H, OCH$_2$CH=CH$_2$), 5.08 (d, J=7.5 Hz, 1H, H-1'), 5.05 (d, J=8.1 Hz, 1H, H-1), 4.67 (dd, J=3.3, 10.8 Hz, 1H, H-3), 4.36-4.27 (m, 4H, OCH$_2$CH=CH$_2$, H-4, H-4' H-6), 4.10 (d, J=9.3 Hz, 1H, H-5'), 4.07-4.01 (m, 2H, OCH$_2$CH=CH$_2$, H-6), 3.79 (s, 6H, CO$_2$CH$_3$, PhOCH$_3$), 3.77-3.68 (m, 1H, H-2), 3.48 (s, 1H, H-5), 0.72 (s, 9H, (CH$_3$)$_3$CSi), −0.08 (s, 3H, CH$_3$Si), −0.23 (s, 3H, CH$_3$Si); $^{13}$C NMR (75 MHz, CDCl$_3$): δ=168.7, 165.7, 165.2, 162.3, 160.0, 133.8, 133.4, 133.4, 130.5, 130.0, 129.9, 129.5, 129.2, 128.5, 127.7, 118.2, 113.6, 100.7, 100.6, 97.8, 92.3, 76.4, 75.8, 75.6, 73.6, 72.0, 70.9, 70.6, 69.2, 66.8, 55.6, 55.4, 52.9, 25.7, 18.1, −4.0, −4.7; FAB MS: to/z: calcd for C$_{46}$H$_{53}$Cl$_3$NO$_{15}$Si: 992.2250. found: 992.2255 [M]$^+$.

C2. Methyl (2,3-di-O-benzoyl-4-O-tert-butyldimethylsilyl-β-D-glucopyranosyluronate)-(1→3)-4,6-O-p-methoxybenzylidene-2-deoxy-2-trichloroacetamido-α-D-galactopyranoside trichloroacetimidate (7).

To a solution of 4 (2.5 g, 2.5 mmol) in dry CH$_2$Cl$_2$ (40 mL) was added Grubbs' second generation catalyst (Scholl, M. et al. Org. Lett. 1999, 1, 953-956) (0.43 g, 20 mol %) and the mixture stirred at rt for 2 h. The solvent was removed in vacuo to afford a brown oil. Purification of this oil by flash chromatography (15%→20% EtOAc:hexanes) afforded E/Z-prop-2-enyl(methyl 2,3-di-O-benzoyl-4-O-tert-butyldimethylsily-β-D-glucopyranosyluronate)-(1→3)-4,6-O-p-methoxybenzylidene-2-deoxy-2-trichloroacetamido-β-D-galactopyranoside (1.92 g, 77%) as a white solid. R$_f$(E and Z) 0.68 (60% EtOAc:hexanes). [α]$_D^{25}$=+29.1 (c=1.0, CH$_2$Cl$_2$); IR (thin film on NaCl): ν=3308, 2954, 2858, 1755, 1734, 1717, 1694, 1617, 1602, 1540, 1520, 1452, 1371, 1268, 1221, 1176, 1147, 1089, 1069, 1040, 1026, 1001 cm$^{-1}$; $^1$H NMR (300 MHz, CDCl$_3$): δ=7.85 (m, 3H, ArH), 7.48±7.28 (m, 10H, ArH, OCH=CHCH$_3$), 6.87 (d, J=8.7 Hz, 2H, C$_6$H$_4$OMe), 6.82 (d, J=6.6 Hz, 1H, NH), 6.17 (m, 1H, CH=CHCH$_3$), 5.52-5.40 (m, 3H, MeOPhCH, H-2', H-3'), 5.19 (d, J=8.1 Hz, 1H, H-1), 5.08 (d, J=7.2 Hz, 1H, H-1'), 4.68 (dd, J=3.8, 11.0 Hz, 1H, H-3), 4.39-4.28 (m, 3H, H-4, H-4', H-6), 4.16-4.02 (m, 2H, H-5', H-6), 3.87 (m, 1H, H-2), 3.81 (s, 3H, PhOCH$_3$), 3.80 (s, 3H, CO$_2$CH$_3$), 3.45 (s, 1H, H-5), 1.51 (m, 3H, OCH=CHCH$_3$), 0.72 (s, 9H, (CH$_3$)$_3$CSi), −0.07 (s, 3H, CH$_3$Si), −0.22 (s, 3H, CH$_3$Si); $^{13}$C NMR (75 MHz, CDCl$_3$): δ=168.7, 165.7, 165.3, 162.4, 162.3, 160.0, 143.5, 142.1, 133.5, 133.4, 130.4, 130.1, 129.9, 129.5, 129.1, 128.5, 127.7, 113.6, 105.7, 104.8, 100.8, 100.6, 100.5, 98.4, 98.0, 76.5, 75.6, 75.5, 73.5, 73.4, 72.0, 70.9, 69.0, 67.2, 67.1, 55.6, 55.1, 55.0, 52.9, 25.7, 18.1, 12.6, 9.7, −4.0, −4.7.

To a solution of E/Z-prop-2-enyl(methyl 2,3-di-O-benzoyl-4-O-tert-butyldimethylsilyl-β-D-glucopyranosyluronate)-(1→3)-4,6-O-p-methoxybenzylidene-2-deoxy-2-trichloroacetamido-β-D-galactopyranoside (6.2 g, 6.3 mmol) in dry THF (118 mL), water (24 mL) and pyridine (1.9 mL) was added iodine (3.1 g) and the mixture stirred at ambient temperature for 30 min. The solvent was removed in vacuo to afford a yellow oil. The oil was taken up in EtOAc and washed with 5% aqueous Na$_2$SO$_3$, saturated aqueous NaHCO$_3$, brine and dried over MgSO$_4$. The solvent was removed in vacuo to afford a pale yellow oil. Purification of this oil by flash chromatography (40%→60% EtOAc:hexanes) afforded an anomeric mixture of methyl (2,3-di-O-benzoyl-4-O-tert-butyldimethylsilyl-β-D-glucopyranosyluronate)-(1→3)-4,6-O-p-methoxybenzylidene-2-deoxy-2-trichloro-acetamido-α/β-D-galactopyranoside (4.8 g, 81%) as a pale yellow solid. R$_f$ 0.28 and 0.18 (50% EtOAc:hexanes). [α]$_D^{25}$=+79.0 (c=1.0, CH$_2$Cl$_2$); IR (thin film on NaCl): ν=3521, 2930, 1738, 1682, 1615, 1519, 1452, 1394, 1251, 1172, 1093, 1069, 1031 cm$^{-1}$; $^1$H NMR (300 MHz, CDCl$_3$): δ=7.92-7.85 (m, 3H, ArH), 7.54-7.45 (m, 3H, ArH), 7.40-7.27 (m, 4H, ArH), 7.12 (d, J=9.0 Hz, 2H, C$_6$H$_4$OMe), 6.96 (d, J=6.3 Hz, 1H, NH), 6.72 (d, J=9.0 Hz, 2H, C$_6$H$_4$OMe), 5.60 (m, 1H, H-1), 5.50 (dd, J=8.2, 8.2 Hz, 1H, H-3'), 5.42 (dd, J=8.2, 8.2 Hz, 1H, H-2'), 5.24 (s, 1H, MeOPhCH), 5.21 (d, J=7.5 Hz, 1H, H-1'), 4.39-4.35 (m, 4H, H-3, H-4, H-4'), 4.23-4.02 (m, 3H, H-2, H-5', H-6), 3.96 (s, 1H, H-5), 3.79 (s, 3H, PhOCH$_3$), 3.75 (s, 3H, CO$_2$CH$_3$), 3.03 (d, J=3.3 Hz, 1H, OH), 0.73 (s, 9H, (CH$_3$)$_3$CSi), −0.08 (s, 3H, CH$_3$Si), −0.22 (s; 3H, CH$_3$Si); ESI MS: m/z: calcd for C$_{43}$H$_{50}$Cl$_3$NO$_{15}$Si: 954.2914. found: 954 [M−H]$^-$.

To a solution of methyl (2,3-di-O-benzoyl-4-O-tert-butyldimethylsilyl-fi-D-glucopyranosyluronate)-(1→3)-4,6-O-p-methoxybenzylidene-2-deoxy-2-trichloroacetamido-α/β-D-galactopyranoside (4.6 g, 4.8 mmol) in dry CH$_2$Cl$_2$ (190 mL) cooled to 0° C. was added 1,8-diazabicyclo[5.4.0]undec-7-ene (0.29 g, 1.9 mmol, 0.29 μL) and trichloroacetonitrile (10 g, 71 mmol, 7.2 mL) and the mixture stirred for 15 min. The mixture was quenched with TEA and concentrated in vacuo to afford a yellow oil. Purification of this oil by flash chromatography (35% EtOAc:hexanes, +2% TEA) afforded 7 (4.7 g, 90%) as a pale yellow foam. R$_f$ 0.74, (50% EtOAc:hexanes). [α]$_D^{24}$=+12.0 (c=0.5, CH$_2$Cl$_2$); IR (thin film on NaCl): ν=3422, 2956, 2991, 2361, 1731, 1676, 1616, 1519, 1452, 1373, 1271, 1177, 1147, 1094, 1070, 1028 cm$^{-1}$; $^1$H NMR (300 MHz, CDCl$_3$): δ=8.69 (s, 1H, C=NH), 7.90 (m, 4H, ArH), 7.51 (m, 2H, ArH), 7.42-7.26 (m, 4H, ArH), 7.00 (d, J=8.9 Hz, 211, C$_6$H$_4$OMe), 6.93 (d, J=5.4 Hz, 1H, NHTCA), 6.77 (d, J=2.1 Hz, 1H, H-1), 6.68 (d, J=8.9 Hz, 2H, C$_6$H$_4$OMe), 5.52 (dd, J=8.7, 8.7 Hz, 1H, H-3'), 5.45 (dd, J=8.7, 8.7 Hz, 1H, H-2'), 5.27 (d, J=7.8 Hz, 1H, H-1'), 5.17 (s, 1H, MeOPhCH), 4.62 (m, 2H, H-4, H-4'), 4.49 (m, 1H, H-3), 4.31 (m, 2H, H-2, H-6), 4.18 (d, J=9.0 Hz, 1H, H-5'), 4.00 (d, J=12.6 Hz, 1H, H-6), 3.94 (s, 1H, H-5), 3.75 (s, 3H, PhOCH$_3$), 3.74 (s, 3H, CO$_2$CH$_3$), 0.73 (s, 9H, (CH$_3$)$_3$CSi), −0.06 (s, 3H, CH$_3$Si), −0.19 (s, 3H, CH$_3$Si); $^{13}$C NMR (75 MHz, CDCl$_3$): δ=168.1, 165.9, 165.6, 162.0, 160.4, 133.9, 133.6, 130.1, 129.9, 129.4, 128.7, 128.6, 127.6, 113.6, 101.1, 98.4, 95.3, 77.2, 75.5, 74.4, 71.2, 70.9, 69.2, 69.0, 65.5, 55.6, 53.0, 50.5, 46.5, 25.7, −4.0, −4.8.

C3. Allyl (methyl 2,3-di-O-benzoyl-β-D-glucopyranosyluronate)-(1→3)-4,6-O-p-methoxybenzylidene-2-deoxy-2-trichloroacetamido-β-D-galactopyranoside (8). To a solution of 4 (2.5 g, 2.5 mmol) in dry THF (40 mL) and pyridine (40 mL) cooled to 0° C. was added HF.pyridine (13 mL). The reaction mixture was warmed to rt and stirred for 18 h. The mixture was then diluted with EtOAc and washed with 10% aqueous $CuSO_4$. The aqueous phase was extracted with EtOAc (3×) and the combined organics washed with saturated aqueous $NaHCO_3$ and dried over $MgSO_4$. The solvent was removed in vacuo to afford a yellow oil. Purification of this oil by flash chromatography (30→60% EtOAc:hexanes) afforded 8 (1.9 g, 85%) as a white solid. $R_f$ 0.35 (60% EtOAc:hexanes). $[α]_D^{25}$=+32.8 (c=1.0, $CH_2Cl_2$); IR (thin film on NaCl): ν=3422, 1731, 1616, 1519, 1452, 1369, 1251, 1173, 1093, 1069 $cm^{-1}$; $^1H$ NMR (300 MHz, $CDCl_3$): ν=7.93-7.87 (m, 4H, ArH), 7.50-7.42 (m, 4H, ArH, $C_6H_4OMe$), 7.36-7.26 (m, 4H, ArH), 7.01 (d, J=6.6 Hz, 1H, NH), 6.89 (d, J=8.7 Hz, 2H, $C_6H_4OMe$), 5.89-5.77 (m, 1H, $OCH_2CH=CH_2$), 5.47 (m, 3H, MeOPhCH, H-2', H-3'), 5.26-5.12 (m, 4H, $OCH_2CH=CH_2$, H-1, H-1'), 4.73 (dd, J=3.6, 11.4 Hz, 1H, H-3), 4.41-4.28 (m, 3H, $OCH_2CH=CH_2$, H-4, H-6), 4.19 (m, 1H, H-4'), 4.12-4.02 (m, 3H, $OCH_2CHCH_2$, H-5', H-6), 3.83 (s, 3H, $PhOCH_3$), 3.81 (s, 3H, $CO_2CH_3$), 3.72 (m, 1H, H-2), 3.48 (s, 1H, H-5), 3.45 (d, J=3.3 Hz, 1H, OH); $^{13}C$ NMR (75 MHz, $CDCl_3$): δ=169.3, 166.6, 165.2, 162.3, 160.1, 133.8, 133.6, 133.5, 130.4, 130.1, 130.0, 129.2, 129.1, 128.7, 128.6, 127.5, 118.2, 113.7, 100.8, 100.7, 97.7, 76.1, 75.4, 74.3, 74.1, 71.4, 70.7, 69.3, 66.8, 55.7, 53.4; ESI MS: Fez: calcd for $C_{40}H_{39}Cl_3NO_{15}$; 880.1. found: 880.2 [M−H]⁻

C4. Allyl (methyl 2,3-di-O-benzoyl-4-O-tert-butyldimethylsilyl-β-D-glucopyranosyluronate)-(1→3)-2-deoxy-2-acetamido-β-D-galactopyranoside (10). 10 was prepared using a procedure modified from Bélot et. al. (Bélot, F.; Jacquinet, J.-C. Carbohydr. Res. 2000, 326, 88-97) 4 (250 mg, 0.251 mmol) was dissolved in benzene (7.80 mL). Tributylstannane (305 μL, 1.51 mmol) and 2,2'-azobisisobutyronitrile (80.0 mg) were added. The reaction was stirred at rt for 45 min. It was then heated to 80° C. and stirred an additional 1.5 h. The reaction was cooled to rt and concentrated to afford a white solid. The product was purified by flash chromatography (50% EtOAc:hexanes) to afford allyl(methyl 2,3-di-O-benzoyl-4-O-tert-butyldimethylsilyl-β-D-glucopyranosyluronate)-(1→3)-4,6-O-p-methoxybenzylidene-2-deoxy-2-acetamido-β-D-galactopyranoside (190 mg, 85%) as a white solid. $R_f$ 0.19 (50% EtOAc:hexanes). $^1H$ NMR (300 MHz, $CDCl_3$): δ=7.89-7.86 (m, 4H, ArH), 7.51-7.42 (m, 4H, ArH), 7.37-7.31 (m, 4H, ArH), 6.88 (d, J=8.7 Hz, 21-1, $C_6H_4OMe$), 5.91-5.75 (m, 1H, $OCH_2CH=CH_2$), 5.55 (dd, J=8.9, 8.9 Hz, 1H, H-3'), 5.46 (s, 1H, MeOPhCH), 5.40-5.35 (m, 2H, NH, H-2'), 5.20 (dd, J=1.4, 17.3 Hz, 1H, $OCH_2CH=CH_2$), 5.14-5.11 (m, 2H, $OCH_2CH=CH_2$, H-1), 4.97 (d, J=7.5 Hz, 1H, H-1'), 4.77 (dd, J=3.9, 11.1 Hz, 1H, H-3), 4.37-4.25 (m, 4H, $OCH_2CH=CH_2$, H-4, H-4', H-6), 4.10 (d, J=9.6 Hz, 1H, H-5'), 4.10-3.98 (m, 2H, $OCH_2CH=CH_2$, H-6), 3.81 (s, 3H, $CO_2CH_3$), 3.78 (s, 3H, $PhOCH_3$), 3.47 (s, 1H, H-5), 3.34-3.26 (m, 1H, H-2), 1.53 (s, 3H, $HNC(O)CH_3$), 0.72 (s, 9H, $(CH_3)_3CSi$), −0.07 (s, 3H, $CH_3Si$), −0.23 (s, 3H, $CH_3Si$); $^{13}C$ NMR (75 MHz, $CDCl_3$): δ=171.4, 168.7, 165.8, 165.0, 160.0, 134.1, 133.5, 133.4, 130.7, 129.9, 129.8, 129.6, 129.5, 128.6, 128.5, 127.8, 118.0, 113.6, 101.6, 100.8, 98.0, 76.3, 76.1, 75.6, 72.4, 70.9, 70.4, 69.4, 66.7, 55.6, 55.1, 52.9, 25.8, 23.6, 18.1, −4.0, −4.7; ESI MS: [M+Na]⁺ calcd for $C_{46}H_{57}NNaO_{15}Si$: 914.3. found 914.4.

Allyl (methyl 2,3-di-O-benzoyl-4-O-tert-butyldimethylsilyl-β-D-glucopyranosyluronate)-(1→3)-4,6-O-p-methoxybenzylidene-2-deoxy-2-acetamido-β-D-galactopyranoside (190 mg, 0.213 mmol) was dissolved in $CH_2Cl_2$ (2.40 mL) and $H_2O$ (0.560 mL). 2,3-Dichloro-5,6-dicyano-1,4-benzoquinone (73.0 mg, 0.320 mmol) was added. The reaction was stirred at rt for 3 h, quenched with MeOH, and concentrated to yield a red solid. The product was purified on Sephadex LH-20 (50% $CH_2Cl_2$:MeOH), followed by silica gel chromatography (100% EtOAc), to afford an orange solid containing the desired diol 10 (102 mg, 62%). $R_f$ 0.23 (100% EtOAc). $^1H$ NMR (300 MHz, $CD_3OD$): δ=7.90-7.86 (m, 4H, ArH), 7.49-7.44 (m, 2H, ArH), 7.37-7.29 (m, 4H, ArH), 5.83-5.74 (m, 1H, $OCH_2CH=CH_2$), 5.61 (dd, J=9.0, 8.7 Hz, 1H, H-3'), 5.35 (dd, J=8.1, 9.0 Hz, 1H, H-2'), 5.18 (dd, J=1.7, 17.6 Hz, 1H, $OCH_2CH=CH_2$), 5.10 (d, J=9.9 Hz, 1H, $OCH_2CH=CH_2$), 4.97 (d, J=7.5 Hz, 1H, H-1'), 4.90 (d, J=7.5 Hz, 1H, H-1), 4.552 (m, 1H, NH), 4.29-4.17 (m, 3H, H-1, H-4, H-6), 4.03-3.93 (m, 4H, $OCH_2CH=CH_2$, H-3, H-4', H-6), 3.89-3.86 (m, 2H, $OCH_2CH=CH_2$, H-5, H-5'), 3.65 (m, 1H, H-2), 3.78 (s, 3H, $CO_2CH_3$), 1.26 (s, 3H, $HNC(O)CH_3$), 0.73 (s, 9H, $(CH_3)_3CSi$), −0.07 (s, 3H, $CH_3Si$), −0.20 (s, 3H, $CH_3Si$); ESI MS: m/z: calcd for $C_{39}H_{52}NO_{14}Si$ 774.9. found 774.2 [M+H]⁺.

C5. Allyl (sodium β-D-glucopyranosyluronate)-(1→3)-4,6-di-O-sodium sulfonato-2-deoxy-2-acetamido-β-D-galactopyranoside (1). The crude diol 10 (102 mg, 0.132 mmol) was dissolved in DMF (5 mL). $SO_3$.TMA (0.550 g, 3.96 mmol) was added. The reaction was stirred at 50° C. overnight. It was cooled to rt, quenched with MeOH, and concentrated to afford a yellow solid. The product was purified on Sephadex LH-20 (50% $CH_2Cl_2$:MeOH), followed by silica gel chromatography (10%→20% MeOH:$CH_2Cl_2$), to afford allyl (methyl 2,3-di-O-benzoyl-4-O-tert-butyldimethylsilyl-β-D-glucopyranosyluronate)-(1→3)-4,6-di-O-sodium sulfonato-2-deoxy-2-acetamido-β-D-galactopyranoside (115 mg, 93%) as a white solid. $R_f$ 0.125 (15% MeOH:$CH_2Cl_2$). $^1H$ NMR (300 MHz, $CD_3OD$): 7.88-7.85 (m, 4H, ArH), 7.54-7.47 (m, 2H, ArH), 7.38-7.32 (m, 4l1, ArH), 5.86-5.73 (m, 1H, $OCH_2CH=CH_2$), 5.67 (dd, J=9.3, 9.3 Hz, 1H, H-3'), 5.48 (dd, J=8.1, 9.2 Hz, 1H, H-2'), 5.18 (dd, J=1.7, 17.6 Hz, 1H, $OCH_2CH=CH_2$), 5.11 (d, J=7.5 Hz, 1H, H-1'), 5.05 (dd, J=1.8, 10.5 Hz, 1H, $OCH_2CH=CH_2$), 4.44-4.35 (m, 3H, H-1, H-4, H-6), 4.30-4.22 (m, 4H, $OCH_2CH=CH_2$, H-3, H-4', H-6), 4.09-3.98 (m, 2H, $OCH_2CH=CH_2$, H-5), 3.95-3.91 (m, 2H, H-2, H-5'), 3.86 (s, 3H, $CO_2CH_3$), 1.30 (s, 3H, $HNC(O)CH_3$), 0.74 (s, 9H, $(CH_3)_3CSi$), −0.02 (s, 3H, $CH_3Si$), −0.18 (s, 3H, $CH_3Si$); $^{13}C$ NMR (75 MHz, $CD_3OD$): δ=172.3, 170.0, 166.2, 165.8, 134.1, 133.5, 133.4, 130.0, 129.5, 129.4, 129.0, 128.3, 128.2, 115.9, 102.5, 100.8, 79.2, 76.3, 75.9, 75.4, 72.8, 72.6, 70.9, 69.7, 67.6, 54.2, 52.6, 25.0, 21.4, 17.6, −4.9, −5.6; FAB MS: In/z: calcd for $C_{38}H_{49}NNa_3O_{20}S_2Si$: 1000.175. found: 1000.175 [M+Na]⁺.

Allyl (methyl 2,3-di-O-benzoyl-4-O-tert-butyldimethylsilyl-β-D-glucopyranosyluronate)-(1→3)-4,6-di-O-sodium sulfonato-2-deoxy-2-acetamido-β-D-galactopyranoside (115 mg, 0.123 mmol) was dissolved in pyridine (1.7 mL) and THF (1.7 mL). The reaction was cooled to 0° C., HF.pyridine (0.60 mL) was added, and it slowly warmed to rt overnight. After 12 h, the mixture was flowed through a Sephadex LH-20 column (50% $CH_2Cl_2$:MeOH) and the concentrated residue was purified by silica gel chromatography (10%→20% MeOH:$CH_2Cl_2$) to afford a white solid (90.0 mg). $R_f$ 0.50 (EtOAc:pyr:$H_2O$:AcOH, 8:5:3:1).

The crude alcohol (90 mg, 0.11 mmol) was dissolved in THF (1.8 mL) and $H_2O$ (1.8 mL) and to this was added 2 M NaOH (0.72 mL). After 12 h at rt, the reaction was neutralized with Amberlyst IR-120 resin, filtered, and lyophilized to afford an orange solid. The product was purified on Sephadex G-10 (100% $H_2O$) and Sephadex SP C25 (100% $H_2O$) and lyophilized to afford 1 (45 mg, 55%, 2 steps) as a white solid. $R_f$ 0.12 (EtOAc:pyr:$H_2O$:AcOH, 8:5:3:1). $^1H$ NMR (300 MHz, $D_2O$): δ=5.79-5.66 (m, 1H, $OCH_2CH=CH_2$), 5.17-5.07 (m, 2H, $OCH_2CH=CH_2$), 4.42-4.39 (m, 1H), 4.31 (d, J=7.8 Hz, 1H, H-1'), 4.16-4.10 (m, 2H), 4.05-3.98 (m, 3H), 3.90-3.87 (m, 3H), 3.53 (dd, J=9.0, 9.0 Hz, 1H), 3.36-3.29 (m, 2H), 3.21-3.16 (m, 1H), 1.84 (s, 3H, $HNC(O)CH_3$); $^{13}C$ NMR (75 MHz, $D_2O$): δ=118.7, 103.4, 100.0, 175.6, 174.8, 133.2, 76.4, 75.2, 75.1, 72.6, 72.4, 71.9, 70.8, 68.0, 51.8, 22.5; FAB MS: m/z: calcd for $C_{17}H_{24}NNa_2O_{18}S_2$: 640.0230. found: 640.0202 [M−Na]⁻.

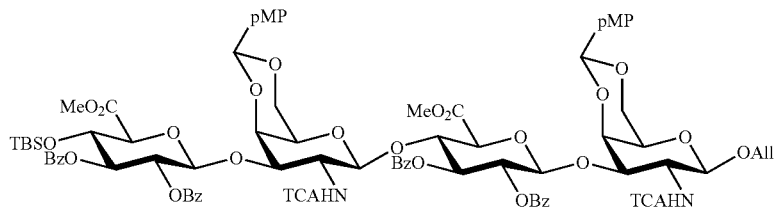

C6. Allyl (methyl 2,3-di-O-benzoyl-4-O-tert-butyldimethylsilyl-β-D-glucopyranosyluronate)-(1→6)-(4,6-O-p-methoxybenzylidene-2-deoxy-2-trichloroacetamide-β-D-galactopyranosyl)-(1→4)-(methyl 2,3-di-O-benzoyl-p-D-glucopyranosyluronate)-(1→6)-4,6-O-p-methoxybenzylidene-2-deoxy-2-trichloroacetamido-β-D-galactopyranoside (15'). 7 (0.20 g, 0.182 mmol) and 8 (0.13 g, 0.15 mmol) were combined and coevaporated with toluene (3×) and put under high vacuum overnight to dry. The mixture was dissolved in CH$_2$Cl$_2$ (3.0 mL) and 4 Å powdered molecular sieves added. The mixture was stirred for 1 h at rt and then cooled to −15° C. Trimethylsilyl trifluoromethanesulfonate (0.5 N solution in CH$_2$Cl$_2$, 0.0068 g, 0.031 mmol, 61 µL) was added and the reaction was stirred at −15° C. for 30 min and then quenched with TEA. The mixture was filtered and concentrated to afford a yellow oil. Purification of this oil by flash chromatography (30→40% EtOAc:hexanes containing 0.1% TEA) afforded 15' (85 mg, 31%) as a white solid. R$_f$ 0.43 (60% EtOAc:hexanes). [α]$_D^{25}$=+13.4 (c=0.5, CH$_2$Cl$_2$); IR (thin film on NaCl): ν=3424, 2956, 2361, 1732, 1638, 1519, 1452, 1368, 1251, 1173, 1093, 1173, 1093, 1070, 1028; $^1$H NMR (600 MHz, CDCl$_3$): δ=7.88-7.80 (m, 8H, ArH), 7.49-7.45 (m, 4H, ArH), 7.38-7.28 (m, 81-1, ArH), 7.22-7.20 (m, 2H, ArH), 7.06 (d, J=8.4 Hz, 2H, C$_6$H$_4$OMe), 6.93 (d, J=8.4 Hz, 2H, C$_6$H$_4$OMe), 6.85 (d, J=6.6 Hz, 1H, NH"), 6.74 (d, J=8.4 Hz, 2H, Ph), 6.66 (d, J=7.2 Hz, 1H, NH), 5.87-5.81 (m, 1H, OCH$_2$CH=CH$_2$), 5.58 (dd, J=7.8, 7.8 Hz, 1H, H-3'), 5.49 (s, 1H, MeOPhCH), 5.44 (dd, J=8.7, 8.7 Hz, 1H, 1H, H-3"'), 5.35 (m, 2H, H-2', H-2"'), 5.23 (d, J=18.0 Hz, 1H, OCH$_2$CH=CH$_2$), 5.20 (s, 1H, MeOPhCH), 5.15 (m, 2H, OCH$_2$CH=CH$_2$, H-1'), 5.11 (d, J=7.8 Hz, 1H, H-1"), 5.03 (d, J=7.2 Hz, 1H, H-1"'), 5.00 (d, J=8.4 Hz, 1H, H-1), 4.68 (dd, J=3.6, 10.8 Hz, 1H, H-3"), 4.58 (dd, J=9.0, 9.0 Hz, 1H, H-4'), 4.39-4.30 (m, 5H, OCH$_2$CH=CH$_2$, H-3, H-4", H-4"', H-6"), 4.14 (m, 2H, H-4, H-5'), 4.06 (m, 3H, OCH$_2$CH=CH$_2$, H-5"', H-6"), 3.83 (s, 3H, PhOCH$_3$), 3.81-3.68 (m, 4H, H-2, H-2", H-6, H-6), 3.80 (s, 3H, PhOCH$_3$), 3.80 (s, 3H, CO$_2$CH$_3$), 3.79 (s, 3H, CO$_2$CH$_3$), 3.48 (s, H-1, H-5"), 3.10 (s, 1H, H-5), 0.72 (s, 9H, (CH$_3$)$_3$CSi), −0.09 (s, 31-1, CH$_3$Si), −0.24 (s, 3H, CH$_3$Si); $^{13}$C NMR (75 MHz, CDCl$_3$): Et=168.8, 168.4, 165.7, 165.4, 165.2, 165.1, 162.2, 161.9, 160.0, 159.8, 133.8, 133.4, 133.3, 133.1, 130.5, 130.4, 130.2, 130.1, 130.0, 129.9, 129.6, 129.5, 129.2, 129.1, 128.6, 128.5, 128.4, 127.9, 127.8, 118.2, 113.7, 113.4, 100.8, 100.5, 100.4, 100.2, 98.6, 97.7, 77.4, 76.4, 75.9, 75.8, 75.3, 75.0, 74.2, 74.1, 73.5, 73.4, 72.1, 71.9, 70.8, 70.6, 69.3, 68.4, 66.9, 55.7, 55.6, 54.8, 53.5, 52.8, 25.7, 18.1, −4.1, −4.8. ESI MS: m/z: calcd for C$_{83}$H$_{89}$Cl$_6$N$_2$O$_{29}$Si: 1819.4. found 1820.4 [M+H]$^+$.

C7. Allyl (methyl 2,3-di-O-benzoyl-4-O-tert-butyldimethylsilyl-β-D-glucopyranosyluronate)-(1→3)-(4,6-O-p-methoxybenzylidene-2-deoxy-2-acetamido-β-D-galactopyranosyl)-(1→4)-(methyl 2,3-di-O-benzoyl-β-D-glucopyranosyluronate)-(1→3)-4,6-O-p-methoxybenzylidene-2-deoxy-2-acetamido-β-D-galactopyranoside (16'). 15' (50 mg, 0.027 mmol) was dissolved in benzene (0.88 mL) and N,N-dimethylacetamide (0.22 mL) and to this were added tributylstamiane (0.10 mL, 0.49 mmol) and 2,2'-azobisisobutyronitrile (2.0 mg). The reaction was stirred at rt for 30 min and then was heated at 80° C. for 5 h. It was cooled to rt, concentrated to afford a yellow-white solid, and purified by silica gel chromatography (80%→100% EtOAc:hexanes) to yield 16' as a white solid (37 mg, 85%). R$_f$ 0.69 (100% EtOAc). $^1$H NMR (300 MHz, CDCl$_3$): δ=7.95-7.84 (m, 8H, ArH), 7.52-7.43 (m, 6H, ArH), 7.38-7.27 (m, 8H, ArH), 7.21 (d, J=9.0 Hz, 2H, C$_6$H$_4$OMe), 6.86 (d, J=8.7 Hz, 2H, C$_6$H$_4$OMe), 6.80 (d, J=9.0 Hz, 2H, Ph C$_6$H$_4$OMe), 5.89-5.76 (m, 1H, OCH$_2$CH=CH$_2$), 5.61 (dd, J=7.2, 8.1 Hz, 1H, H-3'), 5.51 (s, 1H, MeOPhCH), 5.44 (dd, J=8.7, 9.0 Hz, 1H, H-3"'), 5.42 (d, J=6.6 Hz, 1H, NH"), 5.31 (dd, J=6.6, 7.2 Hz, 1H, H-2'), 5.28 (dd, J=7.2, 8.7 Hz, 1H, H-2"), 5.20 (dd, J=0.9, 17.3 Hz, 1H, OCH$_2$CH=CH$_2$), 5.18 (s, 1H, MeOPhCH), 5.13 (d, J=11.4 Hz, 1H, OCH$_2$CH=CH$_2$), 5.11 (d, J=8.1 Hz, 1H, H-1'), 5.05 (d, J=7.2 Hz, 1H, H-1"), 4.98 (d, J=6.6 Hz, H, NH), 4.89 (d, J=7.5 Hz, 1H, H-1), 4.86 (d, J=9.0 Hz, 1H, H-1"'), 4.75 (dd, J=3.3, 10.8 Hz, 1H, H-3"), 4.51 (dd, J=8.1, 9.3 Hz, 1H, H-4'), 4.37-4.25 (m, 5H, OCH$_2$CH=CH$_2$, H-3, H-4", H-4"', H-6"), 4.16 (d, J=9.3 Hz, 1H, H-5"'), 4.06-3.98 (m, 4H, OCH$_2$CH=CH$_2$, H-4, H-5', H-6"), 3.77-3.73 (m, 1H, H-6), 3.80 (s, 3H, PhOCH$_3$), 3.79 (s, 3H, PhOCH$_3$), 3.73 (s, 3H, CO$_2$CH$_3$), 3.70 (s, 3H, CO$_2$CH$_3$), 3.56-3.52 (m, 1H, H-6), 3.46 (s, 1H, H-5"), 3.35-3.26 (m, 2H, H-2, H-2"), 2.84 (s, 1H, H-5), 1.54 (s, 3H, HNC(O)CH$_3$), 1.50 (s, 3H, HNC(O)CH$_3$), 0.70 (s, 9H, (CH$_3$)$_3$CSi), −0.10 (s, 3H, CH$_3$Si), −0.25 (s, 3H, CH$_3$Si). ESI MS: m/z: calcd for C$_{83}$H$_{94}$N$_2$O$_{29}$Si: 1647.2. found 1648.0 [M+Cl]$^-$.

C8. Allyl (methyl 2,3-di-O-benzoyl-4-O-tert-butyldimethylsilyl-β-D-glucopyranosyluronate)-(1→3)-(2-deoxy-2-acetamido-β-D-gal-actopyranosyl)-(1→4)-(methyl 2,3-di-O-benzoyl-β-D-glucopyranosyluronate)-(1→3)-2-deoxy-2-acetamido-βD-galactopyranoside (9). 16' (13 mg, 0.0083 mmol) was dissolved in CH$_2$Cl$_2$ (200 and H$_2$O (24 µL) and

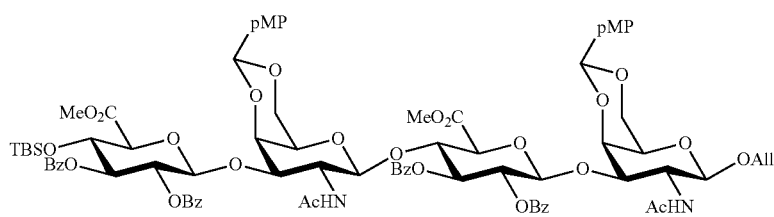

the reaction was covered with aluminum foil and stirred in the dark. 2,3-Dichloro-5,6-dicyano-1,4-benzoquinone (6.0 mg, 0.025 mmol) was added and the reaction stirred for 2 h at rt. The reaction was quenched with MeOH and concentrated to afford a red solid. The crude product was subjected to Sephadex LH-20 (50% $CH_2Cl_2$:MeOH) to afford 9 as a yellow solid (8.5 mg, 75%). $R_f$ 0.2 (100% EtOAc). $^1$H NMR (300 MHz, $CD_3OD$): δ=7.85-7.76 (m, 8H, ArH), 7.47-7.42 (m, 4H, ArH), 7.36-7.27 (m, 8H, ArH), 5.79-5.66 (m, 1H, $OCH_2CH=CH_2$), 5.52 (dd, J=8.4, 8.4 Hz, 1H, H-3'), 5.51 (dd, J=8.4, 9.9 Hz, 1H, H-3'''), 5.27-5.19 (m, 3H), 5.12 (dd, J=1.6 Hz, 17.3 Hz, 1H, $OCH_2CH=CH_2$), 5.00-4.96 (m, 4H), 4.43-4.42 (m, 1H), 4.32-4.26 (m, 2H), 4.20-4.10 (m, 5H), 4.00 (d, J=2.4 Hz, 1H), 3.96-3.88 (m, 3H), 3.70 (s, 3H, $CO_2CH_3$), 3.69 (s, 3H, $CO_2CH_3$), 3.41-3.35 (m, 2H), 3.17-3.10 (m, 3H), 3.04-3.00 (m, 1H), 1.20 (s, 3H, HNC(O)$CH_3$), 1.18 (s, 3H, HNC(O)$CH_3$), 0.66 (s, 9H, $(CH_3)_3CSi$), −0.10 (s, 3H, $CH_3Si$), −0.26 (s, 3H, $CH_3Si$). ESI MS: m/z: calcd for $C_{67}H_{82}N_2NaO_{27}Si$: 1398.4. found 1397.6 $[M+Na]^+$.

The alcohol was deprotected in a manner similar to a procedure from Lucas et. al. (Lucas, H.; Basten, J. E. M.; van Dinther, T. G.; Meuleman, D. G.; van Aelst, S. F.; van Boeckel, C. A. A. *Tetrahedron*, 1990, 46, 8207-8228) The alcohol (4.9 mg, 0.0033 mmol) was dissolved in THF (190 μL) and $H_2O$ (94 μL) and cooled to 0° C. To this were added 1 M aq. LiOH (75 μL) and 30% $H_2O_2$ (38 μL). The reaction stirred at 0° C. for 1 h and at rt for 12 h. At this time, 4 M NaOH (56 μL) and MeOH (280 μL) were added and the reaction stirred for another 12 h. It was then neutralized with Amberlyst IR-120 resin, filtered, and lyophilized to afford an orange solid. The product was purified by Sephadex G-25 UF (0.9% NaCl in $H_2O$) and desalted with Sephadex G-25 UF (100% $H_2O$) to afford 2 as a white solid upon lyophilization (1.9 mg, 25% from 17'). $^1$H NMR (600 MHz, $D_2O$): δ=5.93-5.89 (m, 1H, $OCH_2CH=CH_2$), 5.32 (d, J=17.4 Hz, 1H, $OCH_2CH=CH_2$), 5.13 (d, J=10.2 Hz, 1H, $OCH_2CH=CH_2$), 4.80-4.73 (m, 2H, H-4, H-4''), 4.62-4.55 (m, 2H), 4.50-4.46 (m, 2H), 4.34 (dd, J=4.8, 12.6 Hz, 1H, $OCH_2CH=CH_2$), 4.29

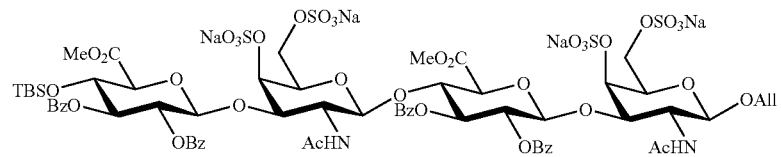

C9. Allyl (methyl 2,3-di-O-benzoyl-4-O-tert-butyldimethylsilyl-β-D-glucopyranosyluronate)-(1→3)-(4,6-di-O-sodium sulfonato-2-deoxy-2-acetamido-β-D-galactopyranosyl)-(1→4)-(methyl 2,3-di-O-benzoyl-β-D-glucopyranosyluronate)-(1→3)-4,6-di-O-sodium sulfonato-2-deoxy-2-acetamido-β-D-galactopyranoside (17'). 9 (13 mg, 0.0095 mmol) was dissolved in DMF (315 μL) and to this was added $SO_3$.TMA (50 mg, 0.36 mmol) and the reaction stirred at 50° C. for 2 d. It was quenched with MeOH, concentrated to afford a yellow solid, and purified on Sephadex LH-20 (50% $CH_2Cl_2$:MeOH) and Sephadex SP C25 (50% $H_2O$:MeOH) to afford 17' as a white solid (11 mg, 67%). $R_f$ 0.29 (EtOAc:pyr:$H_2O$:AcOH, 8:5:3:1). $^1$H NMR (300 MHz, $CD_3OD$): δ=7.92-7.81 (m, 8H, ArH), 7.55-7.45 (m, 4H, ArH), 7.43-7.33 (m, 8H, ArH), 5.87-5.73 (m, 1H, $OCH_2CH=CH_2$), 5.67 (dd, J=9.0, 9.0 Hz, 1H, H-3'), 5.61 (dd, J=9.3, 9.3 Hz, 1H, H-3'''), 5.42-5.32 (m, 3H), 5.19 (dd, J=1.6, 17.3 Hz, 1H, $OCH_2CH=CH_2$), 4.93-4.79 (m, 4H, H-4, H-4''), 4.54-4.52 (m, 1H), 4.49 (dd, J=9.0, 9.6 Hz, 1H, H-4'), 4.40-4.33 (m, 5H), 4.28-4.22 (m, 3H), 4.18 (d, J=9.3 Hz, 1H, H-5'''), 4.08-3.98 (m, 4H), 3.90-3.89 (m, 1H), 3.87 (s, 3H, $CO_2CH_3$), 3.86-3.85 (m, 2H), 3.83 (s, 3H, $CO_2CH_3$), 1.20 (s, 3H, HNC(O)$CH_3$), 1.18 (s, 3H, HNC(O)$CH_3$), 0.73 (s, 9H, $(CH_3)_3CSi$), −0.03 (s, 3H, $CH_3Si$), −0.19 (s, 3H, $CH_3Si$). ESI MS: m/z: calcd for $C_{67}H_{78}N_2Na_3O_{39}S_4Si$: 1760.6. found 1759.8 $[M-Na]^-$.

C10. Allyl (sodium β-D-glucopyranosyluronate)-(1→3)-(4,-6-di-O-sodium sulfonato-2-deoxy-2-acetamido-β-D-galactopyranosyl)-(1→4)-(sodium β-D-glucopyranosyluronate)-(1 sulfonato-2-deoxy-2-acetamido-β-D-galactopyranoside (2). 17' (11 mg, 0.0062 mmol) was dissolved in pyridine (150 μL), THF (150 μL), and $H_2O$ (35 μl). The reaction was cooled to 0° C. and to this was added HF.pyridine (41 μL). It stirred at 0° C. for 1 h and at rt overnight, and following this, was loaded onto a Sephadex LH-20 (50% $CH_2Cl_2$:MeOH) column. The product was concentrated, taken up in $H_2O$, and lyophilized to afford a white solid (4.9 mg) that was immediately used in the next reaction.

(d, J=10.2 Hz, 1H), 4.24-4.18 (m, 2H), 4.13 (d, J=7.8 Hz, 1H), 4.06 (d, J=10.8 Hz, 4H), 3.83-3.75 (m, 2H), 3.70-3.63 (m, 3H), 3.60 (dd, J=7.8, 9.6 Hz, 1H, H-3'), 3.57-3.51 (m, 2H), 3.47 (dd, J=9.0, 9.6 Hz, 1H, H-3'), 3.41 (dd, J=8.4, 8.4 Hz, 1H, H-2'), 3.34 (dd, J=8.4, 8.4 Hz, 1H, H-2'''), 2.04 (s, 3H, HNC(O)$CH_3$), 2.01 (s, 3H, HNC(O)$CH_3$). ESI MS: m/z: calcd for $C_{31}H_{42}N_2Na_5O_{35}S_4$: 1245.9. found 1245.0 $[M-Na]^-$.

C11. Allyl (sodium β-D-glucopyranosyluronate)-(1→3)-(2-deoxy-2-acetamido-β-D-galactopyranosyl)-(1→4)-(sodium β-D-glucopyranosyluronate)-(1→3)-2-deoxy-2-acetamido-β-D-galactopyranoside (3). 9 (8.5 mg, 0.0062 mmol) was dissolved in pyridine (110 and THF (110 μL). The reaction was cooled to 0° C. and to this was added HF.pyridine (30 μL). The reaction stirred at 0° C. for 1 h and at rt overnight. Following this, the mixture was loaded onto a Sephadex LH-20 (50% $CH_2Cl_2$:MeOH) column and the product was a yellow solid (5.3 mg) that was immediately used in the next reaction. The alcohol (5.3 mg, 0.0042 mmol) was dissolved in THF (120 μL) and $H_2O$ (60 μL) and cooled to 0° C. To this were added 1 M aq. LiOH (47 μL) and 30% $H_2O_2$ (23 μL). The reaction stirred at 0° C. for 1 h and at rt for 12 h. At this time, 4 M NaOH (35 μL) and MeOH (173 μL) were added and the reaction stirred for another 12 h. It was neutralized with Amberlyst IR-120 resin, filtered, and lyophilized to afford an orange solid. The product was purified by Sephadex G-25 UF (100% $H_2O$) and lyophilized to afford 3 as a white solid (2.6 mg, 52% from 9). $^1$H NMR (600 MHz, $D_2O$): δ=5.91-5.84 (m, 1H, $OCH_2CH=CH_2$), 5.28 (d, J=17.4 Hz, 1H, $OCH_2CH=CH_2$), 5.23 (d, J=10.2 Hz, 1H, $OCH_2CH=CH_2$), 4.51-4.45 (m, 41-1), 4.31 (dd, J=4.8, 12.9 Hz, 1H, $OCH_2CH=CH_2$), 4.16-4.09 (m, 3H), 4.01-3.96 (m, 2H), 3.78-3.71 (m, 5H), 3.67-3.64 (m, 5H), 3.55 (dd, J=9.0, 9.0 Hz, 1H, H-3'''), 3.48-3.42 (m, 3H), 3.34 (dd, J=8.4, 9.0 Hz, 1H, H-2'), 3.29 (dd, J=7.2, 8.4 Hz, 1H, H-2'''), 1.99 (s, 3H, HNC(O)$CH_3$), 1.98 (s, 3H, HNC(O)$CH_3$). ESI MS: m/z: calcd for $C_{31}H_{47}N_2O_{23}$: 815.7. found 815.4 $[M-H]^-$.

Example 2

The following tetrasaccharide were synthesized using similar procedures as described in example 1:

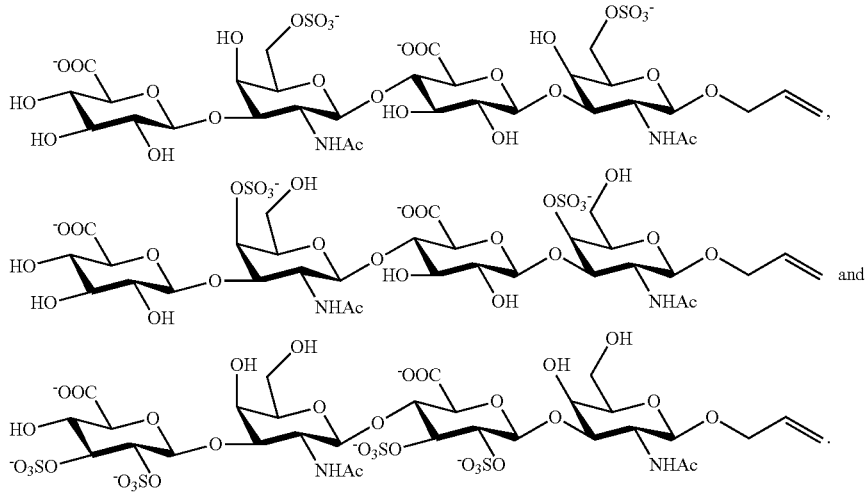

Example 3

Effect on Hippocampal Neuronal Growth

Hippocampal Neuronal Cultures. Hippocampal neuronal cultures were prepared using a modified version of the Goslin and Banker protocol (Goslin, K.; Banker, G. In *Culturing Nerve Cells*; Banker, G.; Goslin, K.; Eds.; MIT Press: Cambridge, Mass., 1991; pp 251-281). Embryos at the E18 stage were obtained from timed-pregnant Sprague-Dawley rats, and the hippocampus from each embryo was dissected. All the hippocampi from one preparation were transferred to a 15 mL conical tube containing 4.5 mL of ice-cold Calcium and Magnesium Free-Hank's Balanced Salt Solution (CMF-HBSS) (GIBCO). Trypsin (2.5%, no EDTA; GIBCO) was added to 5 mL, and the tissue was digested for 15 mM at 37° C. The trypsin solution was removed and the tissue rinsed with 5 mL of CMF-HBSS three times. The tissue was then dissociated in 1 mL of CMF-HBSS by passing through a P1000 pipet tip twenty times. The cells were counted with a hemacytometer and plated on glass coverslips at 80 cells/mm$^2$ and cultivated in minimal Eagle's Medium (MEM) (GIBCO) supplemented with the N2 mixture (GIBCO) and 0.1 mM pyruvate. The cultures were maintained in 5% $CO_2$ at 37° C. Glass coverslips were coated as described by Clement et. al. (Clement, A. M.; Nadanaka, S.; Masayama, K.; Mandl, C.; Sugahara, K.; Faissner, A. *J. Biol. Chem.* 1998, 273, 28444-28453) Briefly, coverslips were precoated with 0.015 mg/mL poly-DL-ornithine (SIGMA) for 1 h at 37° C./5% $CO_2$, washed three times with double distilled $H_2O$, and coated with 0.5 mg/mL of compounds 1-3 in PBS overnight at 37° C./5% $CO_2$. The coverslips were then washed three times with PBS and flooded with MEM+N2 media.

Immunocytochemistry of Hippocampal Neuronal Cultures. After 48 h in culture, hippocampal neurons on coverslips were used for immunostaining. Cells were rinsed one time with PBS, fixed in 4% paraformaldehyde for 20 min at rt, washed twice with PBS, permeablized in 0.3% Triton X-100 for 5 min at rt, and washed twice with PBS. Non-specific binding was blocked with 3% BSA for 1 h at rt. The blocking solution was rinsed off one time with PBS. Cells were then incubated with anti-tau antibodies (rabbit polyclonal, 1:600; SIGMA) in 3% BSA for 2 h at rt. Excess antibody was rinsed away 5 times with PBS. Fluorophore-conjugated secondary antibodies were purchased from Molecular Probes and added for 1 h at 37° C. in 3% BSA. The secondary antibody used was anti-rabbit IgG AlexaFluor 488 (1:600). Excess secondary antibody was washed off 5 times with PBS. The coverslips were mounted onto glass slides using Vectashield mounting medium (Vector Labs) and sealed with clear nail polish. Cells were then subjected to confocal laser microscopy.

Confocal Laser Microscopy. All cells were imaged on a Zeiss Axiovert 100M inverted confocal laser microscope in the Biological Imaging Center in the Beckman Institute at Caltech. The images were captured with LSM Pascal software using a 40× plan-neofluar oil objective. All cells were excited with 488 nm light.

Morphometric Analysis. For quantitative analysis, 50 cells were analyzed per coverslip. Only cells with neurites longer than one cell body diameter were counted. The length of the longest neurite from stained cells was measured using NIH Image 1.52 software. The mean neurite lengths were compared among the different substrate conditions by the ANOVA test using the statistical analysis program StatView (SAS Institute Inc., Cary, N.C.).

Since modifications will be apparent to those of skill in the art, it is intended that the invention be limited only by the scope of the appended claims.

What is claimed is:

1. A method of modulating neuronal growth, said method comprising contacting a cell with an effective amount of a compound of the following formula:

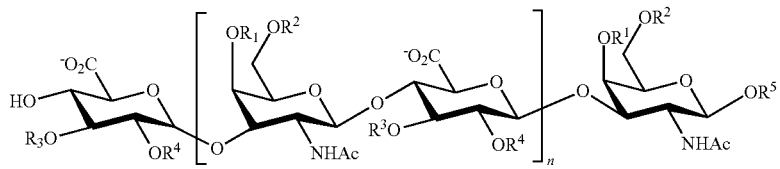

or a pharmaceutically acceptable derivative thereof, wherein each of R1, R2, R3, and R4 are selected as follows:
- (i) R1 is selected from sulfate, phosphate, and carboxylate; R2 is selected from sulfate, phosphate and carboxylate; and R3 and R4 are hydrogen;
- (ii) R3 is selected from sulfate, phosphate, and carboxylate; R4 is selected from sulfate, phosphate, and carboxylate; and R1 and R2 are hydrogen;
- (iii) R1 is selected from sulfate, phosphate, and carboxylate; R2 is selected from sulfate, phosphate, and carboxylate; R3 is selected from sulfate, phosphate, and carboxylate; and R4 is hydrogen;
- (iv) R1 is selected from sulfate, phosphate, and carboxylate; R2 is selected from sulfate, phosphate, and carboxylate; R4 is selected from sulfate, phosphate, and carboxylate; and R3 is hydrogen;
- (v) R2 is selected from sulfate, phosphate, and carboxylate; R4 is selected from sulfate, phosphate, and carboxylate; and R1 and R3 are hydrogen;
- (vi) R1 is selected from sulfate, phosphate, and carboxylate; and R2, R3, and R4 are hydrogen;
- (vii) R2 is selected from sulfate, phosphate, and carboxylate; and R1, R3, and R4 are hydrogen;
- (viii) R3 is selected from sulfate, phosphate, and carboxylate; and R1, R2, and R4 are hydrogen; or
- (ix) R4 is selected from sulfate, phosphate, and carboxylate; and R1, R2, and R3 are hydrogen;

with the provisos that (a) when R1 is sulfate, then R2 is other than H; (b) when R2 is sulfate then R1 is other than H; and R5 is selected from optionally substituted alkyl and optionally substituted alkenyl; and n is 0-100.

2. The method of claim 1, wherein the method results in promotion of neurite outgrowth.

3. The method of claim 1, wherein the method results in inhibition of neurite outgrowth.

4. The method of claim 1, wherein the cell is from a neuronal tissue.

5. The method of claim 1, wherein the cell is a cell from a brain, a central nervous system, or a peripheral nervous system.

6. The method of claim 1, wherein the method results in inhibiting regeneration of an injured nerve.

7. The method of claim 1, wherein the method results in promoting regeneration of an injured nerve.

8. The method of claim 7, wherein the cultured neuronal cell is a hippocampal neuron, a dopaminergic neuron, or a dorsal root ganglion neuron.

9. A method of inducing growth of a differentiated neural stem cell comprising contacting a neural stem cell with an effective amount of a compound of the following formula:

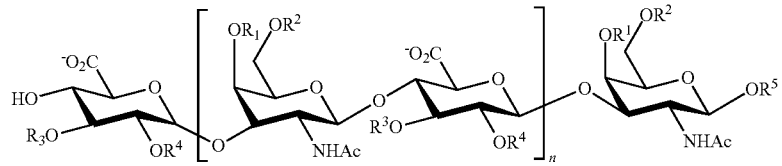

or a pharmaceutically acceptable derivative thereof, wherein each of R1, R2, R3, and R4 are selected as follows:
- (i) R1 is selected from sulfate, phosphate, and carboxylate; R2 is selected from sulfate, phosphate and carboxylate; and R3 and R4 are hydrogen;
- (ii) R3 is selected from sulfate, phosphate, and carboxylate; R4 is selected from sulfate, phosphate, and carboxylate; and R1 and R2 are hydrogen;
- (iii) R1 is selected from sulfate, phosphate, and carboxylate; R2 is selected from sulfate, phosphate, and carboxylate; R3 is selected from sulfate, phosphate, and carboxylate; and R4 is hydrogen;
- (iv) R1 is selected from sulfate, phosphate, and carboxylate; R2 is selected from sulfate, phosphate, and carboxylate; R4 is selected from sulfate, phosphate, and carboxylate; and R3 is hydrogen;

(v) R2 is selected from sulfate, phosphate, and carboxylate; R4 is selected from sulfate, phosphate, and carboxylate; and R1 and R3 are hydrogen;
- (vi) R1 is selected from sulfate, phosphate, and carboxylate; and R2, R3, and R4 are hydrogen;
- (vii) R2 is selected from sulfate, phosphate, and carboxylate; and R1, R3, and R4 are hydrogen;
- (viii) R3 is selected from sulfate, phosphate, and carboxylate; and R1, R2, and R4 are hydrogen; or
- (ix) R4 is selected from sulfate, phosphate, and carboxylate; and R1, R2, and R3 are hydrogen;

with the provisos that (a) when R1 is sulfate, then R2 is other than H; (b) when R2 is sulfate then R1 is other than H; and R5 is selected from optionally substituted alkyl and optionally substituted alkenyl; and n is 0-100.

10. A method of treating a symptom associated with a neurodegenerative disorder or an injury of neural tissue comprising administering to a subject in need thereof an effective amount of a compound of the following formula:

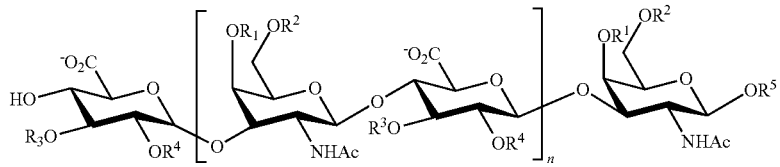

or a pharmaceutically acceptable derivative thereof, wherein each of R1, R2, R3, and R4 are selected as follows:
- (i) R1 is selected from sulfate, phosphate, and carboxylate; R2 is selected from sulfate, phosphate and carboxylate; and R3 and R4 are hydrogen;
- (ii) R3 is selected from sulfate, phosphate, and carboxylate; R4 is selected from sulfate, phosphate, and carboxylate; and R1 and R2 are hydrogen;
- (iii) R1 is selected from sulfate, phosphate, and carboxylate; R2 is selected from sulfate, phosphate, and carboxylate; R3 is selected from sulfate, phosphate, and carboxylate; and R4 is hydrogen;
- (iv) R1 is selected from sulfate, phosphate, and carboxylate; R2 is selected from sulfate, phosphate, and carboxylate; R4 is selected from sulfate, phosphate, and carboxylate; and R3 is hydrogen;

(v) R2 is selected from sulfate, phosphate, and carboxylate; R4 is selected from sulfate, phosphate, and carboxylate; and R1 and R3 are hydrogen;

(vi) R1 is selected from sulfate, phosphate, and carboxylate; and R2, R3, and R4 are hydrogen;

(vii) R2 is selected from sulfate, phosphate, and carboxylate; and R1, R3, and R4 are hydrogen;

(viii) R3 is selected from sulfate, phosphate, and carboxylate; and R1, R2, and R4 are hydrogen; or (ix) R4 is selected from sulfate, phosphate, and carboxylate; and R1, R2, and R3 are hydrogen;

with the provisos that (a) when R1 is sulfate, then R2 is other than H; (b) when R2 is sulfate then R1 is other than H; and R5 is selected from optionally substituted alkyl and optionally substituted alkenyl; and n is 0-100.

11. The method of claim 10, wherein the disorder is a CNS lesion, gliosis, Parkinson's Disease, Alzheimer's Disease, or neuronal degeneration.

12. The method of claim 10, wherein the disorder is spinal cord trauma.

13. A method of modulating the activity of a growth factor comprising contacting a cell with an effective amount a compound comprising:

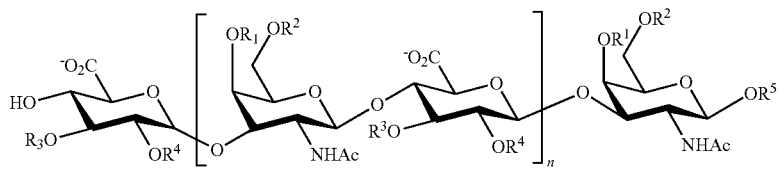

or a pharmaceutically acceptable derivative thereof, wherein each of R1, R2, R3, and R4 are selected as follows:

(i) R1 is selected from sulfate, phosphate, and carboxylate; R2 is selected from sulfate, phosphate and carboxylate; and R3 and R4 are hydrogen;

(ii) R3 is selected from sulfate, phosphate, and carboxylate; R4 is selected from sulfate, phosphate, and carboxylate; and R1 and R2 are hydrogen;

(iii) R1 is selected from sulfate, phosphate, and carboxylate; R2 is selected from sulfate, phosphate, and carboxylate; R3 is selected from sulfate, phosphate, and carboxylate; and R4 is hydrogen;

(iv) R1 is selected from sulfate, phosphate, and carboxylate; R2 is selected from sulfate, phosphate, and carboxylate; R4 is selected from sulfate, phosphate, and carboxylate; and R3 is hydrogen;

(v) R2 is selected from sulfate, phosphate, and carboxylate; R4 is selected from sulfate, phosphate, and carboxylate; and R1 and R3 are hydrogen;

(vi) R1 is selected from sulfate, phosphate, and carboxylate; and R2, R3, and R4 are hydrogen;

(vii) R2 is selected from sulfate, phosphate, and carboxylate; and R1, R3, and R4 are hydrogen;

(viii) R3 is selected from sulfate, phosphate, and carboxylate; and R1, R2, and R4 are hydrogen; or (ix) R4 is selected from sulfate, phosphate, and carboxylate; and R1, R2, and R3 are hydrogen;

with the provisos that (a) when R1 is sulfate, then R2 is other than H; (b) when R2 is sulfate then R1 is other than H; and R5 is selected from optionally substituted alkyl and optionally substituted alkenyl; and n is 0-100.

14. The method of claim 13, wherein the growth factor is a nerve growth factor or fibroblast growth factor.

\* \* \* \* \*

UNITED STATES PATENT AND TRADEMARK OFFICE
CERTIFICATE OF CORRECTION

PATENT NO. : 8,338,387 B2
APPLICATION NO. : 12/511944
DATED : December 25, 2012
INVENTOR(S) : Linda Hsieh-Wilson et al.

It is certified that error appears in the above-identified patent and that said Letters Patent is hereby corrected as shown below:

In Column 1, line 16-17, please replace "Grant No. RGY 0072 sponsored by Human Frontiers Science Program." with -- Grant No. CHE-0239861 awarded by the National Science Foundation. --

Signed and Sealed this
Twelfth Day of March, 2013

Teresa Stanek Rea
*Acting Director of the United States Patent and Trademark Office*